(12) United States Patent
Li et al.

(10) Patent No.: US 11,274,129 B2
(45) Date of Patent: Mar. 15, 2022

(54) METHODS FOR PROTEIN TYROSINE PHOSPHORYLATION PROFILING WITH VARIANT SH2 DOMAINS

(71) Applicant: Shun-Cheng Li, London (CA)

(72) Inventors: Shun-Cheng Li, London (CA); Xuguang Liu, London (CA)

(73) Assignee: Shun-Cheng Li, London (CA)

( * ) Notice: Subject to any disclaimer, the term of this patent is extended or adjusted under 35 U.S.C. 154(b) by 0 days.

(21) Appl. No.: 16/308,729

(22) PCT Filed: Jun. 12, 2017

(86) PCT No.: PCT/CA2017/050719
§ 371 (c)(1),
(2) Date: Dec. 10, 2018

(87) PCT Pub. No.: WO2017/210801
PCT Pub. Date: Dec. 14, 2017

(65) Prior Publication Data
US 2020/0031885 A1 Jan. 30, 2020

Related U.S. Application Data

(60) Provisional application No. 62/348,722, filed on Jun. 10, 2016.

(51) Int. Cl.
*C07K 14/435* (2006.01)
*G01N 33/543* (2006.01)
*G01N 33/574* (2006.01)

(52) U.S. Cl.
CPC ..... *C07K 14/435* (2013.01); *G01N 33/54306* (2013.01); *G01N 33/574* (2013.01); *G01N 2440/14* (2013.01); *G01N 2560/00* (2013.01)

(58) Field of Classification Search
None
See application file for complete search history.

(56) References Cited

U.S. PATENT DOCUMENTS

2010/0279891 A1 11/2010 Daub et al.
2015/0177258 A1 6/2015 Sidhu et al.

FOREIGN PATENT DOCUMENTS

CN 105026422 B 11/2015
WO 2006/134056 A1 12/2006

OTHER PUBLICATIONS

Xie et al., "Dominant-negative Mutants of Grb2 Induced Reversal of the Transformed Phenotypes Caused by the Point Mutation-activated Rat HER-2/Neu", The Journal of Biological Chemistry, 1995, pp. 30717 to 30724, vol. 270-issue No. 51, The American Society for Biochemistry and Molecular Biology, Inc., Printed in USA.
Dey et al., "Evidence for the Direct Interaction of the Insulin-Like Growth Factor I Receptor with IRS-1, Shc, and Grb10", Molecular Endocrinology, 1996, pp. 631 to 641, vol. 10-issue No. 6, The Endocrine Society.
Tartare-Deckert et al., "Evidence for a Differential Interaction of SHC and the Insulin Receptor Substrate-1 (IRS-1) with the Insulin-like Growth Factor-I (IGF-I) Receptor in the Yeast Two-hybrid System", The Journal of Biological Chemistry, 1995, pp. 23456 to 23460, vol. 270-issue No. 40, The American Society for Biochemistry and Molecular Biology, Inc., Printed in USA.
Barretina et al., "The Cancer Cell Line Encyclopedia enables predictive modeling of anticancer drug sensitivity", Nature, pp. 603 to 607, vol. 483-issue No. 7391.
Kenji Takeuchi and Fumiaki Ito, "Target Therapy for Cancer: Anti-cancer Drugs Targeting Growth-Factor Signaling Molecules", Biol. Pharm. Bull., 2011, pp. 1774 to 1780, vol. 34-issue No. 12, Pharmaceutical Society of Japan.
Zaman et al., "Signaling Network Assessment of Mutations and Copy Number Variations Predict Breast Cancer Subtype-Specific Drug Targets", Cell Reports, Oct. 17, 2013, pp. 216 to 223, vol. 5.
Sabbatini et al., "GSK1838705A inhibits the insulin-like growth factor-1 receptor and anaplastic lymphoma kinase and shows anti-tumor activity in experimental models of human cancers", Mol Cancer Ther, Oct. 2009, pp. 2811 to 2820, vol. 8-issue No. 10, American Association for Cancer Research.
Kim et al., "Discovery of a Potent and Selective DDR1 Receptor Tyrosine Kinase Inhibitor", ACS Chemical Biology, 2013, pp. 2145 to 2150, vol. 8, American Chemical Society Publications.
Agrawal and Thelen, et De Graauw Phd, Marjo. Phospho-Proteomics: Methods and Protocols, 2009.
Manning et al., "The protein kinase complement of the human genome", Science, Dec. 6, 2002, pp. 1912 to 1934, vol. 298-issue No. 5600.
Hubbard et al., "Crystal structure of the tyrosine kinase domain of the human insulin receptor", Nature, Dec. 1994, pp. 746 to 754, vol. 372.
Melinkova, I. and Golden, J. "Targeting Protein Kinases", Nature Rev. Drug Discov., Dec. 2004, pp. 993 to 994, vol. 3.
Philip Cohen, "Protein Kinases—the major drug targets of the twenty-first century?", Nat. Rev. Drug Discov., Apr. 2002, pp. 309 to 315, vol. 1.
Merrifield, "Solid Phase Peptide Synthesis. I. The Synthesis of a Tetrapeptide", J. Am. Chem. Assoc., Jul. 20, 1963, pp. 2149 to 2154, vol. 85.
Esteva, F.J., et al., "Molecular predictors of response to trastuzumab and lapatinib in breast cancer", Nat. Rev. Clin. Oncol, Feb. 2010. pp. 98 to 107, vol. 7.

(Continued)

*Primary Examiner* — Kagnew H Gebreyesus

(57) ABSTRACT

There is provided method of profiling protein tyrosine phosphorylation of a sample, the method comprising: contacting the sample with an SH2 Superbinder in order to bind pTyr-including peptides contained in the sample with the SH2 Superbinder; isolating the bound pTyr-including peptides from the sample; and identifying the isolated pTyr-including peptides.

17 Claims, 22 Drawing Sheets

Specification includes a Sequence Listing.

(56) References Cited

OTHER PUBLICATIONS

Felds and Noble, "Solid phase peptide synthesis utilizing 9-fluorenylmethoxycarbonyl amino acids", Int. J. Peptide Protein Res., 1990, pp. 161 to 214, vol. 35.

Zhou, H. et al., "Robust phosphoproteome enrichment using monodisperse microsphere-based immobilized titanium (IV) ion affinity chromatography", Nature Protocols, 2013, pp. 461 to 480, vol. 8-issue No. 3.

Mann et al., "Analysis of Proteins and Proteomes by Mass Spectrometry", Ann. Rev. Biochem., 2001, pp. 437 to 473, vol. 70.

Kuhn et al., "Quantification of C-reactive protein in the serum of patients with rheumatoid arthritis using multiple reaction monitoring mass spectrometry and 13C-labeled peptide standards", Proteomics, 2004, pp. 1175-1186, vol. 4.

Geiger et al., "Super-SILAC mix for quantitative proteomics of human tumor tissue", Nat. Meth., May 2010, pp. 383 to 385, vol. 7-issue No. 5.

Geiger et al., "Use of stable isotope labeling by amino acids in cell culture as a spike-in standard in quantitative proteomics", Nat. Prot., 2011, pp. 147 to 157, vol. 6-issue No. 2.

Thingholm et al., "Highly selective enrichment of phosphorylated peptides using titanium dioxide", Nat. Prot., 2006, pp. 1929 to 1935, vol. 1.

Picotti P., and Aebersold R., "Selected reaction monitoring-based proteomics: workflows, potential, pitfalls and future directions", Nat. Methods, Jun. 2012, pp. 555 to 566, vol. 9-issue No. 6.

Holohan, C. et al., "Cancer drug resistance: an evolving paradigm", Nature Reviews Cancer, Oct. 2013, pp. 714 to 726, vol. 13.

Slamon, D. J. et al., "Human breast cancer: Correlation of relapse and survival with amplification of the HER-2/neu oncogene", Science, Jan. 9, 1987, pp. 177 to 182, vol. 235.

Vogel et al., "Efficacy and safety of trastuzumab as a single agent in first-line treatment of HER2-overexpressing metastatic breast cancer", Journal of Clinical Oncology, 2002, pp. 719 to 726, vol. 20-issue No. 3.

Zhou, H. et al., "Specific phosphopeptide enrichment with immobilized titanium ion affinity chromatography adsorbent for phosphoproteome analysis", J. Proteome Res., 2008, pp. 3957 to 3967, vol. 7-issue No. 9.

Debnath, J. et al., "Morphogenesis and oncogenesis of MCF-10A mammary epithelial acini grown in three-dimensional basement membrane cultures", Methods, 2003, pp. 256 to 268, vol. 30.

Sepp-Lorenzino, L. et al., "Signal transduction pathways induced by heregulin in MDA-MB-453 breast cancer cells", Oncogene, 1996, pp. 1679 to 1687, vol. 12.

Levitzki, A., "Tyrosine kinase inhibitors: views of selectivity, sensitivity, and clinical performance", Annu. Rev. Pharmacol. Toxicol., 2013, pp. 161 to 185, vol. 53.

International Search Report, dated Sep. 5, 2017, issued in international phase of this application.

Written Opinion, dated Sep. 5, 2017, issued in international phase of this application.

Huang et al., "Defining the Specificity Space of the Human Src Homology 2 Domain", Molecular & Cellular Proteomics, 2008, pp. 768 to 784, vol. 7-issue No. 4, The American Society for Biochemistry and Molecular Biology, Inc.

Machida et al., "Profiling the Global Tyrosine Phosphorylation State", Molecular & Cellular Proteomics, 2003, pp. 215 to 233, vol. 2-issue No. 4, The American Society for Biochemistry and Molecular Biology, Inc.

Dierck et al., "Quantitative multiplexed profiling of cellular signaling networks using phosphotyrosine-specific DNA-tagged SH2 domains", Nature Methods, Sep. 2006, vol. 3-issue No. 9, pp. 737 to 744.

Machida et al., "High-Throughput Phosphotyrosine Profiling Using SH2 Domains", Molecular Cell, Jun. 22, 2007, pp. 899 to 915, vol. 26, Elsevier Inc.

Liu et al., "A Comprehensive Immunoreceptor Phosphotyrosine-based Signaling Network Revealed by Reciprocal Protein-Peptide Array Screening", Molecular & Cellular Proteomics, 2015, pp. 1846 to 1858, vol. 14-issue No. 7, The American Society for Biochemistry and Molecular Biology, Inc.

Bian et al., "Ultra-deep tyrosine phosphoproteomics enabled by a phophotyrosine superbinder", Nature Chemical Biology, Nov. 2016, pp. 959 to 966, vol. 12.

Tong et al., "Protein-phosphotyrosine proteome profiling by superbinder-SH2 domain affinity purification mass spectrometry, sSH2-AP-MS", Proteomics, 2017, pp. 1 to 5, vol. 17-issue No. 6, WILEY-VCH Verlag GmbH & Co. KGaA, Weinheim.

Deng et al., "Biphasic Affinity Chromatographic Approach for Deep Tyrosine Phosphoproteome Analysis", Analytical Chemistry, 2017, pp. 2405 to 2410, vol. 89, American Chemical Society.

Li et al., "Sensitive Approaches for the Assay of the Global Protein Tyrosine Phosphorylation in Complex Samples Using a Mutated SH2 Domain", Analytical Chemistry, 2017, pp. 2304 to 2311, vol. 89, American Chemical Society.

Jadwin et al., "The application of modular protein domains in proteomics", FBBS Letters, 2012, pp. 2586 to 2596, vol. 586, Federation of European Biochemical Societies, Published by Elsevier B.V.

Kaneko et al., "Superbinder SH2 Domains Act as Antagonists of Cell Signaling", Biochemistry, Sep. 25, 2012, vol. 5-issue No. 243 ra68, pp. 1 to 10.

Morgan Huse and John Kuriyan, "The Conformational Plasticity Review of Protein Kinases", Cell, May 3, 2002, pp. 275 to 282, vol. 109.

Bayliss et al., "On the molecular mechanisms of mitotic kinase activation", Open Biology, 2012, pp. 1 to 20, vol. 2-issue No. 120136.

Mark A. Lemmon and Joseph Schlessinger, "Cell signaling by receptor-tyrosine kinases", Cell, Jun. 25, 2010, pp. 1117 to 1134, vol. 141-issue No. 7.

Taylor et al., "Evolution of the eukaryotic protein kinases as dynamic molecular switches", Phil. Trans. R. Soc. B, 2012, pp. 2517 to 2528, vol. 367, The Royal Society.

Drake et al., "Clinical Targeting of Mutated and Wild-Type Protein Tyrosine Kinases in Cancer", Molecular and Cellular Biology, May 2014, pp. 1722 to 1732, vol. 34-issue No. 10, American Society for Microbiology.

Gross et al., "Targeting cancer with kinase inhibitors", The Journal of Clinical Investigation, May 2015, pp. 1780 to 1789, vol. 125-issue No. 5.

Patterson et al., "Protein kinase inhibitors in the treatment of inflammatory and autoimmune diseases", Clinical and Experimental Immunology, 2013, pp. 1 to 10, vol. 176, British Society for Immunology, Clinical and Experimental Immunology.

Gordona Vlahovic and Jeffrey Crawford, "Activation of Tyrosine Kinases in Cancer", The Oncologist, 2003, pp. 531 to 538, vol. 8.

Sharma et al., "Ultradeep Human Phosphoproteome Reveals a Distinct Regulatory Nature of Tyrand Ser/Thr-Based Signaling", Cell Reports, Sep. 11, 2014, pp. 1583 to 1594, vol. 8.

Wissing et al., "Proteomics Analysis of Protein Kinases by Target Class-selective Prefractionation and Tandem Mass Spectrometry", Molecular & Cellular Proteomics, 2007, pp. 537 to 547, vol. 6-issue No. 3, The American Society for Biochemistry and Molecular Biology, Inc.

Gerber et al., "Absolute quantification of proteins and phosphoproteins from cell lysates by tandem MS", PNAS, Jun. 10, 2003, pp. 6940 to 6945, vol. 100-issue No. 12.

Hardt et al., "Absolute Quantitation of Targeted Endogenous Salivary Peptides using Heavy Isotope-labeled Internal Standards and High-Resolution Selective Reaction Monitoring Mass Spectrometry", Thermo Scientific Application Note: 451, 2008, Thermo Fisher Scientific Inc.

Peterson et al., "Parallel Reaction Monitoring for High Resolution and High Mass Accuracy Quantitative, Targeted Proteomics", Molecular & Cellular Proteomics, 2012, pp. 1475 to 1488, vol. 11-issue No. 11, The American Society tor Biochemistry and Molecular Biology, Inc.

Daub et al., "Kinase-Selective Enrichment Enables Quantitative Phosphoproteomics of the Kinome across the Cell Cycle", Molecular Cell, Aug. 8, 2008, pp. 438 to 448, vol. 31, Elsevier Inc.

(56) References Cited

OTHER PUBLICATIONS

Ong et al., "Stable Isotope Labeling by Amino Acids in Cell Culture, SILAC, as a Simple and Accurate Approach to Expression Proteomics", Molecular & Cellular Proteomics, 2002, pp. 376 to 386, vol. 1-issue No. 5, The American Society for Biochemistry and Molecular Biology, Inc.

Cole et al., "Further evidence that the tyrosine phosphorylation of glycogen synthase kinase-3 (GSK3) in mammalian cells is an autophosphorylation event", Biochem. J., 2004, pp. 249 to 255, vol. 377, Biochemical Society, Printed in Great Britain.

Hughes et al., "Modulation of the glycogen synthase kinase-3 family by tyrosine phosphorylation", The EMBO Journal, 1993, pp. 803 to 808, vol. 12-issue No. 2, Oxford University Press.

Michael A Gillette and Steven A Carr, "Quantitative analysis of peptides and proteins in biomedicine by targeted mass spectrometry", Nat Methods, Jan. 2013, pp. 28 to 34, vol. 10-issue No. 1, Nature America, Inc.

Daniel C. Liebler and Lisa J. Zimmerman, "Targeted Quantitation of Proteins by Mass Spectrometry", Biochemistry, 2013, pp. 3797 to 3806, vol. 52, American Chemical Society.

Liu et al., "A method for systematic mapping of protein lysine methylation identifies new functions for HP1β in DNA damage repair", Mol. Cell, Jun. 6, 2013, pp. 723 to 735, vol. 50-issue No. 5.

Hurwitz et al., "Vorinostat/SAHA-induced apoptosis in malignant mesothelioma is FLIP/caspase 8-dependent and HR23B-independent", European Journal of Cancer, 2012, pp. 1096 to 1107, vol. 48, Elsevier Ltd.

Wilson et al., "Procaspase 8 overexpression in non-small-cell lung cancer promotes apoptosis induced by FLIP silencing", Cell Death and Differentiation, 2009, pp. 1352 to 1361, vol. 16, Macmillan Publishers Limited.

Devika Gajria and Sarat Chandarlapaty, "HER2-amplified breast cancer mechanisms of trastuzumab resistance and novel targeted therapies", Expert Rev Anticancer Ther., Feb. 2011, pp. 263 to 275, vol. 11-issue No. 2, Expert Reviews Ltd.

Bishop et al., "A chemical switch for inhibitor-sensitive alleles of any protein kinase", Nature, Sep. 21, 2000, pp. 395 to 401, vol. 407, Macmillan Magazines Ltd.

Boersema et al., "In-depth Qualitative and Quantitative Profiling of Tyrosine Phosphorylation Using a Combination of Phosphopeptide Immunoaffinity Purification and Stable Isotope Dimethyl Labeling", Molecular & Cellular Proteomics, 2010, pp. 84 to 99, vol. 9-issue No. 1, The American Society for Biochemistry and Molecular Biology, Inc.

Olsen et al., "Global, In Vivo, and Site-Specific Phosphorylation Dynamics in Signaling Networks", Cell, Nov. 3, 2006, pp. 635 to 648, vol. 127, Elsevier Inc.

Lundby et al., "Quantitative maps of protein phosphorylation sites across 14 different rat organs and tissues", Nature Communications, 2012, pp. 1 to 10, vol. 3-issue No. 876, Macmillan Publishers Limited.

Wang et al., "A Fully Automated System with Online Sample Loading, Isotope Dimethyl Labeling and Multidimensional Separation for High-Throughput Quantitative Proteome Analysis", Analytical Chemistry, Apr. 1, 2010, pp. 3007 to 3015, vol. 82-issue No. 7, American Chemical Society.

Matlock et al., "ProteomeScout: a repository and analysis resource for post-translational modifications and proteins". Nucleic Acids Research, 2015, pp. D521 to D530, vol. 43, Published by Oxford University Press.

Geiger et al., "Comparative Proteomic Analysis of Eleven Common Cell Lines Reveals Ubiquitous but Varying Expression of Most Proteins", Molecular & Cellular Proteomics, 2012, vol. 11-issue No. 3, The American Society for Biochemistry and Molecular Biology, Inc.

Stokes et al., "Complementary PTM Profiling of Drug Response in Human Gastric Carcinoma by Immunoaffinity and IMAC Methods with Total Proteome Analysis", Proteomes, 2015, pp. 159 to 183, vol. 3.

Hubbard et al., "Autoregulatory Mechanisms in Protein-tyrosine Kinases", The Journal of Biological Chemistry, 1998, pp. 11987 to 11990, vol. 273-issue No. 20, The American Society for Biochemistry and Molecular Biology, Inc., Printed in the USA.

Qian et al., "The tensin-3 protein, including its SH2 domain, is phosphorylated by Src and contributes to tumorigenesis and metastasis", Cancer Cell, Sep. 8, 2009, pp. 246 to 258, vol. 16-issue No. 3, Elsevier Inc.

Jin et al., "Tyrosine Phosphorylation of the Lyn Src Homology 2 (SH2) Domain Modulates Its Binding Affinity and Specificity", Molecular & Cellular Proteomics, 2015, pp. 695 to 706, vol. 14-issue No. 3, The American Society for Biochemistry and Molecular Biology, Inc.

Andersen et al., "Structural and Evolutionary Relationships among Protein Tyrosine Phosphatase Domains", Molecular and Cellular Biology, Nov. 2001, pp. 7117 to 7136, vol. 21-issue No. 21, American Society for Microbiology.

Feng Liu and Jonathan Chernoff, "Protein tyrosine phosphatase 1B interacts with and is tyrosine phosphorylated by the epidermal growth factor receptor", Biochem. J., 1997, pp. 139 to 145, vol. 327, Printed in Great Britain.

Mitra et al., "SHP-2 is a Novel Target of ABL Kinases During Cell Proliferation", J Cell Sci., Oct. 15, 2008, pp. 3335 to 3346, vol. 121(Pt 20).

Extended European Search Report dated Apr. 9, 2020, issued in the related European Application No. EP 17809514.7.

Yaoi et al., "Src Homology 2 Domain-based High Throughput Assays for Profiling Downstream Molecules in Receptor Tyrosine Kinase Pathways", Molecular and Cellular Proteomics, 2006, vol. 5-issue No. 5, pp. 959 to 968, The American Society for Biochemistry and Molecular Biology, Inc.

Jones et al., "A quantitative protein interaction network for the ErbB receptors using protein microarrays", Nature, Jan. 12, 2006, vol. 439, pp. 168 to 174, Nature Publishing Group.

First Chinese Office Action issued by the Chinese Patent Office dated Sep. 1, 2021 in connection with Chinese Patent Application No. 201780047062.X, 14 pages.

Kazuya Machida, et al., "Profiling the Global Tyrosine Phosphorylation State" Molecular & Cellular Proteomics, pp. 215-233, May 17, 2003.

FIG. 8

SEQUENCE LISTING

<160> NUMBER OF SEQ ID NOS: 15

<210> SEQ ID NO 1
<211> LENGTH: 536
<212> TYPE: PRT
<213> ORGANISM: Homo sapiens

<400> SEQUENCE: 1

```
Met Gly Ser Asn Lys Ser Lys Pro Lys Asp Ala Ser Gln Arg Arg
1               5                   10                  15

Ser Leu Glu Pro Ala Glu Asn Val His Gly Ala Gly Gly Ala Phe
            20                  25                  30

Pro Ala Ser Gln Thr Pro Ser Lys Pro Ala Ser Ala Asp Gly His Arg
            35                  40                  45

Gly Pro Ser Ala Ala Phe Ala Pro Ala Ala Glu Pro Lys Leu Phe
        50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
            115                 120                 125

Thr Gly Gln Thr Gly Tyr Ile Pro Ser Asn Tyr Val Ala Pro Ser Asp
        130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
            245                 250                 255

Gly Leu Ala Lys Asp Ala Trp Glu Ile Pro Arg Glu Ser Leu Arg Leu
        260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
            325                 330                 335

Ile Tyr Ile Val Thr Glu Tyr Met Ser Lys Gly Ser Leu Leu Asp Phe
        340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
        370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415
```

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
    450                 455                 460

Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535

<210> SEQ ID NO 2
<211> LENGTH: 217
<212> TYPE: PRT
<213> ORGANISM: Homo sapiens

<400> SEQUENCE: 2

Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Lys Pro His Pro Trp Phe Phe Gly Lys
    50                  55                  60

Ile Pro Arg Ala Lys Ala Glu Glu Met Leu Ser Lys Gln Arg His Asp
65                  70                  75                  80

Gly Ala Phe Leu Ile Arg Glu Ser Glu Ser Ala Pro Gly Asp Phe Ser
                85                  90                  95

Leu Ser Val Lys Phe Gly Asn Asp Val Gln His Phe Lys Val Leu Arg
            100                 105                 110

Asp Gly Ala Gly Lys Tyr Phe Leu Trp Val Val Lys Phe Asn Ser Leu
        115                 120                 125

Asn Glu Leu Val Asp Tyr His Arg Ser Thr Ser Val Ser Arg Asn Gln
    130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
            180                 185                 190

Trp Trp Lys Gly Ala Cys His Gly Gln Thr Gly Met Phe Pro Arg Asn
        195                 200                 205

Tyr Val Thr Pro Val Asn Arg Asn Val
    210                 215

<210> SEQ ID NO 3
<211> LENGTH: 537
<212> TYPE: PRT
<213> ORGANISM: Homo sapiens

<400> SEQUENCE: 3

| | | | | | | | | | | | | | | |
|---|---|---|---|---|---|---|---|---|---|---|---|---|---|---|
|Met|Gly|Cys|Val|Gln|Cys|Lys|Asp|Lys|Glu|Ala|Thr|Lys|Leu|Thr|Glu|
|1| | | |5| | | | |10| | | | |15| |

Glu Arg Asp Gly Ser Leu Asn Gln Ser Ser Gly Tyr Arg Tyr Gly Thr
           20                  25                  30

Asp Pro Thr Pro Gln His Tyr Pro Ser Phe Gly Val Thr Ser Ile Pro
               35                  40                  45

Asn Tyr Asn Asn Phe His Ala Ala Gly Gly Gln Gly Leu Thr Val Phe
 50                  55                  60

Gly Gly Val Asn Ser Ser Ser His Thr Gly Thr Leu Arg Thr Arg Gly
65                   70                  75                  80

Gly Thr Gly Val Thr Leu Phe Val Ala Leu Tyr Asp Tyr Glu Ala Arg
                 85                  90                  95

Thr Glu Asp Asp Leu Ser Phe His Lys Gly Glu Lys Phe Gln Ile Leu
            100                 105                 110

Asn Ser Ser Glu Gly Asp Trp Trp Glu Ala Arg Ser Leu Thr Thr Gly
        115                 120                 125

Glu Thr Gly Tyr Ile Pro Ser Asn Tyr Val Ala Pro Val Asp Ser Ile
    130                 135                 140

Gln Ala Glu Glu Trp Tyr Phe Gly Lys Leu Gly Arg Lys Asp Ala Glu
145                 150                 155                 160

Arg Gln Leu Leu Ser Phe Gly Asn Pro Arg Gly Thr Phe Leu Ile Arg
                165                 170                 175

Glu Ser Glu Thr Thr Lys Gly Ala Tyr Ser Leu Ser Ile Arg Asp Trp
            180                 185                 190

Asp Asp Met Lys Gly Asp His Val Lys His Tyr Lys Ile Arg Lys Leu
        195                 200                 205

Asp Asn Gly Gly Tyr Tyr Ile Thr Thr Arg Ala Gln Phe Glu Thr Leu
    210                 215                 220

Gln Gln Leu Val Gln His Tyr Ser Glu Arg Ala Ala Gly Leu Cys Cys
225                 230                 235                 240

Arg Leu Val Val Pro Cys His Lys Gly Met Pro Arg Leu Thr Asp Leu
                245                 250                 255

Ser Val Lys Thr Lys Asp Val Trp Glu Ile Pro Arg Glu Ser Leu Gln
            260                 265                 270

Leu Ile Lys Arg Leu Gly Asn Gly Gln Phe Gly Glu Val Trp Met Gly
        275                 280                 285

Thr Trp Asn Gly Asn Thr Lys Val Ala Ile Lys Thr Leu Lys Pro Gly
    290                 295                 300

Thr Met Ser Pro Glu Ser Phe Leu Glu Glu Ala Gln Ile Met Lys Lys
305                 310                 315                 320

Leu Lys His Asp Lys Leu Val Gln Leu Tyr Ala Val Val Ser Glu Glu
                325                 330                 335

Pro Ile Tyr Ile Val Thr Glu Tyr Met Asn Lys Gly Ser Leu Leu Asp
            340                 345                 350

Phe Leu Lys Asp Gly Glu Gly Arg Ala Leu Lys Leu Pro Asn Leu Val
        355                 360                 365

Asp Met Ala Ala Gln Val Ala Ala Gly Met Ala Tyr Ile Glu Arg Met
    370                 375                 380

Asn Tyr Ile His Arg Asp Leu Arg Ser Ala Asn Ile Leu Val Gly Asn
385                 390                 395                 400

Gly Leu Ile Cys Lys Ile Ala Asp Phe Gly Leu Ala Arg Leu Ile Glu

```
                            405                 410                 415

Asp Asn Glu Tyr Thr Ala Arg Gln Gly Ala Lys Phe Pro Ile Lys Trp
            420                 425                 430

Thr Ala Pro Glu Ala Ala Leu Tyr Gly Arg Phe Thr Ile Lys Ser Asp
            435                 440                 445

Val Trp Ser Phe Gly Ile Leu Leu Thr Glu Leu Val Thr Lys Gly Arg
450                 455                 460

Val Pro Tyr Pro Gly Met Asn Asn Arg Glu Val Leu Glu Gln Val Glu
465                 470                 475                 480

Arg Gly Tyr Arg Met Pro Cys Pro Gln Asp Cys Pro Ile Ser Leu His
            485                 490                 495

Glu Leu Met Ile His Cys Trp Lys Lys Asp Pro Glu Glu Arg Pro Thr
            500                 505                 510

Phe Glu Tyr Leu Gln Ser Phe Leu Glu Asp Tyr Phe Thr Ala Thr Glu
            515                 520                 525

Pro Gln Tyr Gln Pro Gly Glu Asn Leu
            530                 535

<210> SEQ ID NO 4
<211> LENGTH: 109
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: Wild-type human Src SH2 domain

<400> SEQUENCE: 4

Asp Ser Ile Gln Ala Glu Glu Trp Tyr Phe Gly Lys Ile Thr Arg Arg
1               5                   10                  15

Glu Ser Glu Arg Leu Leu Leu Asn Ala Glu Asn Pro Arg Gly Thr Phe
            20                  25                  30

Leu Val Arg Glu Ser Glu Thr Thr Lys Gly Ala Tyr Cys Leu Ser Val
        35                  40                  45

Ser Asp Phe Asp Asn Ala Lys Gly Leu Asn Val Lys His Tyr Lys Ile
50                  55                  60

Arg Lys Leu Asp Ser Gly Gly Phe Tyr Ile Thr Ser Arg Thr Gln Phe
65                  70                  75                  80

Asn Ser Leu Gln Gln Leu Val Ala Tyr Tyr Ser Lys His Ala Asp Gly
            85                  90                  95

Leu Cys His Arg Leu Thr Thr Val Cys Pro Thr Ser Lys
            100                 105

<210> SEQ ID NO 5
<211> LENGTH: 109
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: TrM human Src SH2 domain

<400> SEQUENCE: 5

Asp Ser Ile Gln Ala Glu Glu Trp Tyr Phe Gly Lys Ile Thr Arg Arg
1               5                   10                  15

Glu Ser Glu Arg Leu Leu Leu Asn Ala Glu Asn Pro Arg Gly Thr Phe
            20                  25                  30
```

```
Leu Val Arg Glu Ser Glu Thr Val Lys Gly Ala Tyr Ala Leu Ser Val
         35                  40                  45

Ser Asp Phe Asp Asn Ala Lys Gly Leu Asn Val Lys His Tyr Leu Ile
 50                  55                  60

Arg Lys Leu Asp Ser Gly Gly Phe Tyr Ile Thr Ser Arg Thr Gln Phe
 65                  70                  75                  80

Asn Ser Leu Gln Gln Leu Val Ala Tyr Tyr Ser Lys His Ala Asp Gly
                 85                  90                  95

Leu Cys His Arg Leu Thr Thr Val Cys Pro Thr Ser Lys
                100                 105
```

<210> SEQ ID NO 6
<211> LENGTH: 104
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: Wild-type human Grb2 SH2 domain

<400> SEQUENCE: 6

```
Met Lys Pro His Pro Trp Phe Phe Gly Lys Ile Pro Arg Ala Lys Ala
 1               5                  10                  15

Glu Glu Met Leu Ser Lys Gln Arg His Asp Gly Ala Phe Leu Ile Arg
                 20                  25                  30

Glu Ser Glu Ser Ala Pro Gly Asp Phe Ser Leu Ser Val Lys Phe Gly
             35                  40                  45

Asn Asp Val Gln His Phe Lys Val Leu Arg Asp Gly Ala Gly Lys Tyr
 50                  55                  60

Phe Leu Trp Val Val Lys Phe Asn Ser Leu Asn Glu Leu Val Asp Tyr
 65                  70                  75                  80

His Arg Ser Thr Ser Val Ser Arg Asn Gln Gln Ile Phe Leu Arg Asp
                 85                  90                  95

Ile Glu Gln Val Pro Gln Gln Pro
                100
```

<210> SEQ ID NO 7
<211> LENGTH: 109
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: TrM human Grb2 SH2 domain

<400> SEQUENCE: 7

```
Met Lys Pro His Pro Trp Phe Phe Gly Lys Ile Pro Arg Ala Lys Ala
 1               5                  10                  15

Glu Glu Met Leu Ser Lys Gln Arg His Asp Gly Ala Phe Leu Ile Arg
                 20                  25                  30

Glu Ser Glu Ser Val Pro Gly Asp Phe Ala Leu Ser Val Lys Phe Gly
             35                  40                  45

Asn Asp Val Gln His Phe Leu Val Leu Arg Asp Gly Ala Gly Lys Tyr
 50                  55                  60

Phe Leu Trp Val Val Lys Phe Asn Ser Leu Asn Glu Leu Val Asp Tyr
 65                  70                  75                  80

His Arg Ser Thr Ser Val Ser Arg Asn Gln Gln Ile Phe Leu Arg Asp
                 85                  90                  95
```

```
Ile Glu Gln Val Pro Gln Gln Pro Leu Ile Asn Glu Phe
            100                 105
```

```
<210> SEQ ID NO 8
<211> LENGTH: 111
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: Wild-type human Fyn SH2 domain

<400> SEQUENCE: 8
```

```
Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Thr Lys Gly Ala Tyr Ser
        35                  40                  45

Leu Ser Ile Arg Asp Trp Asp Asp Met Lys Gly Asp His Val Lys His
    50                  55                  60

Tyr Lys Ile Arg Lys Leu Asp Asn Gly Gly Tyr Tyr Ile Thr Thr Arg
65                  70                  75                  80

Ala Gln Phe Glu Thr Leu Gln Gln Leu Val Gln His Tyr Ser Glu Arg
                85                  90                  95

Ala Ala Gly Leu Cys Cys Arg Leu Val Val Pro Cys His Lys Gly
            100                 105                 110
```

```
<210> SEQ ID NO 9
<211> LENGTH: 111
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: TrM human Fyn SH2 domain

<400> SEQUENCE: 9
```

```
Ala Pro Val Asp Ser Ile Gln Ala Glu Glu Trp Tyr Phe Gly Lys Leu
1               5                   10                  15

Gly Arg Lys Asp Ala Glu Arg Gln Leu Leu Ser Phe Gly Asn Pro Arg
            20                  25                  30

Gly Thr Phe Leu Ile Arg Glu Ser Glu Thr Val Lys Gly Ala Tyr Ala
        35                  40                  45

Leu Ser Ile Arg Asp Trp Asp Asp Met Lys Gly Asp His Val Lys His
    50                  55                  60

Tyr Leu Ile Arg Lys Leu Asp Asn Gly Gly Tyr Tyr Ile Thr Thr Arg
65                  70                  75                  80

Ala Gln Phe Glu Thr Leu Gln Gln Leu Val Gln His Tyr Ser Glu Arg
                85                  90                  95

Ala Ala Gly Leu Cys Cys Arg Leu Val Val Pro Cys His Lys Gly
            100                 105                 110
```

```
<210> SEQ ID NO 10
<211> LENGTH: 361
<212> TYPE: PRT
<213> ORGANISM: artificial
<220> FEATURE:
<223> OTHER INFORMATION: SH2 protein domain
```

```
<220> FEATURE:
<221> NAME/KEY: MISC_FEATURE
<223> OTHER INFORMATION: Wild-type human Src SH2 domain with
      hexahistidine and GST tags

<400> SEQUENCE: 10

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
            35                  40                  45

Arg Asp Glu Gly Asp Lys Trp Arg Asn Lys Lys Phe Glu Leu Gly Leu
50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
            115                 120                 125

Phe Glu Thr Leu Lys Val Asp Phe Leu Ser Lys Leu Pro Glu Met Leu
130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
            195                 200                 205

Ser Ser Lys Tyr Ile Ala Trp Pro Leu Gln Gly Trp Gln Ala Thr Phe
210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Asp Ser Ile Gln
                245                 250                 255

Ala Glu Glu Trp Tyr Phe Gly Lys Ile Thr Arg Arg Glu Ser Glu Arg
            260                 265                 270

Leu Leu Leu Asn Ala Glu Asn Pro Arg Gly Thr Phe Leu Val Arg Glu
            275                 280                 285

Ser Glu Thr Thr Lys Gly Ala Tyr Cys Leu Ser Val Ser Asp Phe Asp
290                 295                 300

Asn Ala Lys Gly Leu Asn Val Lys His Tyr Lys Ile Arg Lys Leu Asp
305                 310                 315                 320

Ser Gly Gly Phe Tyr Ile Thr Ser Arg Thr Gln Phe Asn Ser Leu Gln
                325                 330                 335

Gln Leu Val Ala Tyr Tyr Ser Lys His Ala Asp Gly Leu Cys His Arg
            340                 345                 350

Leu Thr Thr Val Cys Pro Thr Ser Lys
            355                 360

<210> SEQ ID NO 11
<211> LENGTH: 361
```

<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: TrM human Src SH2 domain with hexahistidine and GST tags

<400> SEQUENCE: 11

```
Met Lys His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
            35                  40                  45

Arg Asp Glu Gly Asp Lys Trp Arg Asn Lys Phe Glu Leu Gly Leu
50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
            85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
            115                 120                 125

Phe Glu Thr Leu Lys Val Asp Phe Leu Ser Lys Leu Pro Glu Met Leu
            130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
            165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
            195                 200                 205

Ser Ser Lys Tyr Ile Ala Trp Pro Leu Gln Gly Trp Gln Ala Thr Phe
210                 215                 220

Gly Gly Gly Asp His Pro Pro Thr Ser Gly Ser Gly Gly Gly Gly
225                 230                 235                 240

Trp Met Ser Glu Asn Leu Tyr Phe Gln Gly Ala Met Asp Ser Ile Gln
            245                 250                 255

Ala Glu Glu Trp Tyr Phe Gly Lys Ile Thr Arg Arg Glu Ser Glu Arg
            260                 265                 270

Leu Leu Leu Asn Ala Glu Asn Pro Arg Gly Thr Phe Leu Val Arg Glu
            275                 280                 285

Ser Glu Thr Val Lys Gly Ala Tyr Ala Leu Ser Val Ser Asp Phe Asp
            290                 295                 300

Asn Ala Lys Gly Leu Asn Val Lys His Tyr Leu Ile Arg Lys Leu Asp
305                 310                 315                 320

Ser Gly Gly Phe Tyr Ile Thr Ser Arg Thr Gln Phe Asn Ser Leu Gln
            325                 330                 335

Gln Leu Val Ala Tyr Tyr Ser Lys His Ala Asp Gly Leu Cys His Arg
            340                 345                 350

Leu Thr Thr Val Cys Pro Thr Ser Lys
            355                 360
```

<210> SEQ ID NO 12
<211> LENGTH: 109
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: QuadM human Src SH2 domain

<400> SEQUENCE: 12

Asp Ser Ile Gln Ala Glu Glu Trp Tyr Phe Gly Lys Ile Thr Arg Arg
1               5                   10                  15

Glu Ser Glu Arg Leu Leu Leu Asn Ala Glu Asn Pro Arg Gly Thr Phe
            20                  25                  30

Leu Val Arg Glu Ser Glu Thr Val Lys Gly Ala Tyr Ala Leu Ser Val
        35                  40                  45

Ser Asp Phe Asp Asn Ala Lys Gly Leu Asn Val Lys His Tyr Leu Ile
    50                  55                  60

Arg Lys Leu Asp Ser Gly Gly Phe Tyr Ile Trp Ser Arg Thr Gln Phe
65                  70                  75                  80

Asn Ser Leu Gln Gln Leu Val Ala Tyr Tyr Ser Lys His Ala Asp Gly
                85                  90                  95

Leu Cys His Arg Leu Thr Thr Val Cys Pro Thr Ser Lys
            100                 105

<210> SEQ ID NO 13
<211> LENGTH: 136
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: QuadM human Src SH2 domain with hexahistidine
      tag

<400> SEQUENCE: 13

Met Lys His His His His His His Pro Met Ser Asp Tyr Asp Ile Pro
1               5                   10                  15

Thr Thr Glu Asn Leu Tyr Phe Gln Gly Ala Met Asp Ser Ile Gln Ala
            20                  25                  30

Glu Glu Trp Tyr Phe Gly Lys Ile Thr Arg Arg Glu Ser Glu Arg Leu
        35                  40                  45

Leu Leu Asn Ala Glu Asn Pro Arg Gly Thr Phe Leu Val Arg Glu Ser
    50                  55                  60

Glu Thr Val Lys Gly Ala Tyr Ala Leu Ser Val Ser Asp Phe Asp Asn
65                  70                  75                  80

Ala Lys Gly Leu Asn Val Lys His Tyr Leu Ile Arg Lys Leu Asp Ser
                85                  90                  95

Gly Gly Phe Tyr Ile Trp Ser Arg Thr Gln Phe Asn Ser Leu Gln Gln
            100                 105                 110

Leu Val Ala Tyr Tyr Ser Lys His Ala Asp Gly Leu Cys His Arg Leu
        115                 120                 125

Thr Thr Val Cys Pro Thr Ser Lys
    130                 135

<210> SEQ ID NO 14
<211> LENGTH: 109

```
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: double-mutant human Src SH2 domain

<400> SEQUENCE: 14

Asp Ser Ile Gln Ala Glu Glu Trp Tyr Phe Gly Lys Ile Thr Arg Arg
1               5                   10                  15

Glu Ser Glu Arg Leu Leu Leu Asn Ala Glu Asn Pro Arg Gly Thr Phe
            20                  25                  30

Leu Val Arg Glu Ser Glu Thr Val Lys Gly Ala Tyr Ala Leu Ser Val
        35                  40                  45

Ser Asp Phe Asp Asn Ala Lys Gly Leu Asn Val Lys His Tyr Lys Ile
    50                  55                  60

Arg Lys Leu Asp Ser Gly Gly Phe Tyr Ile Thr Ser Arg Thr Gln Phe
65                  70                  75                  80

Asn Ser Leu Gln Gln Leu Val Ala Tyr Tyr Ser Lys His Ala Asp Gly
                85                  90                  95

Leu Cys His Arg Leu Thr Thr Val Cys Pro Thr Ser Lys
            100                 105

<210> SEQ ID NO 15
<211> LENGTH: 225
<212> TYPE: PRT
<213> ORGANISM: artificial
<220> FEATURE:
<223> OTHER INFORMATION: SH2 protein domain
<220> FEATURE:
<221> NAME/KEY: MISC_FEATURE
<223> OTHER INFORMATION: QuadM-TrM human Src SH2 tandem domain

<400> SEQUENCE: 15

Asp Ser Ile Gln Ala Glu Glu Trp Tyr Phe Gly Lys Ile Thr Arg Arg
1               5                   10                  15

Glu Ser Glu Arg Leu Leu Leu Asn Ala Glu Asn Pro Arg Gly Thr Phe
            20                  25                  30

Leu Val Arg Glu Ser Glu Thr Val Lys Gly Ala Tyr Ala Leu Ser Val
        35                  40                  45

Ser Asp Phe Asp Asn Ala Lys Gly Leu Asn Val Arg His Tyr Leu Ile
    50                  55                  60

Arg Lys Leu Asp Ser Gly Gly Phe Tyr Ile Trp Ser Arg Thr Gln Phe
65                  70                  75                  80

Asn Ser Leu Gln Gln Leu Val Ala Tyr Tyr Ser Lys His Ala Asp Gly
                85                  90                  95

Leu Ser His Arg Leu Thr Thr Val Ser Pro Thr Ser Lys Gly Gly Ser
            100                 105                 110

Gly Gly Ser Met Asp Ser Ile Gln Ala Glu Glu Trp Tyr Phe Gly Lys
        115                 120                 125

Ile Thr Arg Arg Glu Ser Glu Arg Leu Leu Leu Asn Ala Glu Asn Pro
    130                 135                 140

Arg Gly Thr Phe Leu Val Arg Glu Ser Glu Thr Val Lys Gly Ala Tyr
145                 150                 155                 160

Ala Leu Ser Val Ser Asp Phe Asp Asn Ala Lys Gly Leu Asn Val Arg
                165                 170                 175

His Tyr Leu Ile Arg Lys Leu Asp Ser Gly Gly Phe Tyr Ile Thr Ser
            180                 185                 190
```

```
Arg Thr Gln Phe Asn Ser Leu Gln Gln Leu Val Ala Tyr Tyr Ser Lys
        195                 200                 205

His Ala Asp Gly Leu Ser His Arg Leu Thr Thr Val Ser Pro Thr Ser
    210                 215                 220

Lys
225
```

METHODS FOR PROTEIN TYROSINE PHOSPHORYLATION PROFILING WITH VARIANT SH2 DOMAINS

CROSS REFERENCE TO RELATED APPLICATION

This application claims benefit of, and priority from, U.S. provisional patent application No. 62/384,722, filed on Jun. 10, 2016, the contents of which are fully incorporated herein by reference.

FIELD

The disclosure relates generally to methods of detecting protein tyrosine phosphorylation in a sample, including tyrosine phosphorylation associated with the activity of protein kinases and immune function, including using mass spectrometry techniques.

BACKGROUND

Protein phosphorylation by various protein kinases has an important role in manifold eukaryotic cell processes, including metabolism, cell growth, cell cycle progression, apoptosis, cytoskeletal architecture, and differentiation. Protein phosphorylation is particularly central to cell signalling, with phosphorylation acting to, among other effects, control enzyme activity, immune response, protein subcellular localization, protein degradation, and protein-protein interactions.

In eukaryotes, protein phosphorylation occurs almost exclusively on tyrosine (Tyr), serine (Ser), and threonine (Thr) residues. Of the around 518 protein kinases encoded by the human genome, around 90 are categorized as Tyr kinases (TKs), with most of the remainder categorized as Ser/Thr kinases (STKs) and a smaller subset as dual-specificity kinases that phosphorylate Tyr and Ser/Thr (Manning, G. et al., "The protein kinase complement of the human genome", (2002) *Science* 298:1912). By definition, a protein kinase has the conserved catalytic domain that phosphorylates proteins, but it can also have additional domains, such as protein-protein interaction domains (Manning, G. et al., "The protein kinase complement of the human genome", (2002) *Science* 298:1912).

Protein kinase activity often requires the phosphorylation of the kinases themselves. In general, the kinase activity of TKs is activated by the phosphorylation of one or more Tyr residues in a so-called activation loop. The activation loop is a short, conserved peptide located in the catalytic core of the kinase. In most TKs, as well as in a number of STKs or dual-specificity kinases (e.g., MAP kinases) and lipid kinases (e.g., phosphatidylinositide 3-kinases), the activation loop harbors 1-3 tyrosine residues that are among the first tyrosine(s) to be phosphorylated during kinase activation (Huse, M. and Kuriyan, J. "The conformational plasticity of protein kinases" (2002), *Cell* 109:275-282; Taylor, S. S., et al. "Evolution of the eukaryotic protein kinases as dynamic molecular switches" (2012) *Phil. Trans. R. Soc. B.* 367:2517-2528; Bayliss, R., et al. "On the molecular mechanisms of mitotic kinase activation", (2012) *Open Biology* 2:120136). Structural studies have revealed that phosphorylation of the activation loop enables kinase substrate and ATP binding (Hubbard, S. R. et al., "Crystal structure of the tyrosine kinase domain of the human insulin receptor", (1994) *Nature* 372:746-754; Lemmon, M. A., and Schlessinger, J. "Cell signaling by receptor tyrosine kinases", (2010) *Cell* 141:1117-1134).

In addition, many TKs also have Tyr residues outside the activation loop, or even outside the kinase domain itself. The phosphorylation of these additional Tyr residues can, amongst other effects, positively or negatively auto-regulate the activity of the kinase domain or bind to interaction domains on other proteins.

More than half of the 90 human TKs have been implicated in one or more cancers, inflammatory disorders, and other diseases (Drake et al., "Clinical targeting of mutated and wild-type protein tyrosine kinases in cancer" (2014) *Mol. Cell. Biol.* 34: 1722-1732; Melnikova, I. and Golden, J., "Targeting protein kinases" (2004) *Nature Rev. Drug Discov.* 3: 993-994). Thus, tyrosine kinases are considered one of the most important groups of drug targets, and at present, numerous drugs that target TKs have been approved, and many more are in various stages of pre-clinical and clinical evaluation (Gross, S. et al., "Targeting cancer with kinase inhibitors" (2015) *J. Clin. Invest.* 125: 1780-1789; Patterson, H. et al., "Protein kinase inhibitors in the treatment of inflammatory and autoimmune diseases" (2013) *Clin. Exp. Immunol.* 176: 1-10; Vlahovic, G. and Crawford, J., "Activation of tyrosine kinases in cancer" (2003) *Oncologist* 8: 531-538; Cohen P., "Protein kinases—the major drug targets of the twenty-first century?" (2002) *Nat. Rev. Drug Discov.* 1: 309-315).

Kinases, in particular tyrosine kinases, also play central roles in regulating immune functions through the phosphorylation of specific tyrosine residues contained within the cytoplasmic domain of immunoreceptors. Specifically, immune signaling is regulated by Immunoreceptor Tyr-based Regulatory Motifs (ITRMs) which include Immunoreceptor Tyr-based Activating Motifs (ITAM), Immunoreceptor Tyr-based Inhibitory Motifs (ITIM), and Immunoreceptor Tyr-based Switching Motifs (ITSM) (Liu, H. et al., "A comprehensive immunoreceptor phosphotyrosine-based signaling network revealed by reciprocal protein-peptide array screening" (2015) *Mol. Cell. Proteomics* 14: 1846-1858).

Advances in mass spectrometry (MS)-based proteomics have made it possible to identify ~90% of all proteins encoded by the human genome. A recent proteomic analysis suggests that more than three-quarters of expressed human proteins can be phosphorylated (Sharma, K. et al., "Ultra-deep human phosphoproteome reveals a distinct regulatory nature of tyr and ser/thr-based signaling", (2014) *Cell Rep.* 8:1583-94).

A critical step in identifying phosphorylated amino acids is the enrichment of phosphoproteins or phosphopeptides prior to MS analysis. Immobilized metal ion affinity chromatography (IMAC), often comprising use of $TiO_2$ or $Ti^{4+}$, can be used to enrich phosphopeptides. In Sharma et al., phosphopeptides from HeLa S3 cells were enriched using $TiO_2$ beads. Of the approximately 38,000 phosphosites identified, 84.1% were pSer, 15.5% were pThr, and 0.4% were phosphotyrosine (pTyr). These relative proportions were similar to those estimated decades earlier using radioisotope labelling.

Identification of cellular Tyr phosphosites by MS can be improved by enrichment with anti-pTyr antibodies (e.g., 4G10, p-Tyr-100) and by pre-treatment of cells with pervanadate, an inhibitor of protein phosphatases. In Sharma et al., combining pervanadate pre-treatment and enrichment with anti-pTyr antibodies allowed for the identification of more than 2,000 Tyr-phosphorylated peptides from about 1,300 proteins in HeLa S3 cells. Only around 18% of the Tyr phosphosites identified by Sharma et al. appeared to be novel. Those authors concluded that, although coverage of Ser/Thr phosphorylation events appeared to be very comprehensive, the Tyr phosphoproteome was far from complete.

Cellular signal transduction relies on regulated and dynamic protein-protein interactions, which are often mediated by modular domains. One example is the Src homology 2 (SH2) domain, which binds to peptides containing pTyr. The human genome encodes around 120 SH2 domains. All known SH2 domain structures conform to a conserved domain fold. Typically, SH2 domains have a pTyr-binding pocket along with a second pocket or subsite that confers specificity for residues C-terminal to pTyr in the ligand peptide (Huang, H. et al., "Defining the specificity space of the human SRC homology 2 domain" (2008) *Mol. Cell. Proteomics* 7:768-784).

In addition, SH2 domains are known to bind to ITRMs (Liu, H. et al., "A comprehensive immunoreceptor phosphotyrosine-based signaling network revealed by reciprocal protein-peptide array screening" (2015) *Mol. Cell. Proteomics* 14: 1846-1858).

SUMMARY

This disclosure relates to the use of variant SH2 domains referred to as Superbinders for profiling protein tyrosine phosphorylation within a biological sample. The methods provide for detection and optional quantification of tyrosine phosphorylation associated with cellular processes, including the activity of protein kinases and ITRM-mediated immune signalling, by combining Superbinder-based enrichment of tyrosine-phosphorylated peptides with mass spectrometry.

It has recently been discovered that the affinity of an SH2 domain for peptides with a pTyr residue can be markedly enhanced. For example, markedly enhanced affinity can be obtained by substituting one, two or three specific residues in the pTyr-binding pocket (Kaneko, T. et al., "SH2 Superbinders act as antagonists of cell signaling", (2012) *Sci. Signal.* 5: ra68; U.S. patent application Ser. No. 14/388,592). Introducing these substitutions into analogous positions in the SH2 domains from three human proteins—the tyrosine kinase Src, the tyrosine kinase Fyn, and the adapter protein Grb2—markedly increases the affinity of these domains for pTyr-including peptides.

For instance, variant Src SH2 domains with such substitutions show increased binding affinities for physiological and artificial pTyr-including peptides (Table 1; shown are equilibrium dissociation constant ($K_d$) values in the μM unit.).

TABLE 1

Binding affinity of wild type and variant Src SH2 domains to a panel of pTyr peptides.

| pTyr peptide | Sequence | Wild type | Lys15Leu | Thr8Val/Cys10Ala | Triple mutant |
|---|---|---|---|---|---|
| VEGFR1-pTyr$^{1213}$ | DVRpYVNAAKF | 6.5 | 1.7 | 1.8 | 0.023 |
| EGFR-pTyr$^{978}$ | PQRpYLVIQGD | 3.7 | 0.82 | 0.39 | 0.0077 |
| EGFR-pTyr$^{1110}$ | NPVpYHNQPLN | 6.9 | 1.7 | 4.5 | 0.076 |
| MidT-pTyr$^{324}$ | EPQpYEEIPIYL | 0.13 | 0.051 | 0.027 | 0.0038 |
| RSKL-pTyr$^{423}$ | YQHpYDLDLKD | 3.9 | 1.6 | 0.90 | 0.013 |
| ShcA-pTyr$^{239}$ | DHQpYYNDFPG | 0.70 | 0.20 | 0.10 | 0.0038 |
| ShcA-pTyr$^{317}$ | DPSpYVNVQNL | 2.2 | 0.49 | 0.39 | 0.0075 |
| Designed | GGpYGG | (>30) | 25 | 25 | 0.51 |

Similarly, a variant Fyn SH2 domain with three particular amino acid substitutions at three particular amino acid positions (a "triple mutant" or "TrM" as referred to herein) binds to a pTyr-including peptide found in the sequence of the receptor tyrosine kinase EGFR with an equilibrium dissociation constant ($K_d$) of 9.7 nanomolar (nM). The wild-type Fyn SH2 domain binds to the same peptide with a $K_d$ of 3.7 micromolar (μm), indicating that the TrM Fyn SH2 domain binds around 380-fold tighter.

It has now been surprisingly discovered that the increased affinity of SH2 Superbinders for pTyr-including peptides is sufficiently sensitive so as to allow for detection of changes, including small changes, in phosphorylation status in a cell, such as those that may arise due to disease or exposure to drug treatments.

By comparing the phosphorylation status between different samples, it may be possible to use the methods of the present disclosure to assess different aspects of cellular processes associated with phosphorylation, including as related to disease and treatment, for example disease status, disease prognosis, disease progression, suitability or effectiveness of treatment, drug resistance, status of kinase activity, or status of immune signalling.

Thus, the present disclosure provides for the first time a method to identify hundreds of Tyr phosphosites and to optionally quantify the incidence of phosphorylation at such sites simultaneously, including from minute amounts of cells, tissues, biopsies, or other biological samples, thus enabling the systematic profiling of the protein tyrosine phosphorylation status within the biological sample.

Such profiling can indicate the pattern and optionally the intensity of pTyr signaling, including protein kinase- and ITRM-mediated signal transduction, which in turn can provide an indication of various states of the cells within the biological sample, including immune function and disease states such as cancer. In some embodiments, the methods allow for detection of pTyr status that reflects kinase activity levels of essentially all known TKs. For example, in some embodiments the methods are allow for identification, and optionally quantification, of the activity of 89/90 of known TKs. When comparison with profiles obtained for appropriate control samples is included in the methods, the methods in different embodiments can detect changes in regulatory events within cells that may be associated with disease, or treatments that target inhibition of a specific TK.

In accordance with an aspect of the present disclosure, there is provided method of profiling protein tyrosine phosphorylation of a test sample, the method comprising contacting the test sample with an SH2 Superbinder in order to bind pTyr-including peptides contained in the test sample with the SH2 Superbinder; isolating the bound pTyr-including peptides from the test sample; and identifying the isolated pTyr-including peptides.

The method may further comprise quantifying the isolated pTyr-including peptides.

Identifying and/or quantifying may comprise mass spectrometry techniques, including for example multiple reaction monitoring (MRM), selective reaction monitoring (SRM) or parallel reaction monitoring (PRM) techniques.

The SH2 Superbinder may be a variant of a mammalian SH2 domain, and may be a variant of a Src, Grb2 or Fyn SH2 domain. The SH2 Superbinder may be a triple mutant SH2 variant, or may be a quadruple mutant SH2 variant. The SH2 Superbinder may comprise a sequence of SEQ ID NO: 5, 7, 9, 11, 12, 13, 14 or 15. The SH2 Superbinder may be contained within a fusion protein that comprises one or more additional SH2 Superbinders.

The SH2 Superbinder may be immobilized on a solid support.

Isolating may comprise high performance liquid chromatography techniques or ultra performance chromatography techniques.

The sample may be obtained from a subject, including a human subject, and the subject may be to be diagnosed with cancer, or may be known to have cancer, including for example breast cancer, lung cancer, prostate cancer or leukemia. The sample may be, for example, serum, plasma, urine, blood, tissue or a tissue extract.

The sample may have been exposed to a tyrosine kinase inhibitor, a chemotherapy agent, a PD-1 inhibitor, or a CTLA-4 inhibitor.

The method may comprise identifying a pTyr-including peptide corresponding to a substrate of a specific protein tyrosine kinase, a pTyr-including peptide corresponding to a substrate of a specific protein tyrosine phosphatase, a pTyr-including peptide from a kinase including from an activation loop of a protein kinase or from outside the activation loop of the protein kinase, an ITRM of an immunoreceptor including an ITIM, ITSM or ITAM, and/or a regulatory region of a protein tyrosine phosphatase including a positive regulatory region or a negative regulatory region. The kinase may be a tyrosine kinase, a serine/threonine kinase, a dual-specificity kinase, a MAP kinase, or a lipid kinase.

The method may further comprise the use of a control sample. Thus, the method may comprise contacting a control sample with the SH2 Superbinder in order to bind pTyr-including peptides contained in the control sample with the SH2 Superbinder; isolating the bound pTyr-including peptides from the control sample; identifying the isolated pTyr-including peptides; and comparing the profile obtained for the test sample with the profile obtained for a control sample.

The control sample may be, for example, a sample from the same source as the test sample but obtained at a different time point than the test sample, a sample from the same source as the test sample but having different exposure to a drug as compared to the test sample, from a source known to be free from a disease, or from a source known to be have a disease or to be involved in a disease.

BRIEF DESCRIPTION OF THE DRAWINGS

In the figures, which illustrate, by way of example only, embodiments of the present invention:

FIG. 8 is an annotated chart that sets out, for each the 9 cell lines subjected to the phosphoproteomic analysis of FIG. 4, the Z-scores (calculated against all pTyr sites detected in a given cell line) of the log 2 m/z peak intensity values for the activation loop pTyr site(s) in TKs encoded by the indicated genes, which are themselves organized into families of cytoplasmic TKs (CTK) and receptor TKs (RTK) and various subfamilies thereof (e.g., CTK_FAK, RTK_EPH, etc.); the extent of red shading indicates the magnitude of a positive Z-score; the extent of blue shading indicates the magnitude of a negative Z-score; the results for three TKs (Ddr1, ErbB2, IGF-1R) in five of the cell lines were used to predict which TK inhibitors would specifically suppress growth of some of these cell lines in FIGS. 11A to 11C infra (rectangles with thick lines); the extent of variance between cell lines for a given TK is indicated by the number and the bar graph oriented vertically on the right-hand side of the chart;

in FIG. 11A to 11C, error bars indicate 1 standard deviation;

in FIG. 13C, exposure of the trastuzumab-resistant clone to both drugs results in a statistically-significant decrease in cell proliferation compared to each drug alone (P<0.01); in FIGS. 13A, 13B, and 13C, error bars represent standard deviations from three independent experiments;

FIG. 19A is from a non-small cell lung cancer biopsy and FIG. 19B is from a breast cancer biopsy; Peaks corresponding to the most active kinases (i.e. FGFR1, GSK3, TXK) or infiltrated T cells (i.e. CD3δ, CD3ζ) are labelled;

DETAILED DESCRIPTION

Figure 1:
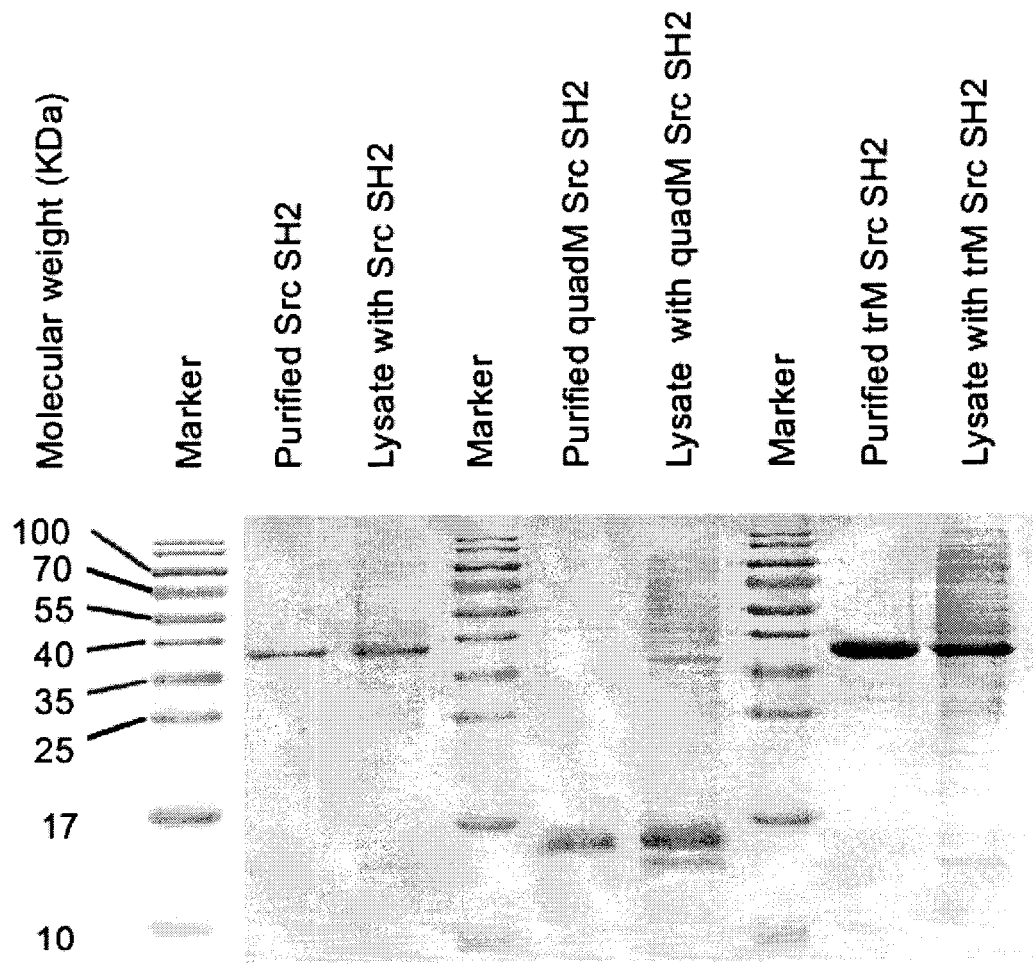
FIG. 1 is an image of a Coomassie-stained acrylamide gel illustrating the purification of hexahistidine($His_6$)-tagged or $His_6$- and GST-double tagged recombinant proteins from *E. coli* cell lysates, namely wild-type human Src SH2 domain ($His_6$/GST-tagged; SEQ ID NO: 10), a TrM human Src SH2 Superbinder ($His_6$/GST-tagged; SEQ ID NO: 11), and a quadruply-mutated (QuadM) human Src SH2 Superbinder ($His_6$-tagged; SEQ ID NO: 13); the approximate molecular weight in kilodaltons (kDa) of the purified proteins is indicated by a mixture of marker proteins.

In brief overview, it has now been recognized that protein tyrosine phosphorylation, including tyrosine phosphorylation implicated in protein kinase activations and immunoreceptor pTyr-based signalling, in various biological samples, including healthy and diseased human cells and tissues, can be profiled by enriching for pTyr-including peptides using particular variant SH2 domains (referred to herein as Superbinders, as described herein). The SH2 Superbinders have also been found to allow for comparison of profiles obtained for test samples and various controls, and for determination of specific status of kinase activity within the test samples. This allows for use of these methods in various different applications, including disease diagnosis and prognosis, elucidation of kinase activation in disease pathways, including as related to immune signalling, and resistance or sensitivity to TK inhibition therapy.

pTyr-including peptides derived from Tyr phosphosites such as those in the activation loop of protein kinases, or those on ITRMs, can bind to a Superbinder upon contact, and the bound peptides can be removed from most other peptides in the sample, identified, and optionally quantified, thereby providing a profile of phosphotyrosine signaling activity, including the activity of TKs (and other kinases with pTyr-including peptides in their activation loops) and immunoreceptors relevant to the ITRMs in the sample.

The methods of the present disclosure in different embodiments allow for identification of hundreds of pTyr sites, and optionally the quantification of the incidence of phosphorylation at such sites, simultaneously, from minute amounts of cells, tissues, biopsies, or other biological samples, thus enabling the systematic profiling of protein tyrosine phosphorylation within the sample. Such profiling provides the phosphorylation status of identified Tyr phosphosites, based on identification and optional quantification of pTyr-including peptides in the sample, and thus may be used as an indication of the pattern and intensity of pTyr signalling with the sample, including tyrosine phosphorylation associated with the activity of protein kinases within the sample, as well as tyrosine phosphorylation associated with ITRM-mediated signalling within the sample. Such profiling relies on the use of one or more SH2 Superbinders to isolate a set of pTyr-containing peptides from the sample, which may be enhanced as compared to other isolation methods due to the enhanced affinity of SH2 Superbinders for pTyr-containing peptides compared to parent SH2 domains. Compared with existing methods that individually assess one or a small set of phosphoproteins in a sample, the described methods provide a more comprehensive assessment of protein tyrosine phosophorylation that is present in any given sample based on a single assay.

Thus, as described in greater detail herein, it is presently contemplated that the protein tyrosine phosphorylation, including in a human tissue sample, may be best profiled by using one or more SH2 Superbinders, including such as those described in the Examples set out below, to enrich for pTyr-including peptides derived from the cells or tissue in the biological sample, and by identifying and optionally quantifying the pTyr-including peptides (for example from TK activation loops or ITRMs) by targeted MS techniques. This advantageous combination of enrichment of the pTyr sites that can be captured and the identification and optional quantification afforded by mass spectrometry together may allow for the various different uses and applications of these methods as described herein.

As used herein, profiling of protein tyrosine phosphorylation refers to the identification and optional quantification of a set of pTyr-including peptides in a sample.

Similarly, as referred to herein, a profile refers to the results obtained from profiling of a sample. Thus, a profile of protein tyrosine phosphorylation refers to the results obtained from such profiling.

The set of pTyr-including peptides identified by the profiling may include all the pTyr-including peptides that are detectable in the sample by binding with the Superbinder and subsequent identification and optional quantification, or may be some subset of all such detectable pTyr-including peptides. Depending on the information desired from the profiling, one or more specific pTyr-including peptides derived from one or more pTyr sites may be the focus of the identification and optional quantification, for example, one or more particular pTyr-including peptides from pTyr sites in the activation loops of protein kinases, in the ITRMs of immunoreceptors, or in the regulatory regions of protein tyrosine phosphatases.

Profiling of protein tyrosine phosphorylation may include profiling of protein kinase activity or profiling of immunoreceptor phosphotyrosine signalling, based on the identified set of pTyr-including peptides, and correlation with specific protein kinase activation loops and phosphorylation targets or specific known pTyr-including peptides within ITRMs of immunoreceptors. Different embodiments of profiling of protein tyrosine phosphorylation in accordance with the methods of this disclosure are also further described herein.

The protein tyrosine phosphorylation profile thus may be used as an indicator of kinase or other pTyr signalling activity, including TK or immunoreceptor activity, present in the sample, and profiling of protein tyrosine phosphorylation may be performed, for example, for a specific TK, phosphatase or immunoreceptor, or set of TKs, phosphatases or immunoreceptors, for specific conditions such as treatment with a particular drug or drug combination, or to monitor treatment over the course of a treatment regimen.

Thus, profiling of protein tyrosine phosphorylation may include profiling of protein kinase activity. As used herein, profiling of protein kinase activity refers to identifying in a sample the activity of one or more protein kinases through the identification and optional quantification of pTyr-including peptides derived from protein kinases, including from within or outside of the activation loop of a kinase. Such protein kinases include TKs, STKs or other dual-specificity kinases, MAP kinases, or lipid kinases.

As well, profiling of protein tyrosine phosphorylation may thus include profiling of immunoreceptor phosphotyrosine signalling. As used herein, profiling of immunoreceptor phosphotyrosine signalling activity or immune profiling refers to identifying in a sample the activity of one or more immunoreceptors or other regulators of immune function through the identification and optional quantification of pTyr-including peptides derived from ITRMs or other regulators of immune function. Profiling of immunoreceptor phosphotyrosine signalling may be conducted by identifying and optionally quantifying pTyr-including peptides corresponding to ITAM, ITIM and ITSM sequences (for example those set out in Table 2). Phosphorylation of the tyrosine residue in the ITAM, ITIM or ITSM sequences present in immunoreceptors is indicative of the activation of the corresponding immunoreceptors, including immunoreceptors involved in either positive immune regulation via the ITAM sequences or negative immune regulation via the ITIM sequences. ITAM, ITIM and ITSM sequences can be found in different immune cells, including B cells, T cells, natural killer cells and macrophages.

TABLE 2

ITIM/ITAM/ITSM associated with human immunoreceptors

| Sequence | Type | UniProt ID | Tyr Postion |
|---|---|---|---|
| PLDpYEFLATEG | ITAM | VSIG4_HUMAN | 388 |
| PLDpYEFLATEG | ITIM | VSIG4_HUMAN | 388 |
| NGNpYARLLDTV | ITAM | VSIG4_HUMAN | 377 |

TABLE 2-continued

ITIM/ITAM/ITSM associated with human immunoreceptors

| Sequence | Type | UniProt ID | Tyr Postion |
|---|---|---|---|
| GQEpYQIIAQIN | ITAM | VSIG4_HUMAN | 367 |
| KTGpYLSIIMDP | ITSM | VGFR3_HUMAN | 812 |
| KTGpYLSIVMDP | ITSM | VGFR2_HUMAN | 801 |
| ASPpYPGVKIDE | ITIM | VGFR2_HUMAN | 1106 |
| ASEpYKALMTEL | ITIM | VGFR1_HUMAN | 872 |
| KTDpYLSIIMDP | ITSM | VGFR1_HUMAN | 794 |
| GSPpYPGVQMDE | ITIM | VGFR1_HUMAN | 1100 |
| TSCpYCLLDPFA | ITIM | UNC5D_HUMAN | 658 |
| LSTpYALVGHST | ITIM | UNC5C_HUMAN | 667 |
| HLYpYCQLEASA | ITIM | UNC5A_HUMAN | 560 |
| VVRpYRVRKSYS | ITIM | UFO_HUMAN | 490 |
| QTPpYAG1ENAE | ITSM | TYRO3_HUMAN | 733 |
| ESPpYQELQGQR | ITAM | TYOBP_HUMAN | 91 |
| ESPpYQELQGQR | ITIM | TYOBP_HUMAN | 91 |
| SDVpYSDLNTQR | ITAM | TYOBP_HUMAN | 102 |
| LLQpYLSLPFFR | ITIM | TUTLA_HUMAN | 926 |
| PVTpYATVIFPG | ITIM | TRML1_HUMAN | 281 |
| RSRpYVRLRQRL | ITIM | TLR9_HUMAN | 980 |
| HSQpYLRLRQRI | ITIM | TLR8_HUMAN | 989 |
| HLFpYWDVWFIY | ITIM | TLR8_HUMAN | 853 |
| HVApYSQVFKET | ITIM | TLR7_HUMAN | 1041 |
| ISFpYWNVSVHR | ITIM | TLR3_HUMAN | 733 |
| PSSpYHKLKSLM | ITIM | TLR1_HUMAN | 743 |
| YAPpYGNLLDFL | ITAM | TIE1_HUMAN | 922 |
| PLSpYPVLEWED | ITIM | TIE1_HUMAN | 831 |
| YSVpYSKLHPPA | ITAM | STAM2_HUMAN | 374 |
| LELpYNKLVNEA | ITAM | STAM2_HUMAN | 361 |
| YSMpYAKLQNQP | ITAM | STAM1_HUMAN | 384 |
| LSLpYTKLMNED | ITAM | STAM1_HUMAN | 371 |
| NTVpYSTVEIPK | ITSM | SLAF7_HUMAN | 304 |
| NTEpYDTIPHTN | ITSM | SLAF7_HUMAN | 284 |
| ITIpYSTINHSK | ITSM | SLAF6_HUMAN | 308 |
| NTVpYASVTHSN | ITSM | SLAF6_HUMAN | 284 |
| NLEpYVSVSPTN | ITIM | SLAF6_HUMAN | 273 |
| NTVpYSEVQFAD | ITSM | SLAF5_HUMAN | 316 |
| ITVpYASVTLPE | ITSM | SLAF1_HUMAN | 327 |
| LTIpYAQVQKPG | ITSM | SLAF1_HUMAN | 281 |

TABLE 2-continued

ITIM/ITAM/ITSM associated with human immunoreceptors

| Sequence | Type | UniProt ID | Tyr Postion |
|---|---|---|---|
| PVKpYSEVVLDS | ITIM | SIT1_HUMAN | 148 |
| DTEpYSEIKIHR | ITSM | SIGL9_HUMAN | 456 |
| ELQpYASLSFQM | ITIM | SIGL9_HUMAN | 433 |
| ELHpYATLSFHK | ITIM | SIGL8_HUMAN | 447 |
| EIQpYAPLSFHK | ITIM | SIGL7_HUMAN | 437 |
| DTEpYSEIKIHK | ITSM | SIGL6_HUMAN | 435 |
| ELHpYAVLHPHK | ITIM | SIGL6_HUMAN | 415 |
| TTEpYSEIKTSK | ITSM | SIGL5_HUMAN | 544 |
| ELHpYASLSFSE | ITIM | SIGL5_HUMAN | 520 |
| KVRpYRPVEGDP | ITIM | SIG1R_HUMAN | 313 |
| EIQpYASLSFHK | ITIM | SIG12_HUMAN | 565 |
| TTEpYSEIKIHT | ITSM | SIG11_HUMAN | 656 |
| ELHpYASLSFQG | ITIM | SIG11_HUMAN | 632 |
| ELHpYATLNFPG | ITIM | SIG10_HUMAN | 667 |
| ILDpYINVVPTA | ITIM | SIG10_HUMAN | 597 |
| FSEpYASVQVPR | ITIM | SHPS1_HUMAN | 495 |
| HTEpYASIQTSP | ITSM | SHPS1_HUMAN | 452 |
| DITpYADLNLPK | ITIM | SHPS1_HUMAN | 428 |
| VLVpYDKLNVKI | ITIM | ROR2_HUMAN | 624 |
| PVQpYNIVEQNK | ITIM | ROBO1_HUMAN | 1114 |
| STVpYGDVDLSN | ITSM | ROBO1_HUMAN | 1038 |
| HVSpYSAVSREN | ITIM | PVR_HUMAN | 398 |
| VLEpYVDLGDLK | ITIM | PTK7_HUMAN | 877 |
| GlVpYASLALSS | ITIM | PILRA_HUMAN | 269 |
| EQFpYNAIKRGY | ITAM | PGFRB_HUMAN | 914 |
| GTPpYPELPMNE | ITAM | PGFRB_HUMAN | 904 |
| NSLpYTTLSDVW | ITIM | PGFRB_HUMAN | 880 |
| VLSpYMDLVGFS | ITIM | PGFRB_HUMAN | 797 |
| SVLpYTAVQPNE | ITIM | PGFRB_HUMAN | 1009 |
| ETVpYSEVRKAV | ITSM | PECA1_HUMAN | 713 |
| DVQpYTEVQVSS | ITIM | PECA1_HUMAN | 690 |
| QTEpYATIVFPS | ITSM | PDCD1_HUMAN | 248 |
| SVDpYGELDFQW | ITIM | PDCD1_HUMAN | 223 |
| STDpYYRVGGHT | ITSM | NTRK2_HUMAN | 706 |
| STDpYYRVGGRT | ITSM | NTRK1_HUMAN | 680 |
| GVIpYSDLNLPP | ITIM | NKG2A_HUMAN | 8 |
| TEVpYACIENED | ITAM | NFAM1_HUMAN | 231 |
| ESVpYTALQRRE | ITAM | NFAM1_HUMAN | 220 |
| ESVpYTALQRRE | ITIM | NFAM1_HUMAN | 220 |
| EILpYHTVARTK | ITIM | NCTR2_HUMAN | 259 |
| PVLpYAMLDHSR | ITIM | MYP0_HUMAN | 220 |
| PVLpYAMLDHS | ITIM | MYP0_HUMAN | 219 |
| PVIpYAQLDHSG | ITIM | MPZL1_HUMAN | 241 |
| MTPpYPGVQNHE | ITSM | MERTK_HUMAN | 801 |
| YLLpYSRLETGP | ITIM | MERTK_HUMAN | 685 |
| ATIpYCSIRKPQ | ITSM | LY9_HUMAN | 626 |
| NTMpYAQVFNLQ | ITSM | LY9_HUMAN | 603 |
| PSTpYAHLSPAK | ITIM | LSR_HUMAN | 328 |
| QPVpYCNLQSLG | ITAM | LRC25_HUMAN | 284 |
| YINpYKDIDLAS | ITAM | LRC25_HUMAN | 273 |
| TVTpYVNLERLG | ITIM | LRC21_HUMAN | 571 |
| PSIpYAPLAIH | ITIM | LIRB5_HUMAN | 584 |
| DVTpYAQLHSFT | ITIM | LIRB4_HUMAN | 412 |
| AVTpYAKVKHSR | ITIM | LIRB4_HUMAN | 360 |
| AVTpYAPVKHSS | ITIM | LIRB3_HUMAN | 543 |
| PSIpYATLAIH | ITIM | LIRB2_HUMAN | 592 |
| ENLpYAAVKDTQ | ITIM | LIRB2_HUMAN | 533 |
| DVTpYAQLHSLT | ITIM | LIRB1_HUMAN | 614 |
| AVTpYAEVKHSR | ITIM | LIRB1_HUMAN | 562 |
| DLApYQTLPLRA | ITIM | LIME1_HUMAN | 235 |
| DVLpYSRVCKPK | ITIM | LIME1_HUMAN | 200 |
| FVKpYATLISNS | ITIM | LEPR_HUMAN | 986 |
| SIYpYLGVTSIK | ITIM | LEPR_HUMAN | 1079 |
| QVPpYLRVTVMP | ITIM | LAX1_HUMAN | 71 |
| SSDpYENVLTAK | ITIM | LAX1_HUMAN | 373 |
| VTSpYPPLSQPD | ITSM | LAT_HUMAN | 71 |
| SITpYAAVARH | ITIM | LAIR1_HUMAN | 281 |
| EVTpYAQLDHWA | ITIM | LAIR1_HUMAN | 251 |
| ATApYGLIKSDA | ITSM | KIT_HUMAN | 609 |
| SSGpYAQLNTYS | ITIM | KIRR1_HUMAN | 647 |
| TSVpYTELPNAE | ITIM | KI3L2_HUMAN | 428 |
| TILpYTELPNAK | ITIM | KI3L1_HUMAN | 428 |
| EVTpYAQLDHCV | ITIM | KI2LB_HUMAN | 298 |
| EVTpYAQLDHCI | ITIM | KI2L4_HUMAN | 300 |
| EVTpYAQLNHCV | ITIM | KI2L3_HUMAN | 303 |

TABLE 2-continued

ITIM/ITAM/ITSM associated with human immunoreceptors

| Sequence | Type | UniProt ID | Tyr Postion |
|---|---|---|---|
| IIVpYAELPNAE | ITIM | KI2L2_HUMAN | 332 |
| EVTpYTQLNHCV | ITIM | KI2L1_HUMAN | 302 |
| YLSpYTKVDQDT | ITIM | IRPL2_HUMAN | 408 |
| YLSpYTKVDPDQ | ITIM | IRPL1_HUMAN | 411 |
| ESKpYVSLITSY | ITIM | INGR1_HUMAN | 304 |
| TVQpYSTVVHSG | ITIM | IL6RB_HUMAN | 759 |
| GlVpYSALTCHL | ITIM | IL4RA_HUMAN | 713 |
| DSCpYDFLPIKA | ITIM | IL1R1_HUMAN | 372 |
| LVQpYKAVKETK | ITIM | IL1AP_HUMAN | 503 |
| VLFpYRHLTRRD | ITIM | IL18R_HUMAN | 359 |
| ESTpYLPLTSMQ | ITIM | ICAM3_HUMAN | 527 |
| SLLpYADLDHLA | ITIM | G6B_HUMAN | 212 |
| VNPpYPGlPVDA | ITAM | FLT3_HUMAN | 889 |
| GSPpYPGVPVEE | ITIM | FGFR1_HUMAN | 701 |
| GVVpYSVVHRTS | ITIM | FCRL6_HUMAN | 371 |
| PIIpYSEVKVAS | ITIM | FCRL5_HUMAN | 954 |
| NVVpYSEVRIIQ | ITIM | FCRL5_HUMAN | 924 |
| DVVpYSQVWSMQ | ITIM | FCRL2_HUMAN | 474 |
| TITpYSLLMHPD | ITIM | FCG2B_HUMAN | 292 |
| KNIpYLTLPPND | ITAM | FCG2A_HUMAN | 304 |
| DGGpYMTLNPRA | ITAM | FCG2A_HUMAN | 288 |
| QETpYETLKHEK | ITAM | FCERG_HUMAN | 76 |
| DGVpYTGLSTRN | ITAM | FCERG_HUMAN | 65 |
| SATpYSELEDPG | ITAM | FCERB_HUMAN | 229 |
| DRVpYEELNIYS | ITAM | FCERB_HUMAN | 219 |
| KLLpYEHVTEVD | ITIM | ERMAP_HUMAN | 188 |
| HLKpYLYLVVSD | ITIM | EPOR_HUMAN | 454 |
| KSDpYCNLPLYA | ITIM | DSCL1_HUMAN | 1898 |
| SSTpYEELARAY | ITIM | DSCAM_HUMAN | 1811 |
| TVHpYQSVSQAT | ITIM | DSCAM_HUMAN | 1708 |
| KVPpYTPLLSQP | ITIM | DCC_HUMAN | 1363 |
| CLPpYLGVSHQW | ITIM | CXCR6_HUMAN | 311 |
| KTQpYNQVPSED | ITSM | CXAR_HUMAN | 318 |
| QVLpYGQLLGSP | ITIM | CSF3R_HUMAN | 752 |
| LNPpYPGlLVNS | ITAM | CSF1R_HUMAN | 856 |
| ELHpYASVVFDS | ITIM | CM35H_HUMAN | 267 |
| EVEpYSTVASPR | ITIM | CM35H_HUMAN | 255 |
| ELHpYANLELLM | ITIM | CM35H_HUMAN | 231 |

TABLE 2-continued

ITIM/ITAM/ITSM associated with human immunoreceptors

| Sequence | Type | UniProt ID | Tyr Postion |
|---|---|---|---|
| DISpYASLTLGA | ITIM | CLM1_HUMAN | 249 |
| EDGpYTQLHFDS | ITAM | CLC7A_HUMAN | 15 |
| EITpYAEVRFKN | ITIM | CLC4A_HUMAN | 7 |
| ASIpYEELLKHD | ITIM | CEAM3_HUMAN | 230 |
| EVTpYSTLNFEA | ITIM | CEAM1_HUMAN | 493 |
| ESIpYEVLGMQQ | ITIM | CEA20_HUMAN | 578 |
| SSGpYSHLHHKV | ITIM | CDON_HUMAN | 1046 |
| MVDpYTTLSGAS | ITIM | CDON_HUMAN | 1019 |
| TATpYEDIVTLR | ITAM | CD79B_HUMAN | 207 |
| ENLpYEGLNLDD | ITAM | CD79A_HUMAN | 191 |
| AITpYADLRFVK | ITIM | CD72_HUMAN | 7 |
| EITpYENVQVPA | ITIM | CD72_HUMAN | 39 |
| LSApYPALEGVL | ITIM | CD5_HUMAN | 465 |
| ELKpYRVVSWFS | ITIM | CD47_HUMAN | 131 |
| REEpYDVLDKRR | ITAM | CD3Z_HUMAN | 83 |
| APApYQQGQNQL | ITAM | CD3Z_HUMAN | 64 |
| KDTpYDALHMQA | ITAM | CD3Z_HUMAN | 153 |
| DGLpYQGLSTAT | ITAM | CD3Z_HUMAN | 142 |
| AEApYSEIGMKG | ITAM | CD3Z_HUMAN | 123 |
| EGLpYNELQKDK | ITAM | CD3Z_HUMAN | 111 |
| DDQpYSHLQGNQ | ITAM | CD3G_HUMAN | 171 |
| DQLpYQPLKDRE | ITAM | CD3G_HUMAN | 160 |
| RDLpYSGLNQRR | ITAM | CD3E_HUMAN | 199 |
| NPDpYEPIRKGQ | ITAM | CD3E_HUMAN | 188 |
| DQVpYQPLRDRD | ITAM | CD3D_HUMAN | 149 |
| ELHpYASLNFHG | ITIM | CD33_HUMAN | 340 |
| STIpYEVIGKSQ | ITSM | CD244_HUMAN | 342 |
| YTLpYSLIQPSR | ITSM | CD244_HUMAN | 317 |
| STIpYSMIQSQS | ITSM | CD244_HUMAN | 297 |
| LTIpYEDVKDLK | ITSM | CD244_HUMAN | 271 |
| GlHpYSELIQFG | ITIM | CD22_HUMAN | 822 |
| TVTpYSALHKRQ | ITIM | CD22_HUMAN | 796 |
| GlSpYTTLRFPE | ITIM | CD22_HUMAN | 762 |
| PSLpYAQVQKPP | ITIM | CADH6_HUMAN | 685 |
| DVDpYDFLNDWG | ITIM | CADH5_HUMAN | 755 |
| GCEpYFVLAPHR | ITAM | BTNL9_HUMAN | 430 |
| EHLpYFTLNPRF | ITAM | BTNL8_HUMAN | 388 |

TABLE 2-continued

ITIM/ITAM/ITSM associated with human immunoreceptors

| Sequence    | Type | UniProt ID  | Tyr Postion |
|-------------|------|-------------|-------------|
| SLIpYTLLTCQF | ITIM | BTNL3_HUMAN | 430 |
| PTEpYASICVRS | ITSM | BTLA_HUMAN  | 282 |
| GlVpYASLNHSV | ITIM | BTLA_HUMAN  | 257 |
| ISFpYNAVDGSH | ITIM | BT3A1_HUMAN | 474 |

The term "peptide" or "polypeptide" as used herein is defined as a chain of amino acid residues, connected by peptide bonds and usually having a defined sequence. As used herein, the term "peptide" or "polypeptide" may, but need not, refer to a chain of amino acid residues without any N-terminal and/or C-terminal amino acid residues. That is, a "peptide" or "polypeptide" as used herein may refer to a chain of amino acids embedded within a longer chain of amino acids. As used herein the term "peptide" is inclusive of the terms "polypeptides", "peptides" and "proteins".

"pTyr-including peptide" refers to a peptide as defined above in which one of the amino acid residues is phosphorylated tyrosine. A "Tyr phosphosite" refers to the tyrosine residue within a peptide, such as a substrate of a tyrosine kinase, including the activation loop Tyr residue in a tyrosine kinase and ITRM, that is the target of kinase activity and which can thus be phosphorylated. A protein may have one or more Tyr phosphosites. As understood in the art, the identity of a Tyr phosphosite, and thus the identity of the pTyr-including peptides that correspond to such Tyr phosphosite in a sample, is imparted by the amino acid sequences flanking the Tyr phosphosite. As the term is used herein, identifying pTyr-including peptides refers to identifying the unique Tyr phosphosite to which a set of pTyr-including peptides corresponds to, which may include using targeted MS techniques.

SH2 domains are a family of protein domains that are understood in the art to recognize and bind to pTyr-including peptides, and have a known SH2 structural fold. As the term is used herein, SH2 domain refers to any naturally occurring or engineered polypeptide identified or understood as an SH2 domain by those in the art, including polypeptides that have a high degree of sequence similarity or sequence identity with a known SH2 domain. A high degree of sequence identity with a known SH2 domain may be 50% or higher, 55% or higher, 60% or higher, 65% or higher, 70% or higher, 75% or higher, 80% or higher, 85% or higher, 90% or higher, 95% or higher, 96% or higher, 97% or higher, 98% or higher, or 99% or higher.

As defined herein, a variant SH2 domain is an SH2 domain that is based on a known sequence of a known SH2 domain (also referred to as a reference SH2 domain or a parent SH2 domain for the particular variant SH2 domain) but which has specific positions within the SH2 domain substituted compared to the known sequence of the known SH2 domain. Thus, a variant SH2 domain has one or more positions in its sequence in which the amino acid has been substituted for a different amino acid as compared to the known SH2 domain from which the variant SH2 domain varies. Accordingly, any particular variant SH2 domain is defined relative to a specific known SH2 domain, and one variant SH2 domain is not necessarily relative to the same known SH2 domain as a different variant SH2 domain.

A parent SH2 domain may be any polypeptide identified as an SH2 domain in the biomedical literature that is used as the starting sequence for a variant, prior to the substitutions being made. In some embodiments, a parent SH2 domain may be a naturally occurring SH2 domain, including a naturally occurring wild type SH2 domain. In some embodiments, the parent SH2 domain may be an engineered SH2 domain having a designed sequence not known to naturally occur.

The variant SH2 domain may have one, two, three, four, five, six, seven, eight, nine or ten, or one or more, two or more, three or more, four or more, five or more, six or more, seven or more, eight or more, nine or more, or ten or more positions that vary as compared to the parent SH2 domain. The positions of the amino acid substitutions may occur within the pTyr binding pocket, the specificity binding pocket, or another region of the SH2 domain. The variant SH2 domain may possess at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% sequence identity with the known SH2 domain from which it varies.

Variant SH2 domains include triple mutants, quadruple mutants and SH2 Superbinders as defined herein.

Variant SH2 domains with three particular amino acid substitutions at three particular amino acid positions in the pTyr-binding pocket are referred to as triple mutant (TrM) SH2 domain variants herein. Variant SH2 domains that, in addition to the three substitutions within the pTyr-binding pocket, have a fourth amino acid substitution within the specificity binding pocket are referred to as a quadruple mutant (QuadM), For example, a TrM SH2 domain variant from the human Src protein that has an additional mutation (Thr218Trp) in its specificity-binding pocket is referred to as the QuadM Src SH2 domain herein.

A variant SH2 domain may be, in some embodiments, a recombinant SH2 domain, designed to have a specific set of amino acid substitutions relative to its parent domain, and produced, for example, using genetic engineering techniques.

Thus, in the method, in order to profile protein tyrosine phosphorylation, including protein kinase activity or immunoreceptor phosphotyrosine signalling, within a sample, the sample is contacted with a variant SH2 domain that is an SH2 Superbinder.

The sample may be any sample for which a profile of protein tyrosine phosphorylation, including a profile of protein kinase activity or immunoreceptor phosphotyrosine signalling, is desired to be obtained. Thus, the sample may be any sample that contains biological material and which contains or is suspected to contain an active protein kinase or peptides modified by an active protein kinase such as pTyr-including peptides, including within kinases such as kinase activation loops, within phosphatase regulatory regions, within ITRMs, and within downstream targets of kinases and phosphatases.

The sample may include but is not limited to: an established cell line; a cell culture, including a primary cell culture; a biological fluid such as serum, plasma, urine, or blood; a tissue sample; or a tissue extract. The sample may be human or non-human in origin, or may contain human or non-human protein kinase activity or human or non-human pTyr-including peptides.

The sample may be any sample that can be obtained by invasive or non-invasive techniques from a subject, which may or may not be a human being. Such samples may be obtained by any standard method known in the art, e.g., a finger stick blood sample, a buccal swab, a biopsy including from a tumour, a tape strip, and so forth. The sample may be normal sample (for example, healthy or non-diseased) or a diseased sample (for example a sample taken from a tumor or from a subject suffering from a disease such as cancer, a brain disease including Alzheimer's disease, a viral infection, or any other disease, or a subject suspected of suffering from such a disease). The sample may be from a biopsy of a tumour, including a tumour that may be suspected of having metastasized from a different location than the biopsy site.

The sample may be a sample that has been exposed to a drug treatment for disease, including a combination drug treatment, including exposed to one or more kinase inhibitors or phosphatase inhibitors, or may be free from exposure to such treatment.

Prior to the contacting, the sample may be treated in order to increase the binding of the SH2 Superbinder to any pTyr-including peptides within the sample. The sample may be treated to lyse cells contained in the sample, and to otherwise preserve pTyr-including peptides during the method. The sample may be perturbed by activation or inhibition with a signalling molecule, including for example PDL1, CD28 or TCR stimulation.

For example, the sample may be treated with one or more proteases in order to digest full length proteins to yield shorter pTyr-including peptides, for example treated with and endopeptidase such as trypsin. If necessary, the protease may be inhibited or inactivated prior to contacting the treated sample with the SH2 Superbinder.

In another example, the sample may be treated with a phosphatase inhibitor in order to prevent degradation of the pTyr within the pTyr-including peptides prior to contacting with the SH2 Superbinder.

In order to perform the profiling, the sample is contacted with an SH2 Superbinder.

Herein, the term SH2 Superbinder, or Superbinder, refers to a variant SH2 domain that comprises one or more amino acid substitutions in the pTyr-binding pocket, which substitutions result in the SH2 Superbinder having increased affinity for a pTyr residue or a pTyr residue located within a pTyr-including peptide, as compared to the parent SH2 domain from which the SH2 Superbinder varies and that does not have such substitution(s). In general, the affinity of a SH2 Superbinder is increased by about 10-fold or more relative to the parent SH2 domain, including by about 20-fold or more, by about 30-fold or more, by about 40-fold or more, by about 50-fold or more, by about 100-fold or more, by about 200-fold or more, by about 300-fold or more, or by about 500-fold or more.

The relative affinity of a variant SH2 domain, including a SH2 Superbinder, can be readily assessed compared to the affinity of the relevant parent SH2 domain, using binding assays known in the art, including as described in Kaneko, T. et al., "SH2 Superbinders act as antagonists of cell signaling", (2012) Sci. Signal. 5: ra68; and U.S. patent application Ser. No. 14/388,592.

SH2 Superbinders include single, double, triple, or quadruple mutant SH2 domains from the human proteins Src, Grb2, and Fyn. For example, the following are SH2 Superbinders: (i) a TrM human Src SH2 domain variant that has substitutions at Thr183Val (position 1), Cys188Ala (position 2), and/or Lys206Leu (position 3) (amino acid number is relative to the full-length wild-type human Src protein provided as SEQ ID NO:1); (ii) a TrM human Src SH2 domain variant that has substitutions at all three of the said positions above; (iii) a human Grb2 SH2 domain variant that has substitutions at Ala91Val (position 1), Ser96Ala (position 2), and/or Lys109Leu (position 3) (amino acid number is relative to the full-length wild-type human Grb2 protein provided as SEQ ID NO: 2); (iv) a TrM human Grb2 SH2 domain variant that has substitutions at all three of the said positions above; (v) a human Fyn SH2 domain variants that has substitutions at Thr181Val (position 1), Ser186Ala (position 2), and/or Lys204Leu (position 3) (amino acid number is relative to the full-length wild-type human Fyn protein provided as SEQ ID NO: 3); and (vi) a human Fyn SH2 domain variant that has substitutions at all three of the said positions above. All of these variant SH2 domains have been previously demonstrated to have a greatly increased affinity for pTyr-including peptides relative to the parent SH2 domains.

SH2 Superbinders may also include TrM variants of any other parent SH2 domain, meaning that the TrM SH2 domain at positions 1 through 3 has the same amino acids as are found in TrM human Src SH2 domain at positions 1 through 3, with positions 1 through 3 being discoverable by aligning the sequences of the parent SH2 domain and the wild-type human Src SH2 domain. As the structure of the SH2 domain family is conserved, it can be expected that making the same three substitutions in the homologous positions in other SH2 domains will also markedly increase their affinity for pTyr-including peptides.

In particular, SH2 Superbinders may include a TrM variant wherein the parent SH2 domain is a naturally-occurring peptide, such as a peptide encoded by the human genome, and the resulting SH2 Superbinder has a high degree of sequence similarity or sequence identity to that naturally-occurring peptide. A high degree of sequence similarity or sequence identity to the naturally-occurring parent peptide may be 50% or higher, 60% or higher, 70% or higher, 75% or higher, 80% or higher, 85% or higher, 90% or higher, 91% or higher, 92% or higher, 93% or higher, 94% or higher, 95% or higher, 96% or higher, 97% or higher, 98% or higher, or 99% or higher.

SH2 Superbinders may be based on a single, double, triple substitution within the pTyr-binding pocket, including TrM variants, but may further comprise one or more additional substitutions, including outside of the pTyr-binding pocket, which additional substitutions may or may not have any effect on binding affinity for pTyr-including peptides as compared to an SH2 Superbinder variant's increased affinity without such additional substitutions. In addition to the substitutions that define the SH2 Superbinder, for example the substation(s) in the pTyr-binding pocket, and in the case of a QuadM, the additional substitution in the specificity binding pocket, the Superbinder may have an additional one or more, two or more, three or more, four or more, five or more, six or more, seven or more, eight or more, nine or more, or ten or more amino acid substitutions relative to the parent SH2 domain in addition to the substitutions that define the SH2 Superbinder.

That is, for example, an SH2 Superbinder may be a variant SH2 domain having 3 substitutions defined for a TrM SH2 Superbinder, and may have at least the same increased affinity for pTyr-including peptides as the TrM SH2 Superbinder as compared to the parent, and may yet include an additional one or more amino acid substitutions relative to the parent SH2 domain in addition to the three substitutions that define the TrM variant SH2 Superbinder. In some embodiments, such additional substitutions may reduce the TrM variant SH2 Superbinder's affinity as compared to the TrM variant without such substitutions, but still yield an SH2 Superbinder having increased pTyr binding affinity as compared to the parent SH2 domain as defined herein.

Thus, an SH2 Superbinder may comprise, consist, or consist essentially of 3 defined substitutions in the pTyr-binding pocket (i.e. of a TrM), or may comprise, consist, or consist essentially of 3 defined substitutions in the pTyr binding pocket and one defined substitution in the specificity-binding pocket (i.e. of a QuadM). As used herein, consisting essentially of means that the Superbinder may have, in addition to the defined 3 or 4 substitutions, one or more, two or more, three or more, four or more, five or more, six or more, seven or more, eight or more, nine or more, ten or more, or from one to ten, or from one to five, additional amino acid substitutions relative to the parent SH2 domain, any of which additional substitutions may be within the pTyr-binding pocket, the specificity binding pocket, or another region of the SH2 domain, provided that the additional amino acid substitutions do not affect the increased affinity of the Superbinder compared to the parent SH2 domain and the percent sequence identity relative to the parent is at least 30%.

The SH2 Superbinder may comprise or may consist of the sequence as set out in SEQ ID NO: 5, 7, 9, 12 or 14.

SH2 Superbinders may include other variant SH2 domains identified in U.S. patent application Ser. No. 14/388,592, which is fully incorporated herein by reference.

Substitutions in a parent SH2 domain that result in a corresponding SH2 Superbinder can also be discovered by means known to those of skill in the art, including by phage display screening of a library of variant SH2 domains created by randomly substituting one or more of 15 amino acid residues that form the pTyr-binding pocket in a parent SH2 domain with one of the 20 naturally-occurring amino acids, as described in U.S. patent application Ser. No. 14/388,592.

Sequence identity between peptides can be determined by comparing a position in each sequence of amino acid residues which have been aligned for purposes of comparison. The sequence identity between sequences is the proportion of matching positions shared by the sequences in the alignment. As will be understood by those skilled in the art, two or more amino acid sequences can be aligned by well-known, standard algorithms that seek to maximize aspects of amino acid identity and/or similarity to achieve an optimal or preferred alignment.

As will be appreciated, the parent SH2 domain for an SH2 Superbinder may be an SH2 domain from eukaryotes other than humans including mammals, from viruses, as well as artificially-made sequences.

As an example of a parent SH2 domain from other eukaryotes, a parent SH2 domain may be part of a protein that is a homolog of the human Src protein (SEQ ID NO: 1), the human Grb2 protein (SEQ ID NO: 2), the human Fyn protein (SEQ ID NO: 3), or any other human protein that includes an SH2 domain as identified in the biomedical literature, where the homolog is encoded by a gene or genome of any eukaryote, animal, or mammal. It will be appreciated and understood that a parent SH2 domain need not be that encoded by a naturally-occurring gene or genome, but can include SH2 domains with amino acid substitutions that do not affect affinity for pTyr-including peptides.

As an example of a parent SH2 domain from a virus, a parent SH2 domain may be v-Src, encoded by the Rous Sarcoma virus, which is a viral homolog of human Src.

As an example of a parent SH2 domain that is an artificially-made sequence, as would be appreciated by a person of skill in the art, one could design an SH2 domain sequence by combining the sequences of one or more mammalian SH2 domain sequences, which may represent a consensus or quintessential SH2 domain sequence, but would not be identical to any mammalian SH2.

It will also be appreciated and understood that a SH2 Superbinder can be part of a larger polypeptide that includes amino acids which form an affinity tag, such as a hexahistidine ($His_6$) tag, a glutathione-S-transferase (GST) tag, a FLAG tag, and the like. For example, the SH2 Superbinder may comprise or may consist of the sequence as set out in SEQ ID NO: 11 or 13.

More than one SH2 Superbinder can be used to contact the sample and thus perform the profiling. As will be appreciated by a person skilled in the art, using more than one SH2 Superbinder in the method as an affinity reagent for the pTyr-including peptides may allow for better coverage of the Tyr phosphoproteome by reducing or eliminating any bias in the population of enriched pTyr-including peptides that might result from the sequence specificity of individual SH2 Superbinders.

Similarly, an SH2 Superbinder can have substitutions in amino acids in the specificity pocket that may reduce, eliminate, or alter the sequence specificity for C-terminal residues in the ligand peptide. An example is the aforementioned QuadM Src SH2 domain variant, as further discussed in the Examples.

Alternatively, a protein may be designed to contain multiple SH2 domains, in which at least one of them is a SH2 Superbinder. For example, a protein that comprises multiple SH2 Superbinders, each of which targets different pTyr-including peptides, may be designed and created. Use of an SH2 Superbinder in a multi-SH2 domain construct may further increase binding affinity toward a particular target protein, including one that contains multiple pTyr residues in a single polypeptide molecule. In such constructs, the SH2 domains could be connected by a flexible linker, preferably a polypeptide that contains glycine. Variation of the linker length and composition may modulate the binding affinity of a multi-SH2 domain protein. A multi-SH2 domain protein may have increased affinity to a multi-pTyr region such as the Immunoreceptor Tyrosine-based Activation Motif (ITAM) motif of a single protein. A multi-SH2 domain protein may also serve to bridge multiple proteins through pTyr sites in target proteins. The methods of the present disclosure thus include all such novel proteins comprising multiple SH2 domains, at least one of which is a Superbinder.

A protein may also be designed to include one or more SH2 Superbinders and other modular protein domains, such as other pTyr-binding domains (e.g., PTB domains), pSer/pThr-binding domains (e.g., certain 14-3-3 and WD40 domains), and ubiquitin-binding domains. The methods of the present disclosure thus include all such novel proteins.

The SH2 Superbinder may thus comprise or may consist of the sequence as set out in SEQ ID NO: 15.

The SH2 Superbinders of the present disclosure may be synthesized by any known method in the art of peptide synthesis including solid phase synthesis (Merrifield, *J. Am. Chem. Assoc.* 65:2149 (1964); *J. Amer. Chem. Soc.* 85:2149 (1963); and *Int. J. Peptide Protein Res.* 35:161-214 (1990)) or synthesis in homogenous solution (*Methods of Organic Chemistry*, E. Wansch (Ed.), Vol. 15, pts. I and II, Thieme, Stuttgart (1987)) to generate synthetic peptides.

Alternatively, and more simply, the variant SH2 domains of the disclosure can be made with standard recombinant DNA techniques. For instance, E. coli can be transformed with a plasmid encoding an affinity-tagged SH2 Superbinder, high-level expression of the SH2 Superbinder can be induced, and the SH2 Superbinder can be purified from E. coli cell lysate with an affinity reagent corresponding to the affinity tag.

In the method, in order to obtain the profile, the SH2 Superbinder is contacted with the sample.

The SH2 Superbinder may be contacted with the sample at, or below, a saturating amount or concentration.

As would be understood by those skilled in the art, a saturating amount or concentration of SH2 Superbinder refers to the lowest amount of SH2 Superbinder, within the volume of solution in which the binding reaction with pTyr-including peptides takes place, at which the greatest or near-greatest number of pTyr-including peptides are enriched, as later determined by identification and quantification of those peptides. That is, as the amount of SH2 Superbinder in the binding reaction is increased, it would be expected that the number of pTyr-including peptides bound by that SH2 Superbinder (and later identified and quantitated) would increase, up until a point at which all or nearly all of the pTyr-including peptides capable of being bound by that SH2 Superbinder are so bound. At this point, the amount of SH2 Superbinder is said to be saturating. It will be further appreciated that any amount of SH2 Superbinder higher than the saturating amount or concentration is also a saturating amount or concentration.

The saturating amount or concentration for a given assay can readily be determined by a person of ordinary skill in the art using routine laboratory methods, including employing standard binding curves using increasing concentrations of the SH2 Superbinder for a known amount of a certain sample type.

Subsequent to contacting the sample with the SH2 Superbinder, the method involves removing or isolating any pTyr-including peptides that are now bound to the SH2 Superbinder from the sample, followed by identifying the pTyr-including peptides thus removed from the sample.

Thus, in the method, the purified SH2 Superbinder can be used to isolate the pTyr-including peptides contained within the sample for identification, thus enriching the pTyr-including peptide fraction. The isolation may be performed using techniques well-known to those of skill in the art, including for example liquid chromatography methods, including high performance or ultra performance liquid chromatography, immunoprecipitation methods, size exclusion methods, and mass spectrometry.

For ease of separation from the remaining sample contents, the SH2 Superbinder may be immobilized on a solid support in order to assist with isolation and identification of the pTyr-including peptides from the sample.

As used herein the terms "solid support", "matrix", and "resin" refer to and include any support capable of binding the affinity reagents disclosed herein. Well known supports or carriers include glass, polystyrene, polypropylene, polyethylene, dextran, nylon, amylases, natural and modified celluloses, sepharose, polyacrylamides, and magnetite. The support material may have virtually any possible structural configuration so long as the coupled affinity reagent is capable of binding to peptides and/or proteins. Thus, the support configuration may be spherical, as in a bead, or cylindrical, as in the inside surface of a test tube, or the external surface of a rod. Alternatively, the surface may be flat such as a sheet, test strip, etc. The solid support may be sepharose or polystyrene beads. Those skilled in the art will know many other suitable carriers for binding affinity reagent, or will be able to ascertain the same by use of routine experimentation.

For instance, the SH2 Superbinder bound to a solid support, either covalently (e.g., via cross-linking or direct coupling) or non-covalently (e.g., via an affinity tag), can be contacted with a mixture of peptides that had been obtained from the biological sample and dissolved in a suitable buffered solution. While SH2 Superbinders can be expected to bind to full-length proteins, it may be desirable to digest proteins from the biological sample with an endopeptidase (e.g., trypsin) prior to Superbinder enrichment. Once pTyr-including peptides have bound to the SH2 Superbinder, the solid support is removed from the peptide solution and washed one or more times with appropriate wash solutions. The pTyr-including peptides that remain bound to the SH2 Superbinder are then eluted, separated from the Superbinder, and optionally further enriched using another affinity reagent (e.g., IMAC). As will be appreciated, for the steps of binding, washing, and eluting, the SH2 Superbinder bound to the solid support can be in a column. Alternatively, the solid support can be free in the various solutions and can be isolated by centrifugation during, for example, the washing and elution steps.

Once isolated from the remaining sample via binding with the SH2 Superbinder, the pTyr-including peptides can be identified, and optionally quantified, with any methods known in the art, which methods may include appropriate types of mass spectrometry, which may also be preceded by one-dimensional (1D) or two-dimensional (2D) liquid chromatography (LC).

The identification technique may be selected, in part, depending on the set of pTyr-binding peptides that are to be identified and optionally quantified.

For example, profiling mass spectrometry techniques may be used to identify and optionally quantify a broad set of pTyr-binding peptides, including a set that contains all or essentially all detectable pTyr-binding peptides from the sample.

In another example, targeted mass spectrometry techniques may be used to identify and optionally quantify a specific set of pTyr-binding peptides, including a set that contains a defined subset of all detectable pTyr-binding peptides from the sample, for example a set that targets pTyr-binding peptides from one or more specific kinases, including within the activation loop or outside the activation loop, including a positive regulatory region or a negative regulatory region. The set may include pTyr-including peptides from one or more immunoreceptors, including one or more ITRMs, for example from an ITIM, and ITAM or an ITSM. The set may include pTyr-including peptides from one or more particular protein tyrosine phosphatase, including from a regulatory region, including a positive regulatory region or a negative regulatory region. The set may include pTyr-including peptides from one or more downstream target substrates of a kinase, or one or more downstream target substrates of a protein tyrosine phosphatase.

The set may include pTyr-including peptides associated with positive or negative responses to a given drug treatment or within kinases known to be inhibited by the drug treatment. The set may include pTyr-including peptides associated with a signalling pathway.

The set may include pTyr-including peptides from cellular or tissue markers, to allow for identification of the particular cell or tissue type from which cells in the sample originated. For example, the pTyr-including peptides may be from a cell or tissue type corresponding to the site of a biopsy, or may be from a cell or tissue type that is associated with a metastatic cancer, for example, breast, brain or lung tissue. The pTyr-including peptides may be associated with one or more immune cell types, including B cells, T cells, natural killer cells or macrophages.

Thus, as described below, the described methods may be further tailored or customized, including with respect to selection of the various described parameters.

A wide variety of mass spectrometry (MS) techniques are known in the art, see e.g., Mann et al., *Ann. Rev. Biochem.*, (2001) 70:437-473; Wissing et al., *Mol. Cell. Proteomics*, (2007) 6:537-547. Examples of MS techniques include: tandem MS (MS/MS) (Gerber et al., *Proc. Natl. Acad. Sci. U.S.A.*, (2003) 100: 6940-6945; WO 2006/134056); multiple reaction monitoring (MRM) (Hardt et al., 2008 Thermo Scientific Application note: 451, (2008); Kuhn et al., *Proteomics*, (2004) 4:11751186); parallel reaction monitoring (Peterson et al., *Mol. Cell. Proteomics*, (2012) 11:1475-1488); stable isotope labelling with amino acids in cell culture (SILAC) (US 2010/0279891; Daub et al., *Mol. Cell*, (2008) 31:438-448; Ong et al., *Mol. Cell. Proteomics*, (2002) 1:376-386); super SILAC, a spike-in mix for SILAC (Geiger et al., *Nat. Meth.*, (2010) 7:383-387; Geiger et al., *Nat. Prot.* (2011) 6:147-157; and titanium dioxide enrichment of phosphopeptides (Thingholm et al., *Nat. Prot.* (2006) 1: 1929-1935).

Using MS, relative quantification of phosphorylation may be obtained by label-free quantification of individual pTyr-including peptides by determining peak volume. Such quantification may further include a comparison to a constitutively phosphorylated pTyr-including peptide, such as site Tyr216 within the activation loop of GSK-3β (Cole, A. et al., "Further evidence that the tyrosine phosphorylation of glycogen synthase kinase-3 (GSK3) in mammalian cells is an autophosphorylation event", (2004) *Biochem. J.* 377:249-255; Hughes, K. et al., "Modulation of the glycogen synthase kinase-3 family by tyrosine phosphorylation", (1993) *EMBO J.* 12:803-808). In addition, absolute quantification may be achieved by spiking into the MS sample a predetermined amount of stable isotope-labelled peptides representing the phosphopeptides of interest (Gillette, M. A. and Carr, S. A., "Quantitative analysis of peptides and proteins in biomedicine by targeted mass spectrometry" (2013) *Nat. Methods* 10, 28-34).

In particular, a targeted MS technique such as MRM, SRM or Parallel Reaction Monitoring (PRM) can be used (Liebler, D. C. and Zimmerman, L. J., "Targeted quantitation of proteins by mass spectrometry" (2013) *Biochemistry* 52:3797-3806). MRM uses a predetermined list of daughter ions to detect a parent peptide. MRM is 1-2 orders of magnitude more sensitive than shotgun LC-MS/MS approaches (Picotti P. and Aebersold R., "Selected reaction monitoring-based proteomics: workflows, potential, pitfalls and future directions", (2012) *Nat. Methods* 9:555-566; Liu H. et al., "A method for systematic mapping of protein lysine methylation identifies functions for HP1beta in DNA damage response", (2013) *Mol. Cell* 50:723-735).

In addition to the sample to be profiled, the method may be performed using a control or a comparative sample, and the profile obtained for the test sample can be compared to the profile obtained for the control or comparative sample. The control or comparative sample may be designed as any appropriate positive or negative control for a given test sample, in keeping with standard laboratory methods.

For example, the control or comparative sample may be a sample obtained from a healthy individual or cell sample known to be free from a disease that is to be detected, or alternatively from a source known to have a specific disease or display a phenotype associated with a specific disease or disorder. The control sample may be from a particular cell or tissue type. The control or comparative sample may be a sample that has or has not been exposed to a drug or treatment regimen or a kinase or a phosphatase inhibitor, whereas the test sample may have the same or opposite treatment status as the control. The comparative or control sample may be obtained from the same source or subject as the test sample at a different time during a treatment regimen. The comparative or control sample may have a known kinase up-regulation or down-regulation for one or more specific kinases or protein tyrosine phosphatases, for example may be a sample from a cell known to have a mutation for a specific kinase or known to be transgenically expressing a specific kinase.

The binding affinity of the SH2 Superbinders may be combined with selected identification techniques and specific sample types to allow for use of the methods disclosed herein in a variety of different applications or analyses. For example, and as described herein, the profiling may be varied by specifically selecting: the type of test sample and/or control sample used, including the conditions the test sample and/or control sample have been exposed to prior to use in the method, the specific identification and optional quantification techniques used, and the specific set of pTyr-including peptides to be identified. Varying these parameters can result in different profiles, suitable for different applications or analyses. All such variations and embodiments are within the scope of the present disclosure.

Thus, profiling the phosphotyrosine signalling activity within a sample using the methods described herein could be used to provide insight into any cell state, including any disease state. Given the importance of TKs in human cancers, as well as tumor response to therapies, including TK-targeted therapies and immunotherapies, the methods of the present disclosure may be particularly useful in the research, diagnosis, prognosis, and therapy of human cancers.

The following described variations of the disclosed methods are illustrative.

The method may be a method of profiling protein tyrosine phosphorylation of a test sample, the method comprising: contacting the test sample with a saturating amount of an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a profiling MS technique, so as to identify and optionally quantify all or essentially all of the pTyr-binding peptides that are detectable in the isolated fraction.

The method may be a method of profiling a subset of protein tyrosine phosphorylation of a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a targeting MS technique, so as to identify and optionally quantify a subset of the pTyr-including peptides that are detectable in the isolated fraction. The subset may comprise, for example, pTyr-including peptides from one or more kinase activation loops, one or more ITRMs, or one or more regulatory regions of a protein tyrosine phosphatase. The contacting may comprise using a saturating amount, or an amount below a saturating amount, of the SH2 Superbinder. The MS technique may comprise PRM, SRM and/or MRM MS techniques. The test sample may be from a source of healthy cells or tissues, or a source of diseased cells or tissues including cells or tissued known to have or be involved in cancer, Alzheimer's disease or to be infected with a virus.

By focussing the set of pTyr-including peptides that are identified and optionally quantified to those that are located within the activation loop of a kinase, including TKs, STKs, dual specificity kinases, MAP kinases and lipid kinases, it is possible to thus profile kinase activity within the sample.

For instance, profiling TK activity could identify TKs that drive the proliferation, spread, or drug resistance of cancerous cells. Such cancer drivers may in turn prove to be effective targets for pharmacologic interventions. Such profiling may provide a particular advantage as a means to reduce or avoid resistance to cancer therapies. While TK-targeted therapies often exhibit short-term benefits to patients, resistance can quickly arise. The mechanisms of resistance vary, but the activation of non-targeted tyrosine kinases is a common cause of resistance to both conventional and TK-targeted therapies (Holohan, C. et al., "Cancer drug resistance: an evolving paradigm", (2013) *Nature Reviews Cancer* 13:714-726). In general, aberrant tyrosine kinases stimulate cell proliferation and immortality via the MAPK and PI3K signaling pathways, which are key characteristics of many, if not all, cancer cells.

For conventional cancer therapeutics such as antimetabolites and topoisomerase inhibitors, increased activation of ErbB2 receptor tyrosine kinase may be responsible for resistance (Hurwitz, J. L. et al., "Vorinostat/SAHA-induced apoptosis in malignant mesothelioma is FLIP/caspase 8-dependent and HR23B-independent" (2012) *Eur. J. Cancer* 48:1096-1107; Wilson, T. R. et al., "Procaspase 8 overexpression in non-small-cell lung cancer promotes apoptosis induced by FLIP silencing" (2009) *Cell Death Differ.* 16:1352-1361).

When specifically targeting TKs, drug resistance is more common due to the functional redundancy and cross-activation among tyrosine kinases. As one example, the HER2 oncogene, which is diagnosed as ErbB2 over-activation, accounts for up to 30% of all breast cancers (Slamon, D. J. et al., "Human breast cancer: Correlation of relapse and survival with amplification of the HER-2/neu oncogene", (1987) *Science* 235:182-191). Trastuzumab (Herceptin®) is the first approved targeted therapeutic for this cancer type. However, around 70% patients with HER2-positive breast cancer have intrinsic resistance and do not respond to trastuzumab (Vogel, C. L. et al., "Efficacy and safety of trastuzumab as a single agent in first-line treatment of HER2-overexpressing metastatic breast cancer", (2002) *Journal of Clinical Oncology* 20:719-726). In addition, up to 70% of the patients who initially respond to trastuzumab suffer disease recurrence within one year of treatment (Gajria, D. and Chandarlapaty, S., "HER2-amplified breast cancer: mechanisms of trastuzumab resistance and novel targeted therapies", (2011) *Expert Rev. Anticancer Ther.* 11:263-275), suggesting a fast-developing acquired resistance.

Given the problem of acquired resistance, systematic evaluation of TK activities are important for understanding resistance mechanisms and designing combination therapies to overcome resistance. Such an approach has the potential to predict resistance well before recurrence of the tumor, to determine cancer prognosis and improve the effectiveness of a treatment regimen.

Profiling protein kinase activity or immune signalling activity may be useful in measuring, and enabling the potential development of novel assays for, immune cell function.

Such profiling may also provide useful information for patient stratification for targeted or immune therapies. For example, the presence of an activated TK could be used as a biomarker for the utilization of therapies targeting that TK; the presence of infiltrated T cells, which can be detected by identifying the phosphorylation of the CD3 subunits of the T cell receptor or other regulators of T cell signalling using the SAP-MRM or SAP-PRM method, would indicate a favourable response to an immunotherapy that is designed to increase T cell activity.

As one example, embodiments of the present disclosure may be useful in predicting and monitoring the response to therapies directed to Programmed Cell Death Protein 1 (PD-1) and its ligand PD-L1. Ligand binding (PD-L1) to PD-1 leads to phosphorylation of the latter on ITIM and ITSM Tyr residues which, in turn, recruit the SH2 domain-containing phosphatase 2 (SHP2) to dephosphorylate the TK ZAP-70, resulting in T cell inactivation. Blocking PD-1 with monoclonal antibodies will reverse this process, manifesting in decreased phosphorylation of the ITIM and ITSM Tyr in PD-1 and increased phosphorylation of the activation loop of ZAP-70 and TCR co-receptors. Monitoring the Tyr phosphorylation of the ITIM and ITSM of PD-1, ITAM sequences in TCR co-receptors, and the activation loop of ZAP-70 by needle tumor biopsy or by collecting circulating T cells could be used to: (i) evaluate the efficacy of an anti-PD-1 antibody therapy (e.g., decreased PD-1 ITSM/ITIM phosphorylation and increased TCR/ZAP-70 phosphorylation); (ii) predict patient response to anti-PD-1 antibody therapy and possibly stratify patients long before a phenotypic response is observed. These and related approaches may also involve monitoring cytokine signalling through the JAK1/STAT pathway, such as by quantifying JAK1/2/3, TYK1/2 and STAT1/2/3 Tyr phosphorylation.

Thus, as mentioned above, profiling may involve profiling of protein kinase activity. Such an embodiment may comprise identification and optional quantification of pTyr-including peptides from one or more kinases, including from the kinase activation loops or from outside the kinase activation loops of the one or more kinases, including from one or more kinases known to be involved in disease development or progression, such as cancer. In some embodiments, the sample used may be from a source or sample exposed to a drug treatment regimen for a specific disease, including for example cancer, or may be from a source or sample suspected of having or being involved in a specific disease or disorder, including cancer, or known to have or be involved in a specific disease or disorder, including cancer. The cancer may be any type of cancer, including for example breast cancer, lung cancer, prostate cancer or leukemia. Samples taken before and after treatment with a drug may be profiled and the profiles compared, to determine sensitivity or resistance of kinases within the sample to the drug used.

Thus, the method may be a method of profiling tyrosine kinase activity of a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides from the test sample using a targeting MS technique, which may comprise PRM, SRM and/or MRM MS techniques, so as to identify pTyr-including peptides within a kinase activation loop of a tyrosine kinase. The method may further comprise contacting a control sample with the SH2 Superbinder in order to bind pTyr-including peptides contained in the control sample with the SH2 Superbinder; isolating the bound pTyr-including peptides from the control sample; and identifying and optionally quantifying the isolated pTyr-including peptides from the control sample using the targeting MS technique so as to identify pTyr-including peptides within the kinase activation loop of the tyrosine kinase, and comparing the profile obtained for test sample with that obtained for the control sample. The test sample may be of diseased cells or tissues, including from a human subject suffering or suspected to suffer from the disease. Such diseased cells or tissues may include cells or tissues known to have or be involved in cancer, Alzheimer's disease or to be infected with a virus. The control sample may be obtained from healthy cells or tissues, or may be from the same source as the test sample. For example, comparing to a non-Alzheimer's disease sample or a sample not infected with a virus may be appropriate for a diagnosis or prognosis of this disease.

The method thus may be for diagnosis or prognosis of any disease associated with a change in tyrosine phosphorylation, including increased or decreased activation of a specific tyrosine kinase.

In different embodiments, the test sample may be treated with a kinase inhibitor, or with a drug known or to be tested for treatment of the disease, such as cancer and the control sample may differ from the test sample only in that it is free from such treatment. Such comparison, including over time, may indicate the efficacy of treatment, including over time, as assessed, for example by decreased tyrosine phosphorylation in the test sample.

The method thus may also be a method of detecting cellular response to a drug of a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides from the test sample using a targeting MS technique, which may comprise PRM, SRM and/or MRM MS techniques, so as to identify a subset of the pTyr-including peptides that are detectable in the isolated fraction. The subset may comprise pTyr-including peptides from one or more kinase activation loops, or one or more downstream target substrates of a kinase. The test sample may be obtained from a source of diseased cells or tissues. Such diseased cells or tissues may include cells or tissues known to have or be involved in cancer, Alzheimer's disease or to be infected with a virus, and may be a biopsy sample. The test sample may be treated with a kinase inhibitor or other regulatory inhibitor, or with a drug known or to be tested for treatment of the disease. In this way, the method may be used to detect suitable treatment options for a disease, or to detect development of resistance to treatment.

Thus, the method may also be a method of determining responsiveness to a drug treatment regimen, including resistance, the method comprising: contacting a test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides from the test sample using a targeting MS technique, which may comprise PRM, SRM and/or MRM MS techniques, so as to identify pTyr-including peptides associated with positive or negative responses to the drug treatment or within kinases known to be inhibited by the drug treatment. The test sample may be obtained from a source of diseased cells or tissues. Such diseased cells or tissues may include cells or tissued known to have or be involved in cancer, Alzheimer's disease or to be infected with a virus, including a biopsy sample. The test sample may be treated with one or more kinase inhibitor or one or more drug known or to be tested for treatment of the disease. In this way, it is possible to assess a subject's predicted response to a treatment regimen, and may be possible to identify a suitable drug or combination of drugs for treatment. Thus, the method may be a method for determining a treatment regimen, including a drug therapy or combination drug therapy. It is also possible to detect over time, kinase activation in cells that are resistant or become resistant to drug treatments, and to design further treatments to target kinases that become activated in response to an initial treatment regimen.

By focussing the set of pTyr-including peptides that are identified and optionally quantified to those that are located within an ITRM of an immunoreceptor, including an ITIM, an ITAM, or an ITSM, it is possible to thus profile regulation of immune responses within the sample.

Thus, as another example, embodiments of the present disclosure may be useful in providing a personalized approach to mitigate morbidity and reduce therapy interruptions resulting from a therapeutic blockade of Cytotoxic T-Lymphocyte-Associated Protein 4 (CTLA-4). Blocking CTLA-4 results in a high incidence of immune-related adverse events (irAEs), and it can be expected that this may be associated with Tyr phosphorylation of ITAM/ITIM/ITSM-bearing immunoreceptors or associated kinases that are affected by CTLA-4 inhibition.

Characterization of a subject's in situ immune cell responses with methods of the present disclosure before, during and after immunotherapy may also provide new diagnostic and prognostic insights. Characterization of responders and non-responders based on their immune signalling patterns via ITAM/ITIM/ITSM Tyr phosphorylation may enable more precise personalized approaches to optimize immunotherapy treatments.

Thus, profiling may involve profiling of immunoreceptor phosphtyrosine signalling. Such embodiments may comprise identification and optional quantification of pTyr-including peptides from one or more immunoreceptors, including from one or more ITRMs, each of which may be an ITIM, and ITSM or an ITAM, of one or more immunoreceptors. In some embodiments, the sample used may be from or comprise an immune cell, including a B cell, a T cell, a natural killer cell or a macrophage. In some embodiments, the ITRM is known to be involved in immunosignalling relating to disease development or progression, such as cancer. In some embodiments, the sample used may be from a source or sample exposed to a drug treatment regimen for a specific disease, including for example cancer, or may be from a source or sample suspected of having or being involved in a specific disease or disorder, including cancer, or known to have or be involved in a specific disease or disorder, including cancer. The cancer may be any type of cancer, including for example breast cancer, lung cancer, prostate cancer or leukemia. Samples taken before and after treatment with a drug may be profiled and the profiles compared, to determine sensitivity or resistance of the immunosignalling pathways within the sample to the drug used.

In some embodiments, profiling of protein kinase activity may be combined with profiling of immunoreceptor phosphtyrosine signalling by selecting the set of pTyr-including peptides that is identified and optionally quantified to including both pTyr-including peptides from one or more protein kinases and from one or more ITRMs.

In a further embodiment, protein kinase activity is profiled in a biological sample by identifying and optionally quantifying pTyr-including peptides in the sample corresponding to substrates of specific kinases, including one or more TKs, STKs or other dual-specificity kinases, MAP kinases, or lipid kinases. Some of the substrates of specific kinases are known and may be identified from the biomedical literature.

The substrates of specific kinases, for example TKs, may also be identified by a further, modified embodiment of the present disclosure by comparing the profile of pTyr-including peptides in a sample derived from biological material in which an activity of a specific TK or a specific family of related TKs had been perturbed, either pharmacologically and/or genetically, to the profile of pTyr-including peptides in a sample from biological material that was not subjected to such a perturbation (i.e. a control sample, such as from a healthy individual or cell source, or untreated individual or cell source).

Means of pharmacologically and/or genetically perturbing the activity of specific TKs are known to those of skill in the art and the following examples are only meant to be illustrative. The activity of a specific TK can be pharmacologically reduced by exposing cells to an inhibitor, such as a cell-permeable small molecule that is known to preferentially bind to the activation site of that specific TK. Many such small molecules have been identified in the literature, including many that have been approved by the FDA for use in patients. The activity of a specific receptor TK can be reduced by antibodies selected to bind the extracellular region of the receptor TK. Many humanized antibodies have been approved by the FDA for use in patients. The activity of a specific TK can be genetically reduced by suppressing, reducing or inhibiting the expression of that TK, including with RNAi, by expressing a dominant-negative version of that specific TK, or by knocking out all or a portion of the gene encoding that specific TK (e.g., using CRISPR/Cas9 technology). In particular, the activity of a specific TK can be reduced in a highly-specific manner by a chemical genetic strategy that replaces the alleles encoding that TK in a cell or organism with an altered-sensitivity allele (as-allele). The as-allele encodes a version of the TK that is inhibited in a highly-specific manner by a cell-permeable small molecule (Bishop, A. C. et al., "A chemical switch for inhibitor-sensitive alleles of any protein kinase", (2000) *Nature* 407:395-401).

By selecting the set of identified and optionally quantified pTyr-including peptides as those contained within a regulatory region of a protein tyrosine phosphatase, including a positive regulatory region or a negative regulatory region, the method may comprise a method of profiling protein tyrosine phosphatase activity in the sample.

Thus, in a further embodiment, protein tyrosine phosphatase (PTP) activity is profiled in a sample, by identifying and quantifying pTyr-including peptides in the sample corresponding to one or more regulatory regions of a PTP. As further discussed in the Examples, PTPs appear to comprise numerous regulatory pTyr residues. As will be appreciated by a person skilled in the art, the general approaches taken with TKs that are described above can be extended to PTPs, such as combining Superbinder-based purification and MRM or PRM in a targeted proteomics approach.

In a further embodiment, PTP activity is profiled in a sample, by identifying and quantifying pTyr-including peptides in the sample corresponding to substrates of specific PTPs. As will be appreciated by a person skilled in the art, the general approaches to profiling the substrates of specific TKs that are described above can be extended to profiling the substrates of specific PTPs, including first identifying such substrates with a phosphoproteomics-based analysis of the effects of pharmacologically and/or genetically perturbing the activity of specific PTPs or families of related PTPs.

Thus, the method may be a method of profiling protein tyrosine phosphatase activity of a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides from the test sample using a targeting MS technique, which may comprise PRM, SRM and/or MRM MS techniques, so as to identify pTyr-including peptides within a regulatory region of a protein tyrosine phosphatase, including a positive or negative regulatory region. The method may further comprise contacting a control sample with the SH2 Superbinder in order to bind pTyr-including peptides contained in the control sample with the SH2 Superbinder; isolating the bound pTyr-including peptides from the control sample; and identifying and optionally quantifying the isolated pTyr-including peptides from the control sample using the targeting MS technique so as to identify pTyr-including peptides within the regulatory region of the protein tyrosine phosphatase, and comparing the profile obtained for test sample with that obtained for the control sample. The test sample may be obtained from a source of diseased cells or tissues. Such diseased cells or tissues may include cells or tissued known to have or be involved in cancer, Alzheimer's disease or to be infected with a virus. The control sample may be obtained from healthy cells or tissues, or may be from the same source as the test sample. The test sample may be treated with a drug known or to be tested for treatment of the disease, and the control sample may be free from such treatment.

The profiling method may be further targeted or customized by selecting the set of pTyr-including peptides to include those from a kinase activation loop, for example of a tyrosine kinase, as well as those from a regulatory region of a protein tyrosine phosphatase, and optionally those from a downstream target of the kinase or the phosphatase. By selecting the set of pTyr-including peptides in this way, it is possible to attempt to map different regulatory pathways within a cell.

Thus, the method may be a method of characterising a signalling pathway in a cell, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a targeting MS technique, so as to identify and optionally quantify a subset of the pTyr-including peptides that are detectable in the isolated fraction. The subset may comprise pTyr-including peptides from one or more kinase activation loops, one or more regulatory regions of a protein tyrosine phosphatase, and one or more downstream target substrates of the kinase and/or the protein tyrosine phosphatase. The contacting may comprise using a saturating amount, or an amount below a saturating amount of the SH2 Superbinder. The MS technique may comprise PRM, SRM and/or MRM MS techniques.

In a further embodiment, post-translational amino acid modifications (PTMs) in addition to pTyr that are present in the pTyr-including peptide are identified and quantified. Such PTMs may further indicate the activity state of a Tyr-phosphorylated kinase. As will be appreciated by those skilled in the art, identifying such PTMs may involve enriching pTyr-including peptides that have not been subjected to protein digestion (e.g., full-length proteins) with one or more Superbinders. Following enrichment, these undigested pTyr-including peptides can then be subjected to protein digestion (e.g., tryptic digestion) prior to MS analysis. MS analysis could be adjusted to detect various PTMs in the resulting peptide mixture, as would be understood by those skilled in the art.

In a further embodiment, peptides that are covalently or non-covalently bound to pTyr-including peptides are identified and quantified. Such binding may further indicate the activity state of a Tyr-phosphorylated kinase. As will be appreciated by those skilled in the art, identifying such bound peptides may involve enriching pTyr-including peptides that have not been subjected to protein digestion (e.g., full-length proteins) with one or more Superbinders, in conditions that do not disrupt protein-protein interactions. Following enrichment, the bound peptides can then be subjected to protein digestion (e.g., tryptic digestion) prior to MS analysis.

The method may also be a method of determining the tissue of origin for cancer in a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a targeting MS technique, so as to identify and optionally quantify a subset of the pTyr-including peptides that are detectable in the isolated fraction. The test sample may be a biopsy sample, for example from a tumour. The subset may comprise pTyr-including peptides from a particular cell or tissue type, including the tissue type from which the biopsy was extracting, and/or cell or tissue types associated with commonly metastasizing cancers, such as breast or lung tissue. The contacting may comprise using a saturating amount, or an amount below a saturating amount of the SH2 Superbinder. The MS technique may comprise PRM, SRM and/or MRM MS techniques. In this way, the method may be useful for detecting the tissue origin of a tumour, so as to determine if the tumour has metastasized from a different site than the biopsy site.

The method may be a method of detecting and/or quantifying cancer cells in a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a targeting MS technique, so as to identify and optionally quantify a subset of the pTyr-including peptides that are detectable in the isolated fraction. The test sample may be a biopsy sample, for example from a tumour. The subset may comprise pTyr-including peptides from healthy cells of a particular cell or tissue type, including the tissue type from which the biopsy was extracting, and/or cancer cells of the particular cell or tissue type. The contacting may comprise using a saturating amount, or an amount below a saturating amount of the SH2 Superbinder. The MS technique may comprise PRM, SRM and/or MRM MS techniques. In this way, the method may be useful for determining the percentages of cancer and non-cancer cells in a biopsy sample.

The method may be a method of detecting and/or quantifying one or more immune cell type in a test sample, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a targeting MS technique, so as to identify and optionally quantify a subset of the pTyr-including peptides that are detectable in the isolated fraction. The subset may comprise pTyr-including peptides uniquely associated with one of or each of the one or more immune cell types, including B cells, T cells, natural killer cells or macrophages. The MS technique may comprise PRM, SRM and/or MRM MS techniques. In this way, the method may be useful for determining the percentages of specific immune cells in a sample.

The method may be a method of determining activation of one or more signalling pathways, the method comprising: contacting the test sample with an SH2 Superbinder in order to bind pTyr-including peptides contained in the test sample with the SH2 Superbinder; isolating the bound pTyr-including peptides from the test sample; and identifying and optionally quantifying the isolated pTyr-including peptides using a targeting MS technique, so as to identify and optionally quantify a subset of the pTyr-including peptides that are detectable in the isolated fraction. The subset may comprise pTyr-including peptides uniquely associated with one of or each of the one or more signalling pathways. The pTyr-including peptides may be from a kinase, an ITRM or a downstream target of a kinase. The MS technique may comprise PRM, SRM and/or MRM MS techniques. The sample may be perturbed by activation or inhibition with a signalling molecule, including for example PDL1, CD28 or TCR stimulation. In this way, the method may be useful for discriminating between activation of various signalling pathways.

EXAMPLES

Example 1—Expression and Purification of Wild-Type and Variant Src SH2 Domains

DNA sequences encoding $His_6$/GST-tagged human Src SH2 (residues Asp144-Lys252, SEQ ID NO: 10), $His_6$/GST-tagged TrM human Src SH2 (SEQ ID NO: 11) or $His_6$-tagged QuadM human Src SH2 (SEQ ID NO: 13) were prepared in a bacterial expression vector, using techniques standard in the art.

The wild-type and variant SH2 domains were expressed in *E. coli* BL21 (DE3). Protein expression was induced with 0.5 mM IPTG overnight at 18° C. The cell pellets were re-suspended in a lysis buffer containing 2% Triton X-100, 1 mg/mL lysozyme, 3 μL benzonase and 20 mM imidazole in phosphate-buffered saline (PBS) solution (pH 7.0), and sonicated at 400 W for 180 s. The bacterial lysate was cleared by centrifugation at 25,000 g for 30 min and the resulting supernatant used immediately or aliquoted and stored at −80° C. for future usage. $Ni^{2+}$-nitrilotriacetic acid (Ni-NTA) beads, available from GE Healthcare, were used to purify the wild-type and variant SH2 domain proteins. The concentration of each purified protein was determined by Bradford assay.

FIG. 1 is an image of a Coomassie-stained SDS-PAGE gel showing the purification of the three proteins.

Example 2—Variant SH2 Domains were Better Affinity Reagents than Anti-pTyr Antibodies on a Mole-for-Mole Basis for pTyr-Including Peptides from Jurkat Cells Experiments were conducted to determine the relative efficacy of the variant Src SH2 domains and commonly used anti-pTyr antibodies as affinity reagents for pTyr-including peptides from biological samples. $His_6$/GST-tagged TrM Src SH2 domain (SEQ ID NO: 11) and $His_6$-tagged QuadM Src SH2 domain (SEQ ID NO: 13), as well as anti-pTyr antibodies, were prepared in functionally-equivalent molar amounts by using half the molar amount of the antibodies relative to the SH2 domain variants given that each antibody molecule has two binding sites for its antigen.

The first experiment tested the relative ability of the following affinity reagents to extract pTyr-including peptides from a peptide mixture prepared from Jurkat cells: a $His_6$/GST-tagged TrM Src SH2 (SEQ ID NO: 11), a $His_6$-tagged QuadM Src SH2 (SEQ ID NO: 13), the anti-pTyr antibody 4G10 (agarose conjugate, obtained from Millipore), and a mixture of commercially-available anti-pTyr antibodies. Each of the affinity reagents was tested at a 1× and a 5× amount, as set out in Table 3. The two SH2 affinity reagents were also tested at a 30× amount; the antibodies were not tested at a 30× amount due to the prohibitive cost of doing so. The purified SH2 affinity reagents were prepared as described in Example 1. The antibody mixture contained 4G10 (as above), PY99 (obtained from Santa Cruz Biotechnology), and P-Tyr-100 (slurry of PTMScan® Phospho-Tyrosine Mouse mAb, obtained from Cell Signaling Technology). Since the concentration of P-Tyr-100 is unknown, the amount was used as recommended by the vendor (i.e., 4 µL for 1 mg peptide digest).

TABLE 3

Composition and quantities of affinity reagents used in Example 2

| Amount | Src SH2 domain variants | 4G10 | Antibody mixture |
|---|---|---|---|
| 1× | 0.375 nmol | 0.1875 nmol | 0.0625 nmol 4G10, 0.0625 nmol PY99, 4 µL P-Tyr-100 |
| 5× | 1.875 nmol | 0.9375 nmol | 0.3125 nmol 4G10, 0.3125 nmol PY99, 20 µL P-Tyr-100 |
| 30× | 11.25 nmol | N | N |

Figure 2A:
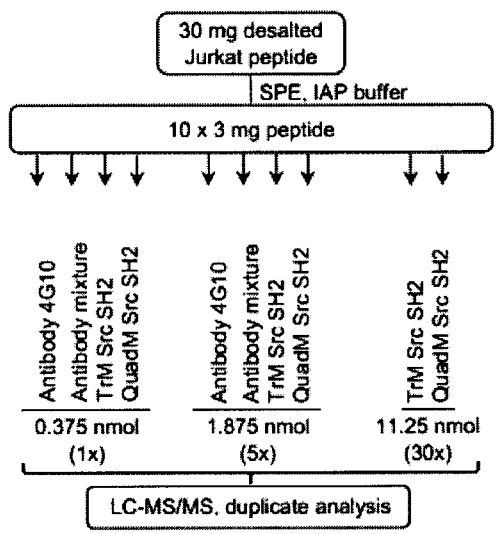
FIG. 2A is a flow diagram for an experiment to determine the relative ability of different molar amounts of anti-pTyr antibodies (4G10 or antibody mixture of 4G10, PY99, and P-TYR-100), $His_6$/GST-tagged TrM Src SH2 Superbinder (SEQ ID NO: 11), and $His_6$-tagged QuadM Src SH2 Superbinder(SEQ ID NO: 13) to identify pTyr-including peptides derived from pervanadate-treated Jurkat cells.

FIG. 2A presents a schematic of the experimental design. Each amount of $His_6$-tagged SH2 domain variant or antibody was subjected to a binding experiment with 3 mg of a peptide mixture prepared from pervanadate-treated Jurkat cells.

Jurkat cells (obtained from ATCC) were cultured in a humidified atmosphere of 5% $CO_2$ at 37° C. in Roswell Park Memorial Institute 1640 medium (RPMI-1640) supplemented with 10% bovine serum and 100 U/mL of streptomycin and penicillin. The cells were collected by centrifugation, washed three times in PBS, and treated with 1 mM freshly prepared sodium pervanadate for 15 min at 37° C., as per Boersema, P. et al., "In-depth qualitative and quantitative profiling of tyrosine phosphorylation using a combination of phosphopeptide immunoaffinity purification and stable isotope dimethyl labeling", (2009) *Molecular &Cellular Proteomics* 9:84-99.

The cells were again collected by centrifugation. The cell pellets were gently homogenized in an ice-cold lysis buffer containing 8 M urea, 50 mM tris(hydroxymethyl)aminomethane (Tris)-HCl (pH 7.4), 2% protease inhibitor cocktail (v/v, obtained from Sigma-Aldrich), 1% Triton X-100 (v/v), 1 mM NaF, and 1 mM $Na_3VO_4$, followed by sonication at 400 W for 120 s. After centrifugation at 25,000 g for 1 h, proteins were precipitated in ice-cold acetone/ethanol/acetic acid (50/50/0.1, V/V/V) solution. Subsequently, the proteins were diluted in reducing buffer containing 100 mM triethylammonium bicarbonate (TEAB) buffer (pH 8.2) and 8 M urea, and the final protein concentration was determined by Bradford assay. The protein suspension was reduced in 10 mM dithiothreitol (DTT) at 37° C. for 2 h, and it was then alkylated in 20 mM iodoacetamide (IAA) in darkness at room temperature for another 30 min. Trypsin digestion was performed at 37° C. overnight with an enzyme-to-protein ratio of 1/25 (w/w). The resulting peptide mixture was stored at −80° C. for further analysis.

Desalted Jurkat peptides (30 mg) were dissolved in ice-cold immunoaffinity purification (IAP) buffer and then split into 10 aliquots with 3 mg of Jurkat peptides each. Binding experiments were performed with the amounts of antibody (1×, 5×) or SH2 domain variant (1×, 5×, 30×) set out in Table 1 and FIG. 2A.

For antibody-based enrichment, 4G10 or the antibody mixture was incubated with the sample at 4° C. overnight while rotating. The beads were washed three times with ice-cold IAP buffer and twice with ice-cold water. To release the bound peptides, the beads were eluted twice with 200 µL 0.15% trifluoroacetic acid (TFA) for 15 min at room temperature.

For SH2-based enrichment, Ni-NTA beads containing the purified SH2 proteins were washed extensively in twenty column volumes of PBS buffer (pH 7.0) containing 20 mM imidazole. Immediately prior to use, the SH2-Ni-NTA beads were washed with two column volumes of ice-cold immunoaffinity purification (IAP) buffer containing 50 mM Tris-HCl (pH 7.2), 50 mM NaCl and 10 mM $Na_2HPO_4$. The washed beads were incubated with the peptide mixture at 4° C. overnight while rotating. The beads were washed the following morning with at least ten columns of ice-cold IAP buffer, and then eluted with PBS buffer (pH 7.0) containing 500 mM imidazole. The eluate was desalted on OASIS HLB columns. The peptides were eluted with a solution of 80% acetonitrile (ACN) and 0.1% trifluoroacetic acid (TFA). Eluted peptides were subjected to immobilized titanium (IV) ion affinity chromatography ($Ti^{4+}$-IMAC) for phosphopeptides, as previously described by Zhou, H. et al., "Specific phosphopeptide enrichment with immobilized titanium ion affinity chromatography adsorbent for phosphoproteome analysis", (2008) *Journal of Proteome Research* 7: 3957-3967; and by Zhou, H. et al., "Robust phosphoproteome enrichment using monodisperse microsphere-based immobilized titanium (IV) ion affinity chromatography" (2013) *Nature Protocols* 8: 461-480. In brief, the peptide mixtures were first incubated with $Ti^{4+}$-IMAC beads in the loading buffer (80% acetonitrile or ACN and 6% TFA) for 30 min at room temperature. After centrifugation, the supernatant was removed. The $Ti^{4+}$-IMAC beads were then washed sequentially in two washing buffers to remove non-specifically adsorbed peptides. Washing buffer 1 contained 50% ACN, 6% TFA, and 200 mM NaCl; washing buffer 2 contained 30% ACN and 0.1% TFA. Bound peptides were then eluted by ammonia (10%, v/v). After centrifugation at 20,000 g for 5 min, the supernatant was collected and lyophilized.

Peptides were detected by one-dimensional (1D) LC-MS/MS, typically carried out on an LTQ Orbitrap Velos (obtained from Thermo Fischer) equipped with a quaternary surveyor MS pump. For 1D LC-MS/MS analysis, the sample was dissolved in 0.1% formic acid (FA) and automatically loaded onto the C18 trapping column (3 cm×200 µm i.d.) at a flow rate of 5 µL/min with 100% mobile phase A. An analytical column (i.d. 75 µm) was packed in-house with Daisogel C18 AQ particles (5 µm, 12 nm) to a length of 15 cm. The mobile phase A was 0.1% formic acid (v/v) in $H_2O$, and mobile phase B was 0.1% FA in ACN. The reversed phase (RP) separation gradient was from 2% to 25% of mobile phase B in 86 min, with the flow rate adjusted to 200 nL/min after splitting. The sample was analyzed three times, each with 20 µL.

The LTQ-Orbitrap Velos mass spectrometer was operated in data-dependent MS/MS acquisition mode. The spray voltage was set at 2.0 kV and the normalized collision energy set as 35.0%. Survey full-scan mass spectrometry (MS) was acquired by the Orbitrap from m/z 400 to 2000 (Resolution=60000 at m/z 400), and the target ion setting was $5e^5$ for the Orbitrap with a max injection time of 250 ms. MS/MS scans were acquired by the LTQ with a target ion setting of $3e^4$ and a max injection time of 50 ms. The dynamic exclusion settings were as follows: repeat count 1, repeat duration 30 s, and exclusion duration 60 s.

The raw MS spectra were processed with MaxQuant version 1.3.0.5. The MS/MS spectra were searched against the UniProt human database (released on Dec. 11, 2013 and containing 88473 protein sequences), supplemented by frequently observed contaminants, and concatenated with reversed versions of all sequences. Enzyme specificity was set to trypsin, and up to two missed cleavage sites were allowed. Phospho (S,T,Y), oxidation (M), loss of ammonia and water were chosen for variable modifications; carbamidomethyl was chosen for fixed modifications. The maximum false-discovery rate (FDR) was set to 1% for both the peptides and proteins. The minimum required peptide length was set at six amino acids. All the phosphorylation sites reported in this study were Class I sites, defined by the combined cutoff values of protein FDR<1%, peptide FDR<1%, localization probability>0.75 and ΔPTM score ≥5. These parameters are commonly used in phosphoproteomics studies (see e.g., Sharma et al.; Olsen, J. V., et al., "Global, in vivo, and site-specific phosphorylation dynamics in signaling networks" (2006) *Cell* 127:635-48; Lundby, A., et al., "Quantitative maps of protein phosphorylation sites across 14 different rat organs and tissues", (2012) *Nature Communications* 3: 876).

Figure 2B:
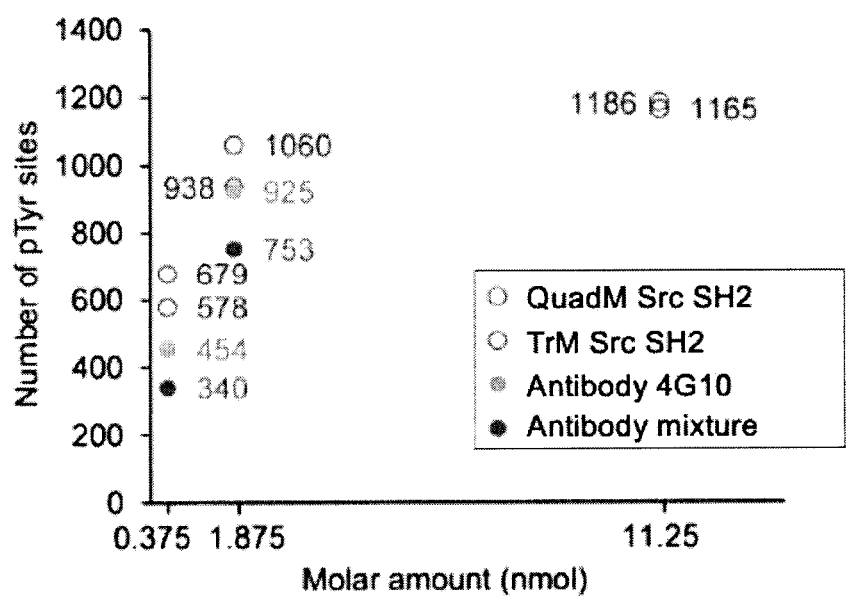
FIG. 2B is a graph that presents the number of pTyr sites identified by each of the affinity reagents, in each of the amounts, in the experiment described in FIG. 2A.

On a mole-for-mole basis (after adjustment for differences in pTyr-binding sites; i.e., an antibody contains two pTyr-binding sites whereas a SH2 domain variant contains one pTyr-binding site per molecule), both the TrM and the QuadM Src domain variants identified more pTyr sites from Jurkat cells than either 4G10 or the antibody mixture, when compared at either the 1× amount (i.e., 0.375 nmol of pTyr-binding sites) or the 5× amount (i.e., 1.875 nmol of pTyr-binding sites). The number of pTyr sites identified in each binding experiment is presented in Table 4, and the same data is charted in FIG. 2B.

TABLE 4

Number of pTyr sites identified by different affinity reagents from pervanadate-treated Jurkat cells

| | Quantity of pTyr-binding sites in affinity reagent used (nmol) | | |
|---|---|---|---|
| Affinity Reagent | 0.375 (1x) | 1.875 (5x) | 11.25 (30x) |
| TrM Src SH2 | 578 | 1060 | 1165 |
| QuadM Src SH2 | 679 | 938 | 1186 |
| Antibody 4G10 | 454 | 925 | |
| Antibody mixture | 340 | 753 | |

Example 3—when TrM and QuadM Src SH2 Domain Variants are Present at Higher Concentration, their Sequence Selectivity Becomes Less Significant The pTyr-including peptides identified in Example 2 were analyzed to calculate the distance in selectivity between the different affinity reagents for pTyr-including peptides. The selectivity was measured by the distribution patterns of the amino acid residues surrounding the pTyr residue in the identified phosphopeptides. The distance in selectivity between two affinity reagents was measured by the Euclidean distance of the corresponding patterns.

Figure 3:
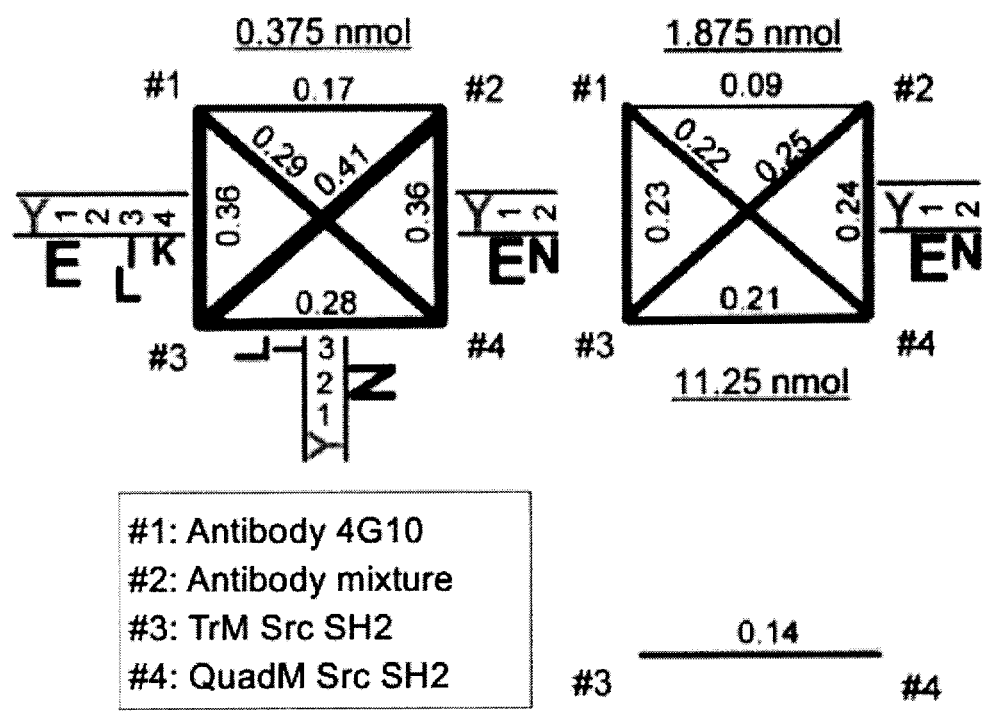
FIG. 3 is a diagram presenting an analysis of the data from the experiment in FIGS. 2A and 2B, particularly showing, at three different equivalent molar amounts (i.e., 0.375 nmol, 1.875 nmol, and 11.25 nmol), the Euclidean distances (values next to lines) in pairwise comparisons (pairs connected by lines) between the amino acid sequences flanking pTyr in pTyr-including peptides identified by each of the four affinity reagents (corners of squares and see legend); the relative thickness (but not distance) of the lines also indicates the relative Euclidean distance; also depicted in FIG. 3 are amino acids at the +1, +2, +3, and +4 positions C-terminal to the pTyr (Y) that are statistically different at the specified locations ($P<0.01$, binomial test without Bonferroni correction) in the indicated pairwise comparisons of the four affinity reagents (i.e., those pairwise comparisons on the perimeter of each square) and have the distance $>0.08$ between the two patterns.

FIG. 3 shows at the 1× amount (i.e., 0.375 nmol of pTyr-binding sites), the 5× amount (i.e., 1.875 nmol of pTyr-binding sites), and the 30× amount (i.e., 11.25 nmol of pTyr-binding sites) the selectivity distances between 4G10 (corner #1), the antibody mixture (corner #2), the TrM Src SH2 (corner #3), and the QuadM Src SH2 (corner #4). The Euclidean distance between the sequences identified by the affinity reagents in each combination is shown along the line connecting the two affinity reagents, and the relative thickness (but not distance) of the line connecting the four affinity reagents also indicates the relative Euclidean distance.

Also depicted in FIG. 3 are amino acids at the +1, +2, +3, and +4 positions C-terminal to the pTyr (Y) that are statistically different at the specified locations (P<0.01, binomial test without Bonferroni correction) and have the distance >0.08 between the two patterns.

When applied at a relatively small amount (i.e., capacity equivalent to 0.375 nmol SH2 domain), the different affinity reagents displayed distinct specificities (FIG. 3). Significant differences in motif-selection were observed between the TrM and QuadM Src SH2 domains and between each SH2 domain and antibody preparation (4G10 or the antibody mixture).

However, the differences in motif selectivity became less significant or insignificant when the quantity of the affinity reagent applied was increased (i.e., by 5-fold to 1.875 nmol or 30-fold to 11.25 nmol; FIG. 3).

FIG. 3 indicates that the sequence specificity of the TrM and QuadM Src SH2 decreased as the amount of SH2 domain variant in the binding reaction increases.

Example 4—a Superbinder Affinity Reagent Provides the Most Expansive View of the Tyrosine Phosphoproteome to Date The Tyr phosphoproteome in nine commonly-used human cell lines was determined using a SH2 Superbinder as an affinity reagent. A schematic of the experiment is set out in FIG. 4.

The cell lines were HeLa (cervical cancer); Bel7402 and HepG2 (liver cancer); MDA-MB-231, BT-474, SK-BR-3, and MCF-7 (breast cancer); MCF-10A (mammary epithelial); and Jurkat cells (T cells). All cell lines (except the human hepatoma Bel7402 cells, which were obtained from the Institute of Blood, Chinese Academy of Medical Sciences) were purchased from ATCC. HeLa, Jurkat, Bel7402, Hep-G2 and MCF-7 cells were cultured in RPMI-1640 medium supplemented with 10% bovine serum. BT-474 cells were grown in RPMI-1640, supplemented with 15% fetal bovine serum, 2.5 g/L glucose and 0.11 g/L sodium pyruvate. SK-BR-3 cells were grown in Dulbecco's Modified Eagle Media (DMEM) supplemented with 15% fetal bovine serum. MBA-MD-231 cells were cultured in RPMI-1640 supplemented with 10% fetal bovine serum. MCF-10A cells were grown in DMEM/F12 (Dulbecco's Modified Eagle Media: Nutrient Mixture F-12) supplemented with 5% horse serum, 20 ng/mL epidermal growth factor (EGF), 10 µg/mL insulin, 0.51 µg/mL hydrocortisone, and 100 ng/mL cholera toxin (Debnath, J. et al., "Morphogenesis and oncogenesis of MCF-10A mammary epithelial acini grown in three-dimensional basement membrane cultures", (2003) *Methods* 30:256-268). All cells were cultured in a humidified atmosphere of 5% CO2 at 37° C., and all media were supplemented with 100 U/mL of streptomycin and penicillin.

To maximize pTyr identification, each cell line was subjected to sodium pervanadate treatment (as in Example 2), and 10 mg protein from each cell line was subjected to trypsin digestion and sequential enrichment by 37.5 nmol (1.5 mg) of $His_6$/GST-tagged TrM Src SH2 (SEQ ID NO: 11) and $Ti^{4+}$-IMAC. Purification of pTyr-including peptides from each of the cell lines was otherwise as in Example 2.

The eluted peptides were identified by SCX-RPLC-MS/MS analysis run for 24 hours. A 14 cm RP-SCX (reversed phase strong cation exchange) biphasic column (i.d. 200 µm) was prepared as previously described by Wang, F., et al., "A fully automated system with online sample loading, isotope dimethyl labeling and multidimensional separation for high-through put quantitative proteome analysis", (2010) *Anal. Chem.* 82:3007-3015. The peptides were re-dissolved in 0.1% FA and automatically loaded onto the RP segment of the RP-SCX biphasic trapping column. Peptides retained on the RP segment were eluted by a RP gradient onto the SCX monolithic column. Subsequently, a series of stepwise elution with 10, 20, 30, 50, 75, 100, 200, 1000 or 10, 30, 50, 100, 1000 mM ammonium acetate was used to elute peptides from the SCX monolithic column to the second-dimension C18 analytical column. Each elution lasted 10 min and was followed by 10 min equilibrium with 0.1% FA. Finally, the RP separation was performed. MS/MS analysis was otherwise performed as described in Example 2.

This phosphoproteomic profiling of the 9 cell lines led to the identification of 19,570 distinct pTyr-including peptides and 10,030 unique pTyr sites (Table 5). The pTyr-including peptides were derived from 4,773 proteins. This appears to be the largest number of pTyr sites obtained in a single study to date. Around 36% of the pTyr sites identified were novel as they were not listed in the ProteomeScout database (version: 2015/10/11), which contains phosphorylation sites collected in multiple other databases including Phospho-SitePlus, dbPTM and UniProtKB (Matlock, M. K., et al., "ProteomeScout: a repository and analysis resource for post-translational modifications and proteins." (2015) *Nucleic Acids Res.* 43:D521-30). Indeed, this work expanded the ProteomeScout database by around 10%.

The contrast between the present study and previous ones in terms of the total and novel pTyr sites identified per cell line is even more striking (Table 5). For example, the largest number of pTyr sites previously identified in a single study of the breast cancer cell line SK-BR-3 is 158; the Superbinder-based approach identified 3,187 pTyr sites in SK-BR-3, of which 692 are novel (Table 5). Thus, the Superbinder-based affinity purification(AP)-MS/MS approach enabled much broader and deeper coverage of the Tyr phosphoproteome than previous methods.

TABLE 5 pTyr sites identified using the Superbinder-based AP-MS/MS method

| Cell line | Tissue | Known pTyr sites* Most sites identified from a single study to date | pTyr sites identified in this study All | Novel |
|---|---|---|---|---|
| Jurkat | T cell | 2,738 (ID: 12495) | 5,326 | 1,557 |
| HeLa | Cervix | 1,131 (ID: 9059) | 3,267 | 750 |
| BT-474 | Breast | 590 (ID: 7219) | 3,745 | 914 |
| SK-BR-3 | Breast | 158 (ID: 776) | 3,187 | 692 |
| MCF-7 | Breast | 101 (ID: 775) | 2,588 | 504 |
| MCF-10A | Breast | 429 (ID: 753) | 3,279 | 681 |
| MDA-MB-231 | Breast | 866 (PMID: 20562096) | 3,152 | 743 |
| HepG2 | Liver | 321 (ID: 7353) | 4,671 | 1,276 |
| BEL7402 | Liver | — | 4,424 | 1,040 |
| Total | | | 10,030 | 3,575 |

*pTyr peptides enriched via the antibody P-Tyr-100 (Cell Signaling Technology, Inc., or CST); the CST curation set ID was included as reference except for MDA-MB-231 for which the PubMed ID of the corresponding study was given in parenthesis.

Example 5—Analysis of the Tyrosine Phosphoproteome Uncovered by the SH2 Superbinder The phosphoproteomic information obtained in Example 4 was subjected to different analyses.

The nine cell lines had markedly different Tyr phosphorylation profiles. A previous analysis of 11 human cell lines revealed that ~73% of the identified proteins were common to all cells (Geiger, T. et al. "Comparative proteomic analysis of eleven common cell lines reveals ubiquitous but varying expression of most proteins" (2012) *Mol. Cell. Proteomics* 11: M111.014050).

The number of pTyr sites shared between two or more cell types followed a similar trend with only ~5.8% (584/10,030) of pTyr sites detected in all 9 cell lines (Table 6). Moreover, approximately 50% of the novel pTyr sites identified in this study were specific to a single cell-type (Table 6). In general, the more cell-type specific a pTyr site, the more likely it was to be novel (i.e., first identified in this study, Table 6).

TABLE 6

The number of pTyr sites found in the phosphoproteomic analysis of Example 4 that were cell-type specific or common to 2 through 9 cell lines

| Cell specificity | # pTyr sites | # novel pTyr sites | % novel pTyr sites |
|---|---|---|---|
| 1 | 3,470 | 1,758 | 50.7% |
| 2 | 1,661 | 708 | 42.6% |
| 3 | 1,127 | 397 | 35.2% |
| 4 | 865 | 254 | 29.4% |
| 5 | 731 | 174 | 23.8% |
| 6 | 545 | 110 | 20.2% |
| 7 | 551 | 74 | 13.4% |
| 8 | 496 | 54 | 10.9% |
| 9 | 584 | 44 | 7.5% |
| Total | 10,030 | 3,575 | 35.6% |

Figure 5:
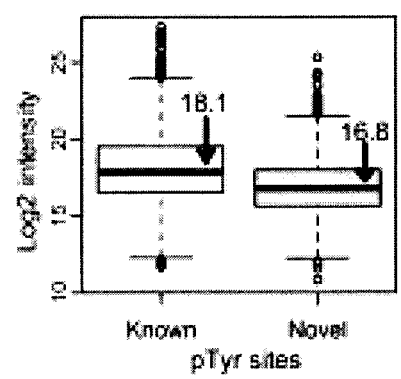
FIG. 5 is a box-and-whiskers plot of the log 2 m/z peak intensities of the pTyr sites identified from nine human cell lines using the $His_6$-tagged/GST-tagged TrM Src SH2 Superbinder (SEQ ID NO: 11), classified by whether the site was previously known or first identified in the experiment (novel), with the thick black line (and number with arrow) indicating the median.

The relatively high abundance of the pTyr sites found in all 9 cell lines may explain why there were relatively few novel sites (around 7.5%) identified by the Superbinder within this group (Table 6). That is, these highly-abundant pTyr peptides may have been preferentially isolated when a limited quantity of affinity reagents were used in previous AP-MS/MS analyses (i.e., using anti-pTyr antibodies as affinity reagents). By this rationale, the novel pTyr sites identified using a saturating amount of Superbinder would be predicted to generally be of lower abundance relative to those reported to date. Consistent with this prediction, the average m/z peak intensity of peptides corresponding to known pTyr sites was around 2.5 times that of novel pTyr sites (FIG. 5). Novel pTyr sites are significantly less abundant than known ones (P<$2.2 \times 10^{-16}$, Student's t-test).

Figure 6A:
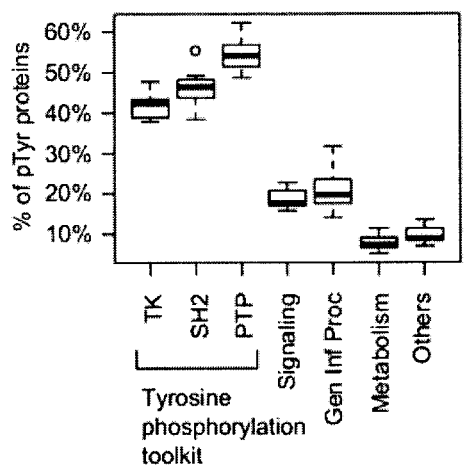
FIG. 6A is a box-and-whiskers plot depicting the percentage of the proteins in different functional categories that were Tyr-phosphorylated in the phosphoproteomic analysis of FIG. 5, with the median percentage from the nine cell lines depicted as a thick line.

The proportion of different functional categories of proteins, as defined by the KEGG database (http://www.genome.jp/kegg/), that were found to be Tyr-phosphorylated is presented in FIG. 6A. In contrast to proteins involved in metabolism for which only a small fraction (~5%) was phosphorylated, around 43% of all TKs, around 47% of SH2 domain-including proteins and around 54% of PTPs were found to be Tyr-phosphorylated across all cell lines.

Figure 6B:
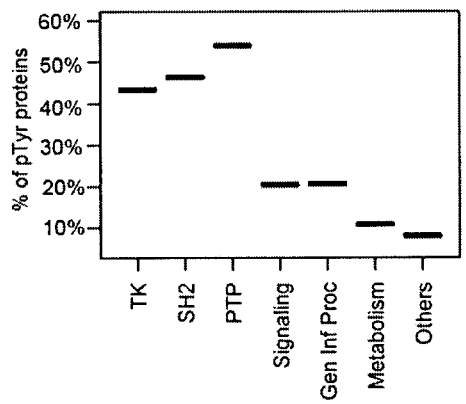
FIG. 6B is a plot akin to that of FIG. 6A but only showing a single percentage for the pTyr-phosphorylated proteins in each functional category, as derived from published phosphoproteomic data of MKN45 cells that were not treated with pervanadate and were subjected to affinity purification with the antibody P-Tyr-1000.

A similar trend in the protein functional categories subjected to Tyr phosphorylation was observed using published phosphoproteomic data from MKN45 cells that were not treated with pervanadate and whose digested peptides were subjected to affinity purification with P-Tyr-100 (FIG. 6B), suggesting that neither the pervanadate treatment nor the Superbinder-based affinity purification altered this general feature of pTyr signaling. The analysis presented in FIG. 6B combines phosphoproteomic data from cells treated with the kinase inhibitors SU11274 or staurosporine or the vehicle DMSO (Stokes, M. P. et al., "Complementary PTM Profiling of Drug Response in Human Gastric Carcinoma by Immunoaffinity and IMAC Methods with Total Proteome Analysis" (2015) *Proteomes* 3:160-183).

Figure 6C:
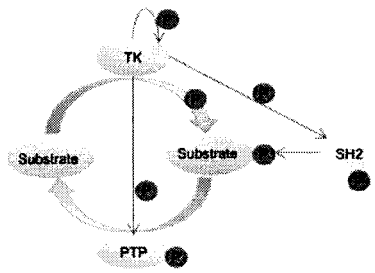
FIG. 6C is a schematic diagram illustrating the apparent general regulation of Tyr-phosphorylation (circles marked with "P") in human cells, with the tyrosine kinases (TK) that phosphorylate substrates, the protein tyrosine phosphatases (PTP) that dephosphorylate substrates, and the SH2-domain-including proteins that bind Tyr-phosphorylated proteins themselves being regulated by Tyr-phosphorylation.

These findings suggest that the core machinery in pTyr signaling—TKs, PTPs, and SH2-including proteins—is itself subject to extensive regulation by Tyr phosphorylation (FIG. 6C).

FIG. 6C is a schematic diagram illustrating the apparent general regulation of Tyr-phosphorylation (circles marked with "P") in human cells, with the tyrosine kinases (TK) that phosphorylate substrates, the protein tyrosine phosphatases (PTP) that dephosphorylate substrates, and the SH2-domain-including proteins that bind Tyr-phosphorylated proteins themselves being regulated by Tyr-phosphorylation.

Example 6—Tyrosine Phosphorylation on PTPs Indicates Likely Regulatory Sites It was known that Tyr-phosphorylation of TKs can regulate their activity and that Tyr-phosphorylation of SH2-domain-including proteins can modify their binding specificity or affinity (for e.g., Hubbard, S. R. et al., "Autoregulatory mechanisms in protein-tyrosine kinases", (1998) *J. Biol. Chem.* 273:11987-90; Qian, X. et al., "The Tensin-3 protein, including its SH2 domain, is phosphorylated by Src and contributes to tumorigenesis and metastasis" (2009) *Cancer Cell* 16:246-58; Jin, L. L. et al., "Tyrosine phosphorylation of the Lyn Src homology 2 (SH2) domain modulates its binding affinity and specificity" (2015) *Mol. Cell. Proteomics* 14: 695-706). But it was surprising that PTPs were so pervasively Tyr-phosphorylated in the phosphoproteomic data described in Examples 4 and 5.

Figure 7A:
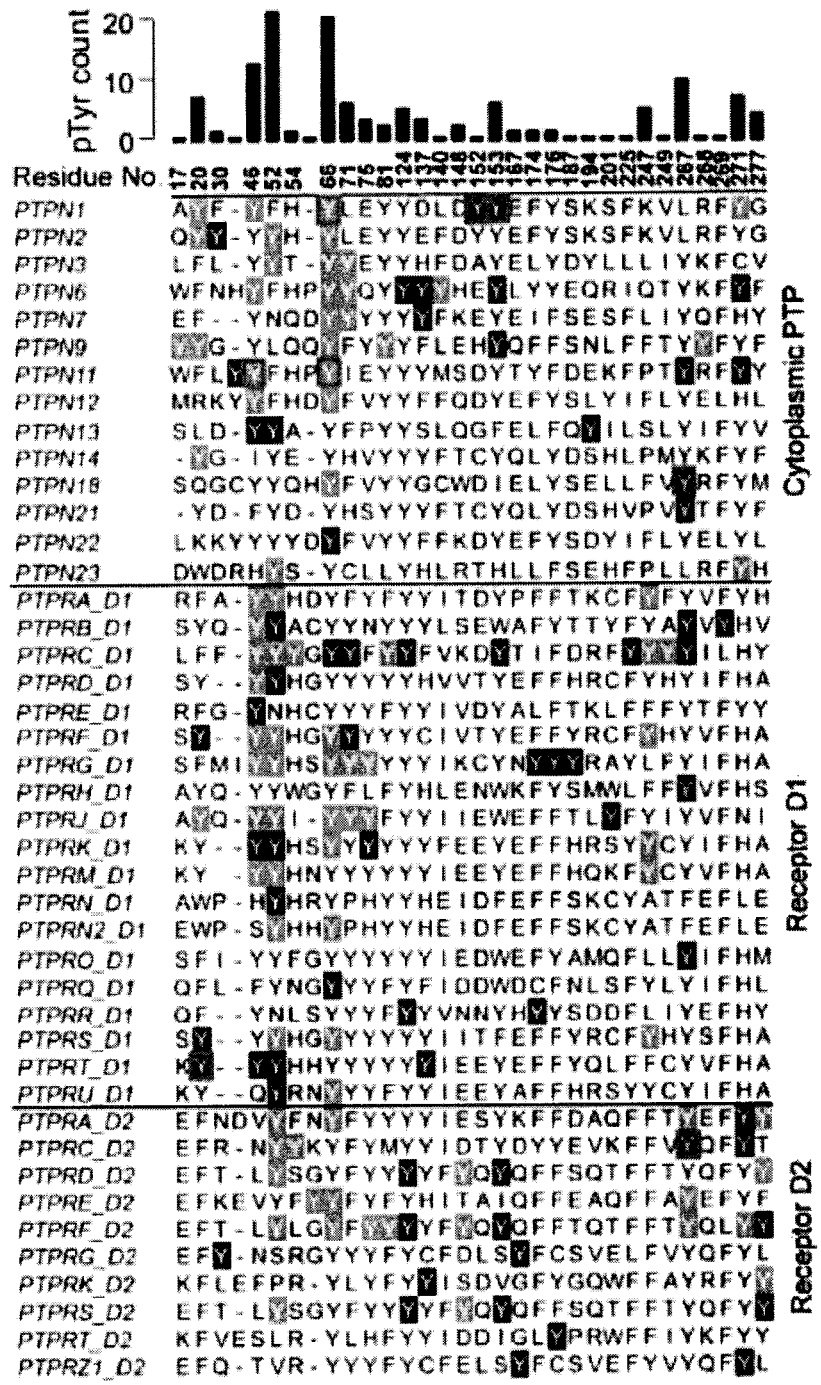
FIG. 7A is a condensed sequence alignment of a representative list of PTP domains encoded by human genes (in italics) that have been grouped into three categories (cytoplasmic PTPs, receptor D1 PTPs, and receptor D2 PTPs) and aligned against the PTP domain in PTPN1, with PTPN1 residue numbers provided above the aligned amino acids; the bar graph above the alignment showing the number of PTPs in which that residue, as aligned, was found to be Tyr-phosphorylated in the phosphoproteomic study of FIG. 5; the pTyr sites are color-coded with 32 novel pTyr sites identified in that study in green, 67 previously-identified pTyr sites in blue, 56 previously-identified pTyr sites that were also identified in that study in grey, and pTyr sites that have been functionally annotated identified by red boxes.
Figure 7B:
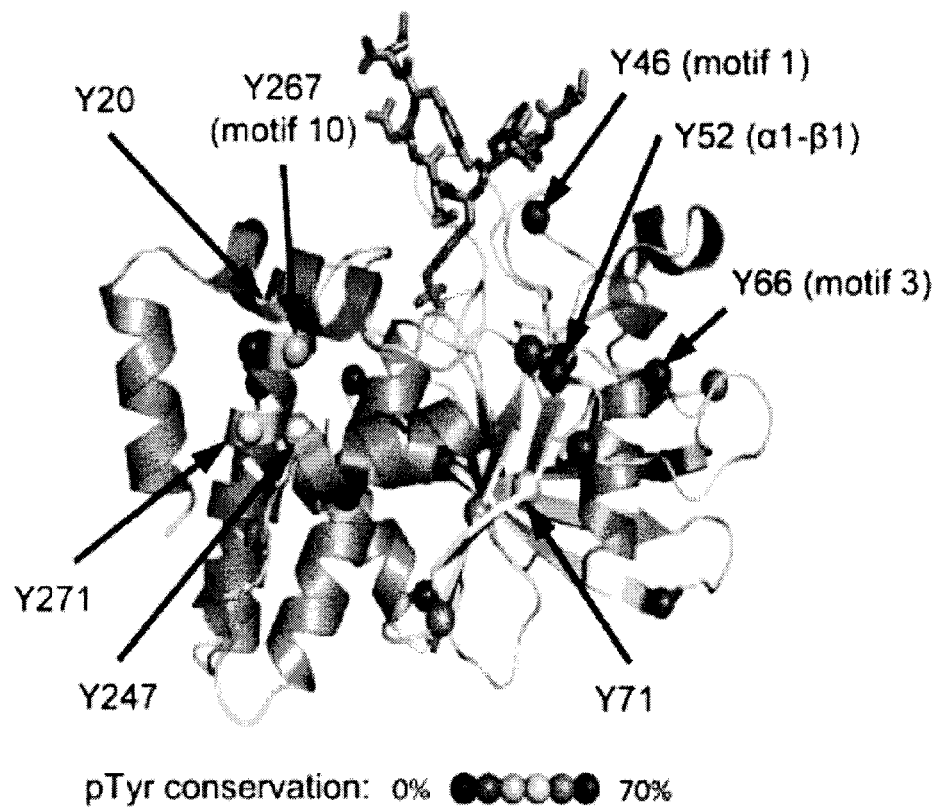
FIG. 7B is a representation of the three-dimensional structure (PDB code 1EEO) of the PTPN1 PTP domain, with the approximate location of the major Tyr (Y) phosphosites indicated as labelled spheres and with the colour of the sphere indicating the degree of conservation for that Tyr residue within the PTP family according to the provided blue-to-red gradient.

The majority (56%) of pTyr sites identified in PTPs were located within the PTP domain. As around 36% of the identified pTyr sites in PTPs were novel, this work expanded the identified intra-PTP domain Tyr phosphorylation sites by around 27%. Furthermore, many conserved Tyr residues within conserved motifs in the PTP domain were found phosphorylated across the different cell lines (for e.g., in FIGS. 7A and 7B see Tyr46, Tyr52, Tyr66, Tyr267, residue numbering based on PTPN1). In particular, Tyr46, Tyr52, and Tyr66 (numbering based on PTPN1) were the most conserved (around 70%) and the most frequently Tyr-phosphorylated residues (FIG. 7A). Tyr46, Tyr52, and Tyr66 are clustered in the three-dimensional structure of PTPN1 (FIG. 7B).

The literature further suggests that phosphorylation of many of these conserved residues (for e.g., Tyr46, Tyr66, Tyr267) can be predicted to affect PTP function by modulating phosphatase activity and/or by creating docking sites for other signaling proteins.

For example, Tyr46 (numbering based on PTPN1) within Motif 1 is known to play a key role in defining PTP substrate specificity through hydrophobic packing with the pTyr residue of the substrate (Andersen, J. N. et al., "Structural and evolutionary relationships among protein tyrosine phosphatase domains", (2001) *Mol. Cell. Biol.* 21:7117-36). The phosphorylation of Tyr46 is thus expected to have a negative impact on substrate recognition. Indeed, phosphorylation of Tyr279 on PTPN11 (SHP-2), which is equivalent to Tyr46 in PTPN1, has been shown to reduce PTPN11 activity (Mitra, S. et al., "SHP-2 is a novel target of Abl kinases during cell proliferation" (2008), *J. Cell Sci.* 121:3335-46).

As another example, Tyr66 (numbering based on PTPN1) within Motif 3 is known to contribute to the formation of the hydrophobic core of the PTP domain (Andersen et al.). Phosphorylation of Tyr66 in PTPN1 or the equivalent residue in PTPN11 was previously shown to mediate binding of the corresponding PTP to the Grb2 SH2 domain and to enhance phosphatase activity (Mitra et al.; Liu, F. and Chernoff, J., "Protein tyrosine phosphatase 1B interacts with and is tyrosine phosphorylated by the epidermal growth factor receptor" (1997) *Biochem. J.* 327(Pt 1):139-45).

As yet another example, phosphorylation of Tyr267 (numbering based on PTPN1) within the Q-loop (Motif 10) may alter PTP activity (Andersen, J. N. et al., "Structural and evolutionary relationships among protein tyrosine phosphatase domains" (2001) *Mol. Cell. Biol.* 21:7117-36; Mitra, S. et al.).

Example 7—pTyr on TK Activation Loops Indicated TK Activity

The phosphoproteomic data obtained in Example 4 was used to determine the relative activity of TKs in the 9 different cell lines by identifying and quantifying pTyr-including peptides derived from TK activation loops.

Potential pTyr sites in TK activation loops were determined by literature searches and by bioinformatics. For instance, data collected from the database PhosphoSitePlus (www.phosphosite.org) provides 35 examples of a Tyr in the activation loop of a TK whose phosphorylation has been documented to increase kinase activity (Table 7).

TABLE 7

35 examples of pTyr in TK activation loops whose phosphorylation has been documented to increase kinase activity

| No. | Protein | Swissprot ID | Residue No. of pTyr in activation loop |
|---|---|---|---|
| 1 | BTK | Q06187 | 551 |
| 2 | EGFR | P00533 | 869 |
| 3 | EPHA3 | P29320 | 779 |
| 4 | FER | P16591 | 714 |
| 5 | FES | P07332 | 713 |
| 6 | FGFR1 | P11362 | 653 |
| 7 | FGFR1 | P11362 | 654 |
| 8 | IGF1R | P08069 | 1165 |
| 9 | IGF1R | P08069 | 1166 |
| 10 | INSR | P06213 | 1189 |
| 11 | INSR | P06213 | 1190 |
| 12 | JAK3 | P52333 | 980 |
| 13 | KDR | P35968 | 1059 |
| 14 | LCK | P06239 | 394 |
| 15 | LYN | P07948 | 397 |
| 16 | MERTK | Q12866 | 753 |
| 17 | MERTK | Q12866 | 754 |
| 18 | MET | P08581 | 1234 |
| 19 | MET | P08581 | 1235 |
| 20 | MST1R | Q04912 | 1238 |
| 21 | NTRK1 | P04629 | 680 |
| 22 | NTRK1 | P04629 | 681 |
| 23 | PDGFRB | P09619 | 857 |
| 24 | PTK2 | Q05397 | 576 |
| 25 | PTK2 | Q05397 | 577 |
| 26 | PTK6 | Q13882 | 342 |
| 27 | RET | P07949 | 905 |
| 28 | SRC | P12931 | 419 |
| 29 | SYK | P43405 | 525 |
| 30 | SYK | P43405 | 526 |
| 31 | TEC | P42680 | 519 |
| 32 | TNK2 | Q07912 | 284 |
| 33 | TYK2 | P29597 | 1054 |
| 34 | TYK2 | P29597 | 1055 |
| 35 | ZAP70 | P43403 | 493 |

A further sequence analysis identified 126 potential regulatory pTyr sites, including 86 within the activation loop, for 86 of the 90 human tyrosine kinases (Table 8). Some TKs (i.e., EPHA6/7, EPHA3/4/5, ABL1/2, IGF1R/INSR, VGFR2/3, NTRK2/3) have identical activation loop sequences.

TABLE 8

79 tryptic peptides comprising a Tyr residue from human TK activation loops

| No. | Name of TK | Sequence | Length |
|---|---|---|---|
| 1 | TNK1 | YVMGGPRPIPYAWCAPESLR | 20 |
| 2 | RYK | DLFPMDYHCLGDNENRPVR | 19 |
| 3 | EPHB1 | YLQDDTSDPTYTSSLGGK | 18 |
| 4 | EPHB2 | FLEDDTSDPTYTSALGGK | 18 |
| 5 | EPHB3 | FLEDDPSDPTYTSSLGGK | 18 |
| 6 | EPHB4 | FLEENSSDPTYTSSLGGK | 18 |
| 7 | EPHA2 | VLEDDPEATYTTSGGK | 16 |
| 8 | EPHA6/7 | VLEDDPEAAYTTTGGK | 16 |
| 9 | EPHA8 | VLEDDPDAAYTTTGGK | 16 |
| 10 | ACK1 | ALPQNDDHYVMQEHR | 15 |
| 11 | EPHA1 | LLDDFDGTYETQGGK | 15 |
| 12 | ERBB2 | LLDIDETEYHADGGK | 15 |
| 13 | LMTK1 | EDYFVTADQLWVPLR | 15 |
| 14 | ABL1/2 | LMTGDTYTAHAGAK | 14 |
| 15 | BMX | YVLDDQYVSSVGTK | 14 |
| 16 | BTK | YVLDDEYTSSVGSK | 14 |
| 17 | FES | EEADGVYAASGGLR | 14 |
| 18 | ITK | FVLDDQYTSSTGTK | 14 |
| 19 | PTK6 | EDVYLSHDHNIPYK | 14 |
| 20 | TEC | YVLDDQYTSSSGAK | 14 |
| 21 | TXK | YVLDDEYVSSFGAK | 14 |
| 22 | BLK | IIDSEYTAQEGAK | 13 |
| 23 | EPHA3/4/5 | VLEDDPEAAYTTR | 13 |
| 24 | FER | QEDGGVYSSSGLK | 13 |
| 25 | ZAP70 | ALGADDSYYTAR | 12 |
| 26 | CSF1R | DIMNDSNYIVK | 11 |
| 27 | FGR | DDEYNPCQGSK | 11 |
| 28 | FLT3 | DIMSDSNYVVR | 11 |
| 29 | PGFRA | DIMHDSNYVSK | 11 |
| 30 | PTK7 | DVYNSEYYHFR | 11 |
| 31 | SRMS | DDIYSPSSSSK | 11 |
| 32 | FRK | VDNEDIYESR | 10 |
| 33 | FYN | LIEDNEYTAR | 10 |
| 34 | HCK | VIEDNEYTAR | 10 |
| 35 | LCK | LIEDNEYTAR | 10 |
| 36 | LYN | VIEDNEYTAR | 10 |
| 37 | RET | DVYEEDSYVK | 10 |
| 38 | SRC | LIEDNEYTAR | 10 |
| 39 | TYK2 | AVPEGHEYYR | 10 |
| 40 | TYK2 | AVPEGHEYYR | 10 |
| 41 | YES | LIEDNEYTAR | 10 |
| 42 | DDR1 | NLYAGDYYR | 9 |
| 43 | DDR2 | NLYSGDYYR | 9 |

TABLE 8-continued 79 tryptic peptides comprising a Tyr residue from human TK activation loops

| No. | Name of TK | Sequence | Length |
|---|---|---|---|
| 44 | FAK1 | YMEDSTYYK | 9 |
| 45 | FAK2 | YIEDEDYYK | 9 |
| 46 | FGFR1 | DIHHIDYYK | 9 |
| 47 | FGFR2 | DINNIDYYK | 9 |
| 48 | FGFR3 | DVHNLDYYK | 9 |
| 49 | FGFR4 | GVHHIDYYK | 9 |
| 50 | IGF1R/INSR | DIYETDYYR | 9 |
| 51 | INSRR | DVYETDYYR | 9 |
| 52 | LMTK2 | EDYIETDDK | 9 |
| 53 | LMTK3 | EDYYLTPER | 9 |
| 54 | MUSK | NIYSADYYK | 9 |
| 55 | NTRK1 | DIYSTDYYR | 9 |
| 56 | NTRK2/3 | DVYSTDYYR | 9 |
| 57 | RON | EYYSVQQHR | 9 |
| 58 | ROR1 | EIYSADYYR | 9 |
| 59 | ROR2 | EVYAADYYK | 9 |
| 60 | EGFR | EYHAEGGK | 8 |
| 61 | ERBB3 | QLLYSEAK | 8 |
| 62 | ERBB4 | EYNADGGK | 8 |
| 63 | KIT | NDSNYVVK | 8 |
| 64 | MERTK | IYSGDYYR | 8 |
| 65 | MET | EYYSVHNK | 8 |
| 66 | TYRO3 | IYSGDYYR | 8 |
| 67 | UFO | IYNGDYYR | 8 |
| 68 | KSYK | ADENYYK | 7 |
| 69 | PGFRB | DSNYISK | 7 |
| 70 | TIE1 | GEEVYVK | 7 |
| 71 | TIE2 | GQEVYVK | 7 |
| 72 | JAK1 | EYYTVK | 6 |
| 73 | JAK3 | DYYVR | 6 |
| 74 | VGFR1 | NPDYVR | 6 |
| 75 | VGFR2/3 | DPDYVR | 6 |
| 76 | ALK | ASYYR | 5 |
| 77 | LTK | ASYYR | 5 |
| 78 | ROS1 | NDYYR | 5 |
| 79 | JAK2 | EYYK | 4 |

Figure 8:
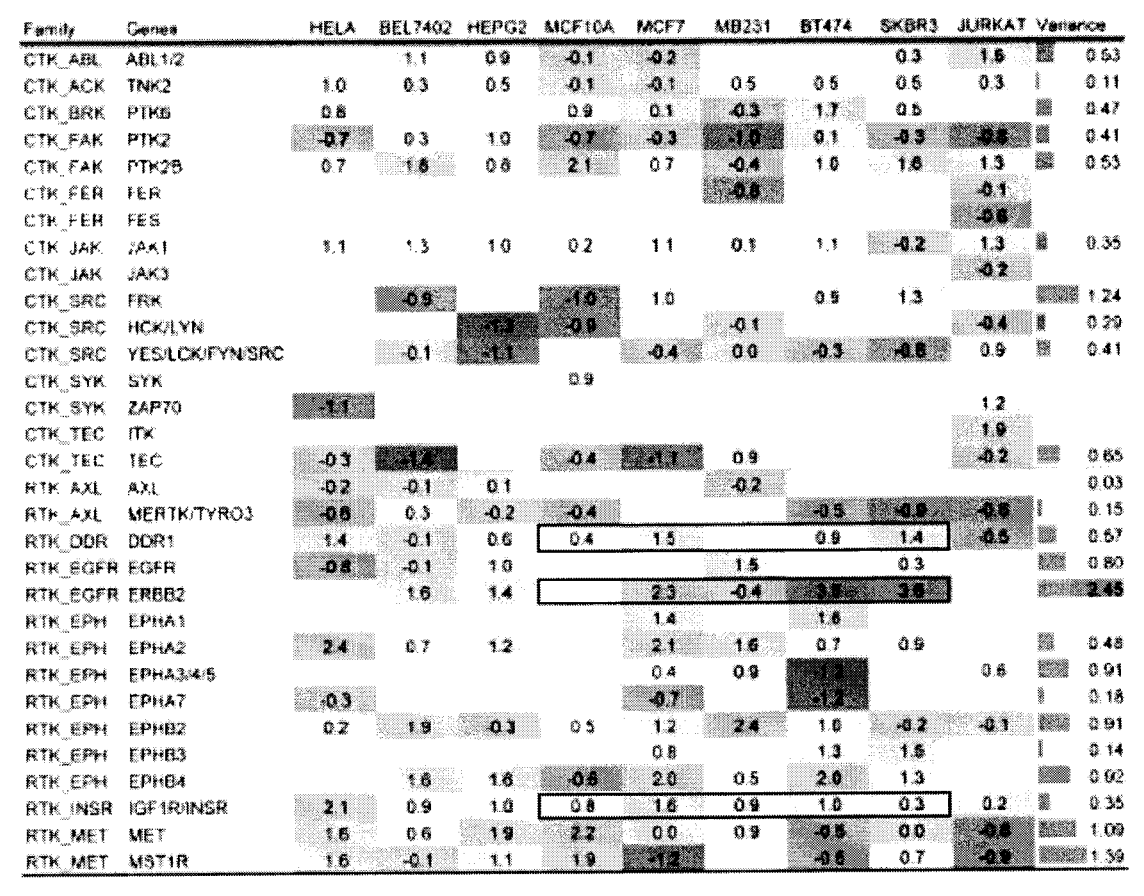

Label-free quantification of the mass spectra was used to create a profile of activation loop Tyr-phosphorylation in 31 TKs for each of the 9 different cell lines (FIG. 8). It was apparent that the different cell lines had distinct profiles, suggesting that TK activation is cell-type specific. For instance, Jurkat cells appeared, in general, to have relatively active CTKs and relatively inactive RTKs. This suggests that phosphotyrosine signaling is dominated by CTKs in Jurkat T cells, and likely also in other hematopoietic cell types, and that RTKs, on the contrary, may play a more important role in the epithelial cancer cells examined herein.

To determine if the phosphoproteomic data faithfully recapitulated protein phosphorylation in vivo, immunoprecipitation (IP) followed by immunoblotting (IB, also known as Western blotting) was carried out on lysates from the four breast cancer cell lines from Example 4 (MDA-MB-231, BT-474, SK-BR-3, and MCF-7).

Total cell lysate was harvested for MCF-7, BT-474, MDA-MB-231 and SK-BR-3 following 15 min of pervanadate treatment. For IPs, 1 mg of cell lysate was incubated with 2 µg anti-ErbB2 or anti-IGF-1Rβ antibodies for 4 hours at 4° C. Protein G beads were then used for antibody precipitation. The samples were separated by SDS-PAGE and then immunoblotted with anti-ErbB2, anti-pY877-ErbB2, anti-IGF1Rβ, anti-pY1161/1165/1166IGF-1Rβ, anti-Grb2 and anti-IRS-1, respectively. As controls, whole cell lysates were immunoblotted for Grb2, IRS-1 and β-tubulin, respectively.

Figure 9A:
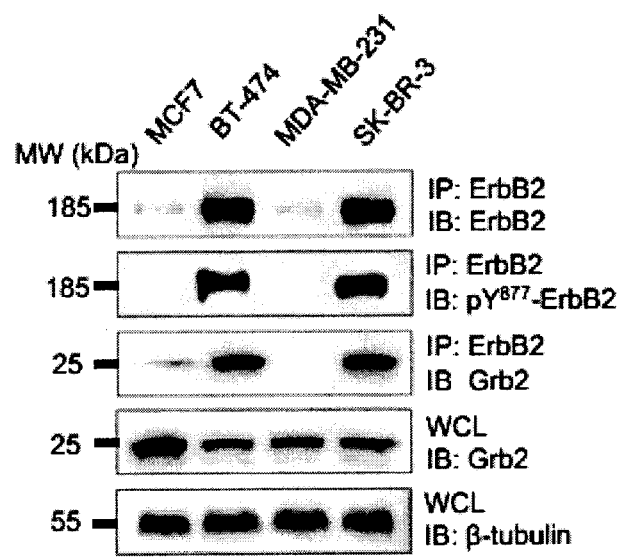
FIG. 9A and FIG. 9B are images of Western blots of proteins resolved by SDS-PAGE and derived from immunoprecipitates (IPs) with anti-ErbB2 antibody, from IPs with anti-IGF-1Rβ antibody, or from whole cell lysates (WCL), for four breast cancer cell lines (MCF-7, BT-474, MDA-MD-231, SK-BR-3); blots were immunoblotted (IB) with the indicated primary antibodies; the approximate molecular weight (MW) in kDa of the proteins is indicated.
Figure 9B:
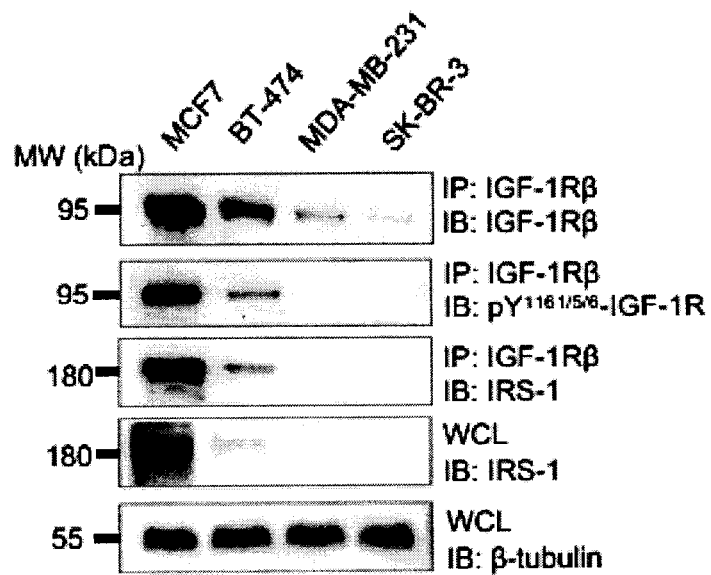
Figure 10A:
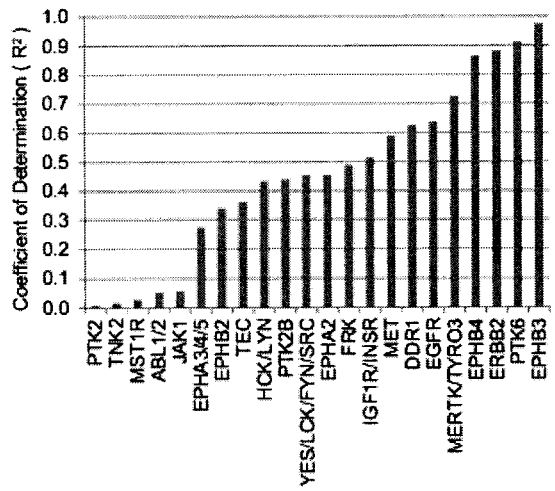
FIG. 10A is a bar graph showing the coefficient of determination ($R^2$) between mRNA abundance and intensity of activation loop Tyr-phosphorylation for the indicated TKs across six (BT-474, HepG2, Jurkat, MCF-7, SK-BR-3, MDA-MB-231) of the nine cell lines from the phosphoproteomic analysis of FIG. 6.
Figure 10B:
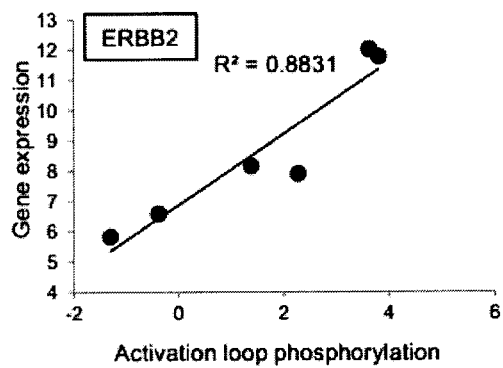
FIGS. 10B to 10D are scatter plots showing the relationship, for the six cell lines from FIG. 10A (black dots), between relative mRNA abundance (gene expression) and intensity of activation loop Tyr-phosphorylation for three TKs, namely ERBB2 (FIG. 10B), IGF1R/INSR (FIG. 10C), and DDR1 (FIG. 10D)
Figure 10C:
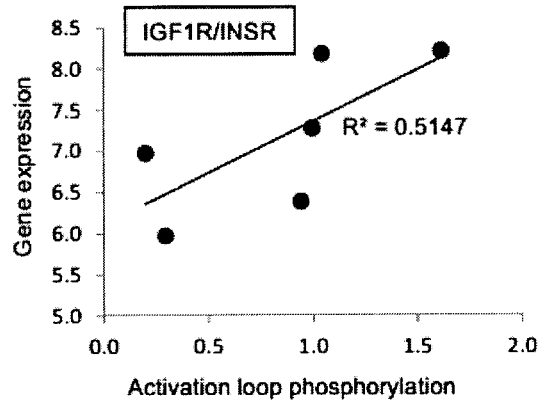
Figure 10D:
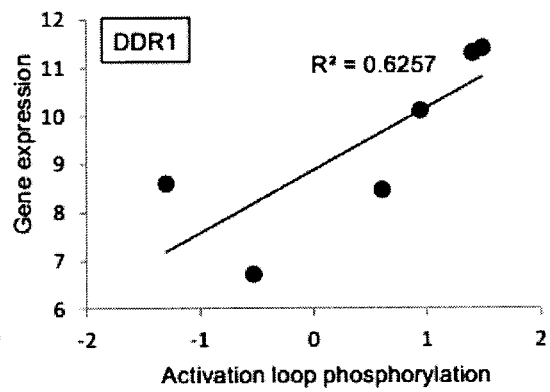

Results from the IP/IB analysis, presented in FIGS. 9A and 9B, were generally consistent with the activation loop phosphorylation profiles presented in FIG. 8. In particular, ErbB2 was highly phosphorylated on Tyr877 in BT-474 and SK-BR-3 cells (FIG. 9A); and the activation loop Tyr residues in IGF-1R were highly phosphorylated in MCF-7 cells, moderately phosphorylated in BT-474 and MDA-MB-231 cells, but not detectably phosphorylated in SK-BR-3 cells (FIG. 9B).

To determine if the TK activation loop phosphorylation level determined by phosphoproteomics predicts kinase activity, activation-dependent recruitment of the downstream proteins Grb2 to ErbB2 and IRS-1 to IGF-1R was examined in the same IP/IB experiments (Xie, Y. M. et al., "Dominant-negative mutants of Grb2 induced reversal of the transformed phenotypes caused by the point mutation-activated rat HER-2/Neu", (1995) *J. Biol. Chem.* 270:30717-30724; SeppLorenzino, L. et al., "Signal transduction pathways induced by heregulin in MDA-MB-453 breast cancer cells", (1996) *Oncogene* 12:1679-1687; Dey, B. R. et al., "Evidence for the direct interaction of the insulin-like growth factor I receptor with IRS-1, Shc, and Grb10", (1996) *Molecular Endocrinology* 10:631-641; Tartare-Deckert, S. et al., "Evidence for a differential interaction of SHC and the insulin receptor substrate-1 (IRS-1) with the insulin-like growth factor-I (IGF-I) receptor in the yeast two-hybrid system", (1995) *J. Biol. Chem.* 270, 23456-60). Consistent with such a prediction, phosphorylated ErbB2 recruited more Grb2 and activated IGF-1R recruited more IRS-1 (FIGS. 9A and 9B).

In FIGS. 9A and 9B, there appeared to be correlation between the detectable Tyr-phosphorylation on the activation loop residues of ErbB2 and IGF-1R and the overall abundance of ErbB2 and IGF-1R in the IP. In general, however, the relative level of gene expression of the TKs, as determined from published data on mRNA abundances in 6 (BT-474, HepG2, Jurkat, MCF-7, SK-BR-3, MDA-MB-231) of the 9 cells lines (Barretina, J. et al., "The Cancer Cell Line Encyclopedia enables predictive modeling of anticancer drug sensitivity" (2012) *Nature* 483:603-607), was not a reliable indicator of the relative level of activation loop phosphorylation of the TKs, as determined by the phosphoproteomic analysis of Example 4 (FIGS. 10A to 10D).

Although it is difficult to discern the contribution of phosphorylation and enhanced protein expression in the case of ErbB2, it seems clear, in the case of IGF-1R, that the activation loop phosphorylation, but not protein expression, correlates with kinase activation in BT-474 cells.

In any event, identifying and quantitating pTyr-including peptides may reveal differences between cell types in both the stoichiometry of Tyr-phosphorylation at a particular site in a given TK (i.e., the proportion of a given Tyr residue(s) in a given TK that is phosphorylated) and the total abundance of that TK. Both higher phosphorylation stoichiometry and higher abundance may increase TK activity.

Example 8—Activation Loop Tyr-Phosphorylation Profiles can Predict Sensitivity to Specific TK Inhibitors and Combinations Thereof An effective strategy in molecular targeted therapy is to selectively inhibit tyrosine kinases that drive tumorigenesis (see e.g., Barretina et al.; Takeuchi, K. and Ito, F, "Receptor tyrosine kinases and targeted cancer therapeutics", (2011) *Biol. Pharm. Bull.* 34:1774-80; Levitzki, A., "Tyrosine kinase inhibitors: views of selectivity, sensitivity, and clinical performance", (2013) *Annu. Rev. Pharmacol. Toxicol.* 53:161-85; Zaman, N. et al., "Signaling network assessment of mutations and copy number variations predict breast cancer subtype-specific drug targets", (2013) *Cell Rep.* 5:216-23). This therapeutic principle was tested on the four breast cancer lines (MCF-7, BT-474, SK-BR-3, MDA-MB-231) from Example 4, which showed distinct profiles of pTyr phosphorylation in the activation loops of TKs, and hence distinct profiles of TK activation (FIG. 8).

Cell growth inhibition assays were performed with the CellTiter 96 AQueous One Solution Cell Proliferation Assay (Promega) according to the manufacturer's recommendations.

Figure 11A:
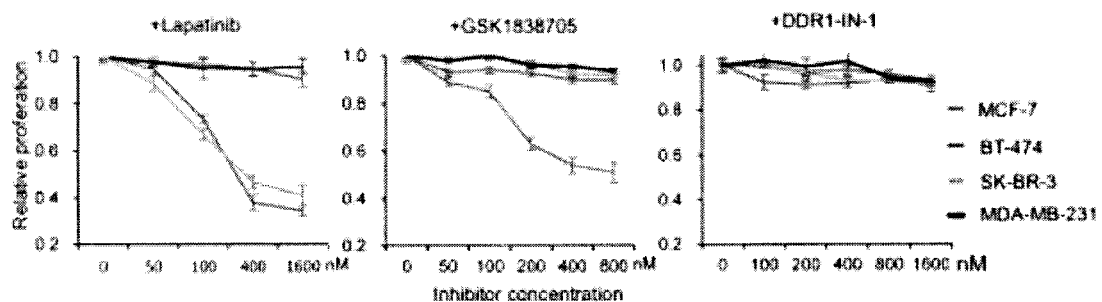
FIG. 11A is line graphs showing the proliferation, relative to no drug exposure, of four breast cancer cell lines (MCF-7, BT-474, MDA-MD-231, SK-BR-3) exposed to different concentrations of small-molecules that inhibit specific TKs, namely lapatinib (ErbB2 inhibitor), GSK1838705 (IGF-1R inhibitor), and DDR1-IN-1 (Ddr1 inhibitor)

Cells from the four breast cancer lines were first treated with the ErbB2 inhibitor lapatinib (Esteva, F. J., et al., "Molecular predictors of response to trastuzumab and lapatinib in breast cancer", (2010) *Nat. Rev. Clin. Oncol.* 7:98-107). BT-474 and SK-BR-3, in which ErbB2 was highly active, were sensitive whereas MCF-7 and MDA-MB-231, in which ErbB2 activity was less active, were insensitive to lapatinib (FIG. 11A).

Because IGF-1R/INSR and DDR1 were selectively activated in MCF-7 (FIG. 8), we treated the four breast cancer cell lines with GSK1838705, a specific inhibitor for IGF-1R/INSR and DDR1-IN-1, an inhibitor for DDR1 (Sabbatini, P. et al., "GSK1838705A inhibits the insulin-like growth factor-1 receptor and anaplastic lymphoma kinase and shows antitumor activity in experimental models of human cancers", (2009) *Mol. Cancer Ther.* 8:2811-20; Kim, H. G. et al., "Discovery of a potent and selective DDR1 receptor tyrosine kinase inhibitor" (2013) *ACS Chem. Biol.* 8: 2145-50). GSK1838705, but not DDR1-IN-1, inhibited the proliferation of MCF-7 in a dose-dependent manner while neither inhibitor had an effect on the remaining breast cancer cell lines (FIG. 11A). This result indicates that IGF-1R/INSR plays a more important role than DDR1 in promoting MCF-7 cell proliferation.

Figure 11B:
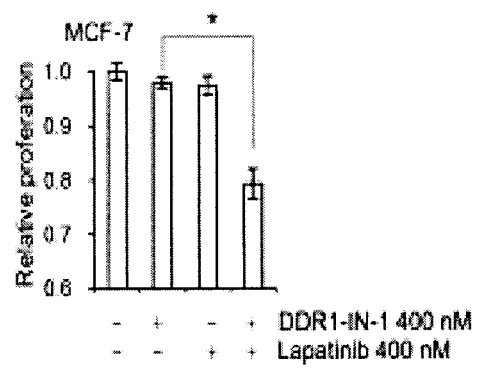
FIG. 11B is a bar graph showing the proliferation of MCF-7 cells, relative to no drug exposure, when exposed to 400 nM DDR-1N-1, 400 nM lapatinib, or 400 nM of both inhibitors, with * indicating a statistically-significant difference (p<0.001) and each assay conducted in triplicate.
Figure 11C:
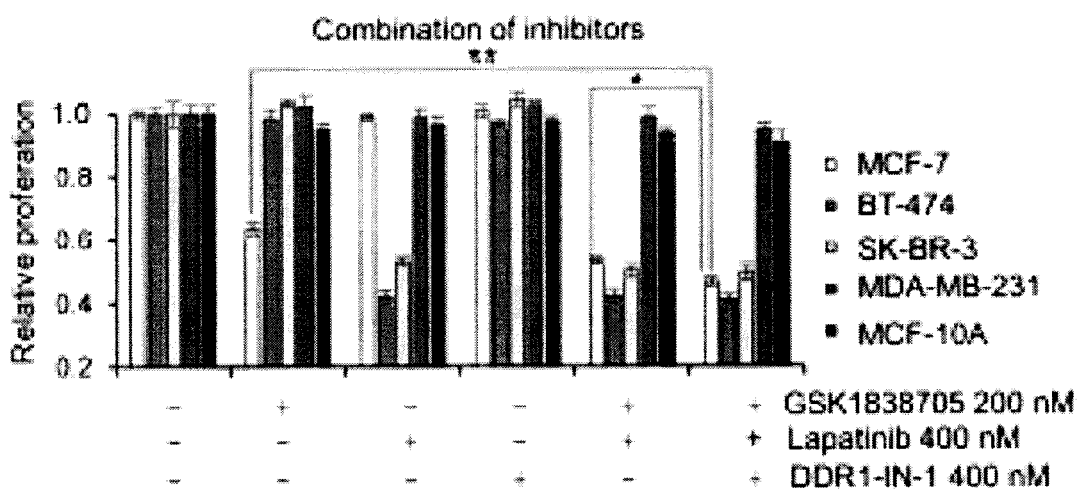
FIG. 11C are bar graphs showing the proliferation of the same cell lines as FIG. 11A and the cell line MCF-10A, relative to no drug exposure, when exposed to 200 nM GSK1838705, 400 nM DDR-1N-1, 400 nM lapatinib, or combinations thereof, with * and ** indicating statistically-significant differences (*, p<0.001; **, p<0.0001) and each assay conducted in quadruplicate.

To determine if DDR1 cooperates with other activated TKs to confer a growth advantage on MCF-7 cells, ted MCF-7 cells were incubated with DDR1-IN-1 together with lapatinib and/or GSK1838705. In contrast to the insensitivity of MCF-7 cells to singular inhibition of DDR1 or ErbB2, combined inhibition of the two kinases significantly reduced proliferation (FIG. 11B). Remarkably, triple inhibition of DDR1, ErbB2 and IGF-1R/INSR further decreased the proliferation of MCF-7 cells but had no effect on MCF-10A cells (FIG. 11C).

These data suggest that quantitative kinase activity profiling enabled by Superbinder-based phosphoproteomics may be used to inform cancer treatment to specifically target activated kinases or combinations thereof.

Example 9—TK Activity Profiling During Acquisition of Drug Resistance

Figure 4:
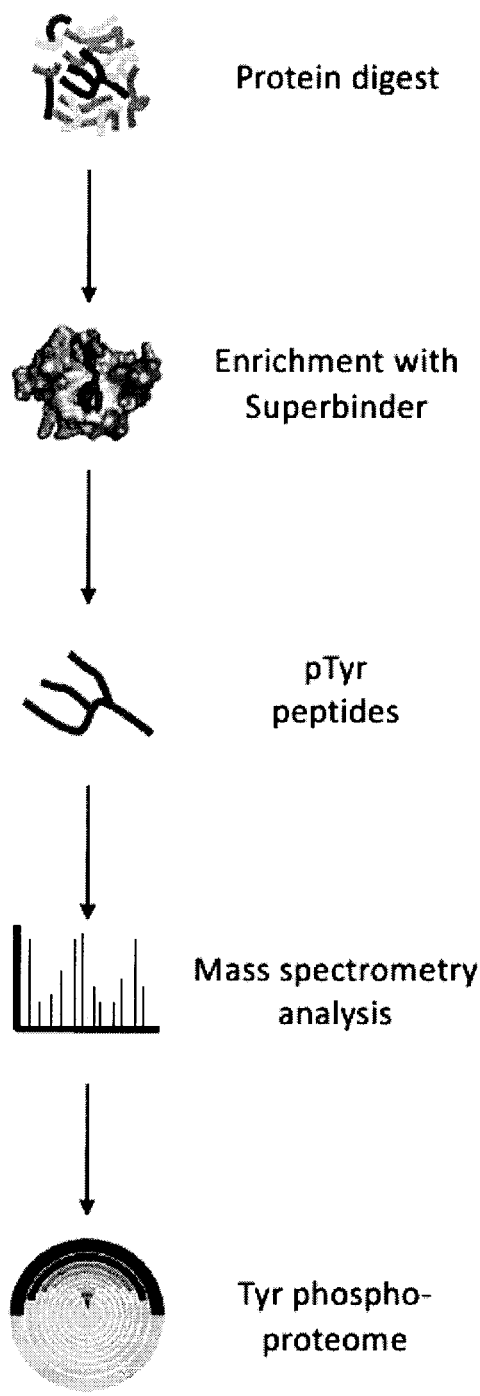
FIG. 4 is a flowchart for a method for profiling of protein tyrosine phosphorylation, including Tyr phosphosites in the activation loops of protein kinases and ITRMs, according to an embodiment of the present disclosure.

Superbinder-based enrichment of pTyr-including peptides was combined with scheduled MRM or PRM mass spectrometry, as depicted in the workflow in FIG. 4, to profile TK activity during the acquisition of drug resistance in cultured cells.

SK-BR-3 cells were grown in RPMI 1640 medium supplemented with 10% FBS, 100 µg/ml penicillin/streptomycin and L-glutamine. Cells were incubated at 37° C. in a humidified atmosphere containing 5% carbon dioxide.

To promote trastuzumab-resistance, SK-BR3 cells were continuously cultured in a medium containing 4 µg/ml (group 1) or 8 µg/ml(group 2) trastuzumab for 3-6 months while cell proliferation was monitored by MTT assay. Resistant clones from the two groups were then pooled and maintained in 4 µg/ml trastuzumab.

The cultured cells were homogenized and lysed in cold lysis buffer (8 M urea, 50 mM Tris-HCl pH7.4, 2% protease cocktail (v/v, Sigma P8340), 1% Triton X-100, 1 mM C3H7Na2PO6, 1 mM Na4O7P2, 1 mM NaF). Cell debris was removed by centrifugation and the supernatant was transferred to fresh tubes. Then a 5× volume of ice-cold precipitation solution (acetone/ethanol/acetic acid=50:50:1, v/v/v) was mixed with the clarified cell lysate and vortexed immediately. The mixture was incubated for at least 60 minutes at −20° C. and subsequently centrifuged at 15,000 g for 30 minutes at 4° C. to isolate precipitated protein. The protein pellet was washed with 75% ice-cold ethanol then air-dried for 5 minutes to allow the ethanol to evaporate.

The protein was first dissolved in 8 M urea prepared in mass-spectrometry(MS)-grade water. After reduction by dithiothreitol (DTT) and alkylation by iodoacetamide (IAA), the protein was digested by trypsin according to the manufacturer's protocol. Digested product was desalted in a C18 column and dissolved in ice-cold immunoaffinity purification (IAP) buffer containing 50 mM Tris-HCl (pH 7.2), 50 mM NaCl and 10 mM Na2HPO4. For enrichment of pTyr-including peptides, SH2 Superbinder (His$_6$/GST-tagged TrM Src SH2, SEQ ID NO:11) immobilized on Sulfolink Sepharose beads (ThermoFisher) was incubated with the peptides in IAP buffer and mildly rotated for four hours at 4° C. After three times washing in IPA buffer, 2.5% trifluoroacetic acid (TFA) was added to release the bound peptides from the agarose beads. The eluate was desalted on C18 column and re-dissolved in 0.1% formic acid. The peptides were subjected to MS analysis.

From the 126 potential TK regulatory sites identified in Example 7, 67 peptides were selected for analysis by MRM from the Tyr-including TK activation loop peptides listed in Table 8 that were longer than 8 amino acids. The Tyr-phosphorylated version of these peptides were synthesized in vitro and used to determine the retention time and to optimize MS detecting parameters in the QTRAP-4000 hybrid triple quadrupole/liner ion trap LC/MS system. From this, a retention time-scheduled multiple reaction monitoring (sMRM) method was established.

All MS experiments were performed by sMRM on an AB SCIEX 4000 QTRAP system equipped with a Waters nano-ACQUITY UPLC. The schedule and collision condition were optimized for the activation loop peptides using the corresponding synthetic peptides. For absolute quantification of the activation loop peptides, the corresponding stable isotope-labelled forms were also synthesized. A defined amount of these peptides were mixed with the digested products and co-purified by the Src superbinder. The isotope-labelled peptides served as internal standards in the MS analysis. The relative amounts of the activation loop peptides were determined by Skyline software based on the corresponding peak areas in the MRM chromatogram (or TIC).

Figure 12A:
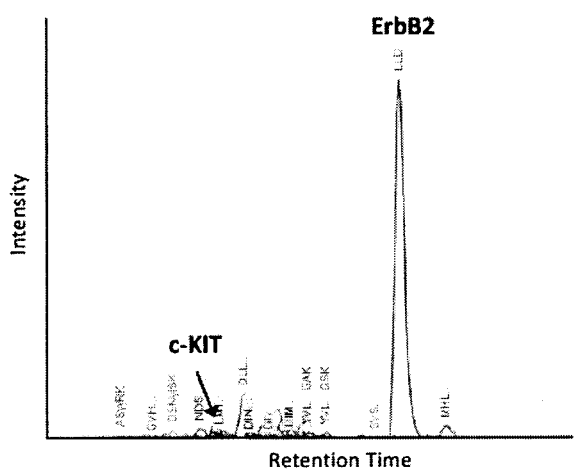
FIGS. 12A and 12B are line graphs depicting the mass spectra from total ion chromatography (TIC) from a Superbinder-MRM analysis of a trastuzumab-sensitive clone of SK-BR-3 cells (FIG. 12A) and a trastuzumab-resistant clone of SK-BR-3 cells (FIG. 12B), with the peaks corresponding to pTyr-including peptides in the activation loops of the ErbB2 (HER-2) RTK and the c-KIT RTK identified.
Figure 12B:
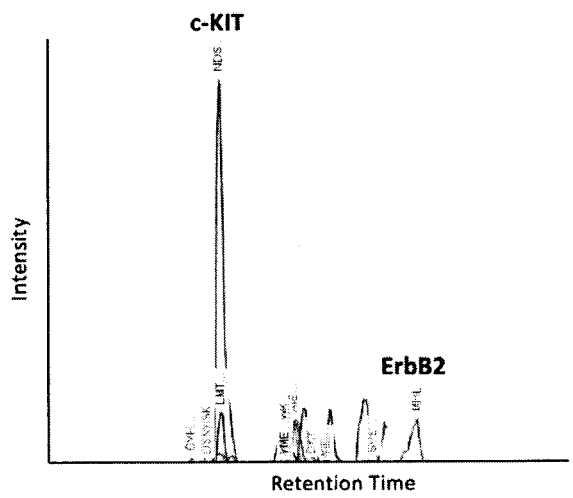
Figure 12C:
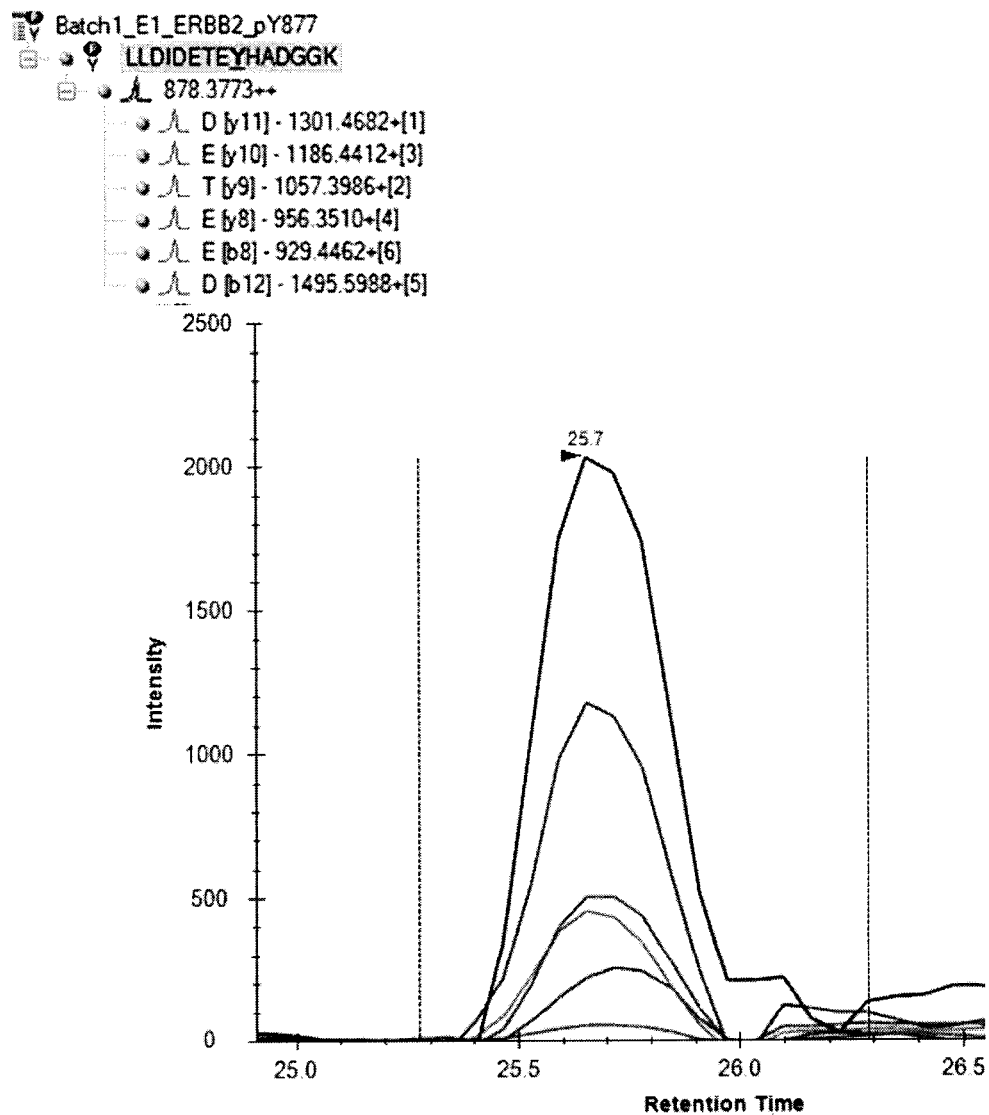
FIG. 12C is a line graph depicting the mass spectrum of a representative example of MRM analysis showing the daughter ions (panel above line graph) and the corresponding daughter ion spectra detected for an activation loop peptide of ErbB2 (HER2) comprising pY877.

The ErbB2 (HER2) activation loop was highly Tyr-phosphorylated in SK-BR-3 cells (FIG. 12A). In the pooled trastuzumab-resistant clones, however, the ErbB2 (HER2) activation loop was no longer highly Tyr-phosphorylated but the activation loop of the RTK c-KIT was (FIG. 12B). Detected transitions for ErbB2-pY877 LLDIDETEpY-HADGGK are shown in FIG. 12C as an example of peptide identification by MRM.

Example 10—TK Activity Profiling can Predict Drug Sensitivity

The TK activity profiles from Example 9 predict drug sensitivity.

Figure 13A:
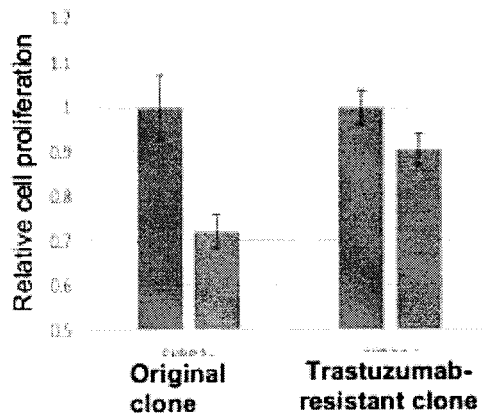
FIG. 13A is a bar graph showing the relative cell proliferation of the trastuzumab-sensitive clone (Original clone) of SK-BR-3 cells from FIG. 12A and the trastuzumab-resistant clone of SK-BR-3 cells from FIG. 12B, after 48 hours of exposure to no trastuzumab (blue bars) or 4 µg/ml trastuzumab (orange bars)

The original SK-BR-3 clone had high ErbB2 (HER2) activity (FIG. 12A) and was sensitive to trastuzumab (FIG. 13A), while the pool of trastuzumab-resistant clones (referred to here-in as the singular "clone") had lower ErbB2 (HER2) activity (FIG. 12B) and was less sensitive to trastuzumab (FIG. 13A).

Figure 13B:
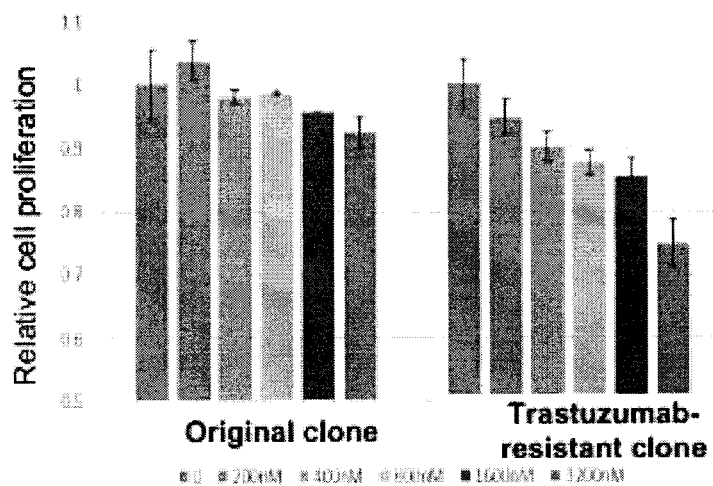
FIG. 13B is a bar graph showing the relative cell proliferation of the same clones in FIG. 13A after 48 hours of exposure to 0 nM (light blue), 200 nM (orange), 400 nM (grey), 800 nM (yellow), 1600 nM (dark blue), or 3200 nM (green) imatinib.
Figure 13C:
FIG. 13C is a bar graph showing the relative cell proliferation of the same clones in FIG. 13A after 4 days of exposure to no drug (Ctrl, blue), 4 µg/ml trastuzumab (red), 2 µM imatinib (green), or both 4 µg/ml trastuzumab and 2 µM imatinib (purple)

Similarly, high c-KIT activity in the trastuzumab-resistant clone (FIG. 12B) correlated with a greater sensitivity to imatinib (FIG. 13B), a c-KIT/Abl kinase inhibitor, relative to the original SK-BR-3 clone in which c-KIT was not highly active (FIG. 12A). The trastuzumab-resistant clone was also significantly more sensitive to combined inhibition of ErbB2 (HER2) and c-KIT by a trastuzumab and imatinib cocktail (FIG. 13C).

Drug sensitivity was measured by MTT cell proliferation assays.

Example 11—Profiling TK Activity in Fast-Frozen Solid Tumour Specimens with Superbinder Affinity Purification Followed by Scheduled PRM (SAP-PRM)

Figure 14A:
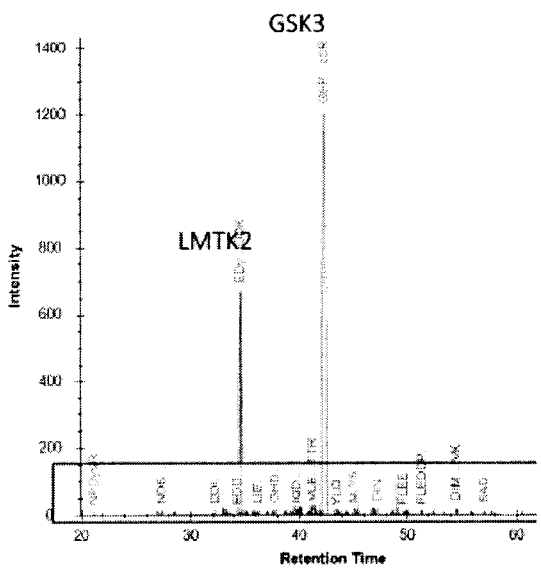
FIGS. 14A, 14C, and 14D are line graphs each depicting a mass spectrum from a scheduled PRM analysis of a Superbinder affinity purification (SAP) of 30 µg of tryptic protein digest; the three protein digests were from three fast-frozen, triple-negative (ER-/PR-/HER2-) breast cancer specimens; a pTyr-including peptide in the activation loop of endogenous GSK3 served as an internal control (GSK3 α and GSK3β have the same pTyr-including peptide)
Figure 14B:
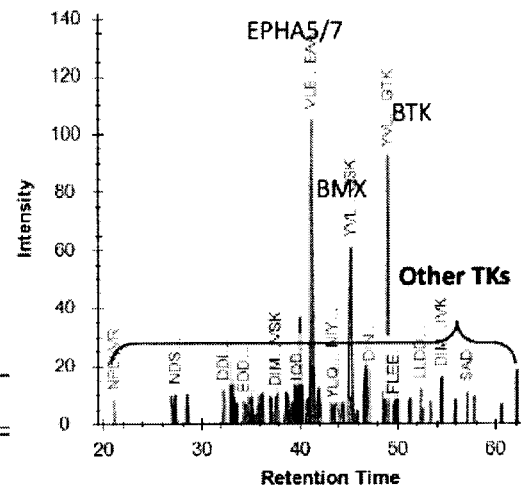
FIG. 14B is the same mass spectrum as in FIG. 14A but showing the less activated TKs, as the LMTK2 and GSK3 peaks have been removed and the y-axis reduced (corresponding approximately to the boxed-in area in FIG. 14A)
Figure 14C:
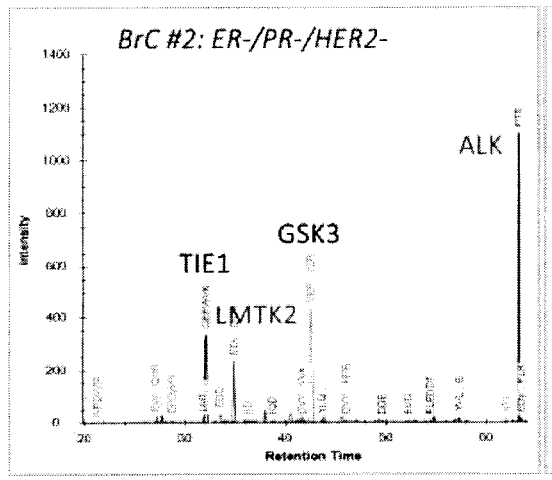
Figure 14D:
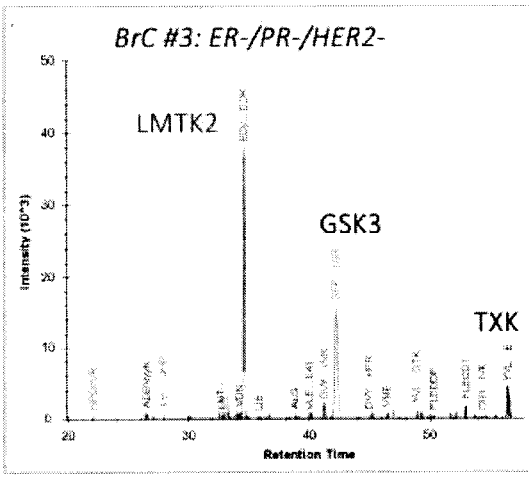

TK activity was profiled in three samples of fast-frozen (frozen in liquid nitrogen within 30 min of surgical excision), triple-negative breast cancer (TNBC) biopsy using SAP-PRM. Triple-negative breast cancer (ER-/PR-/HER2-) is characterized by the absence of expression of the estrogen receptor (ER) and progesterone receptors (PR), as well as the lack of amplification of the HER2 gene. LMTK2 was detected as the most activated TK other than the internal control GSK3 based on the peak areas of the corresponding activation loop peptides (FIG. 14A) and can be observed in all three samples (FIGS. 14A, C and D). When these two peaks are removed from one sample and the scale reduced (FIG. 14B), less activated TKs can be observed (e.g., EPHA5/7, BMX, BTK).

Figure 15A:
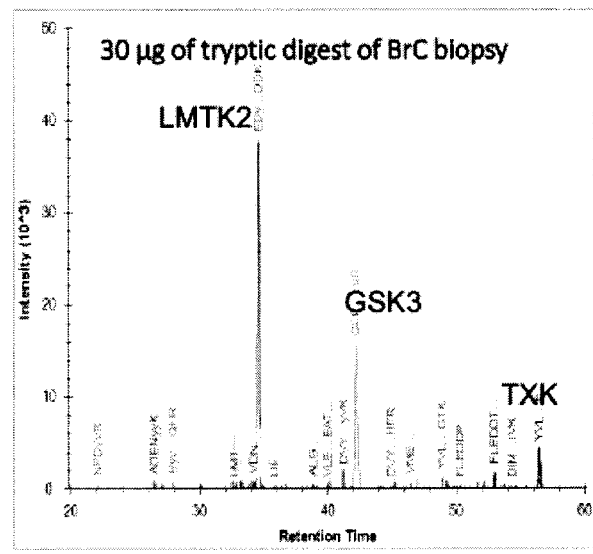
FIG. 15A is a line graph depicting a mass spectrum from a scheduled PRM analysis of a Superbinder affinity purification (SAP) of 30 µg of tryptic protein digest of the triple-negative (ER-/PR-/HER2-) breast cancer specimen from FIG. 14D.
Figure 15B:
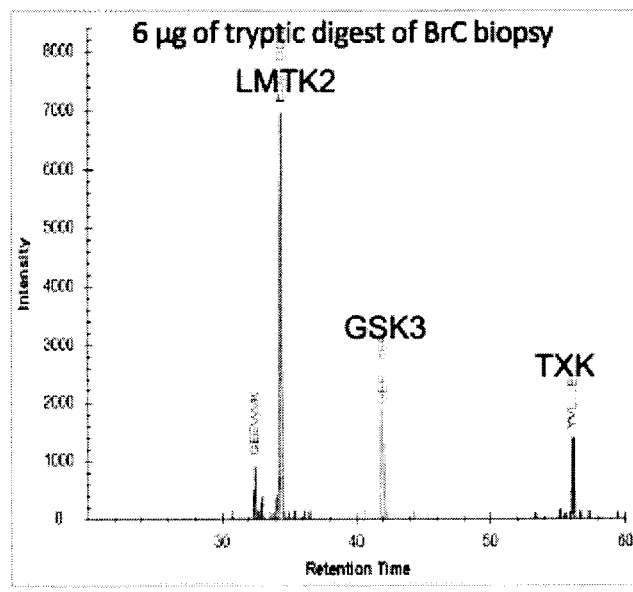
FIG. 15B is a line graph depicting a mass spectrum from SAP-PRM analysis of 6 μg of the same tryptic protein digest as was used to obtain the spectrum in FIG. 15A.
Figure 16A:
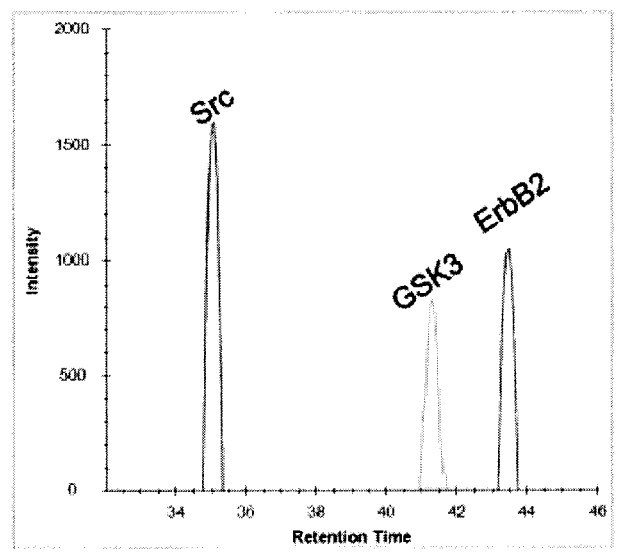
FIGS. 16A and 16B are line graphs, each depicting a mass spectrum from SAP-PRM analysis of a different 2 μg aliquot of a tryptic protein digest from SK-BR-3 cells.
Figure 16B:
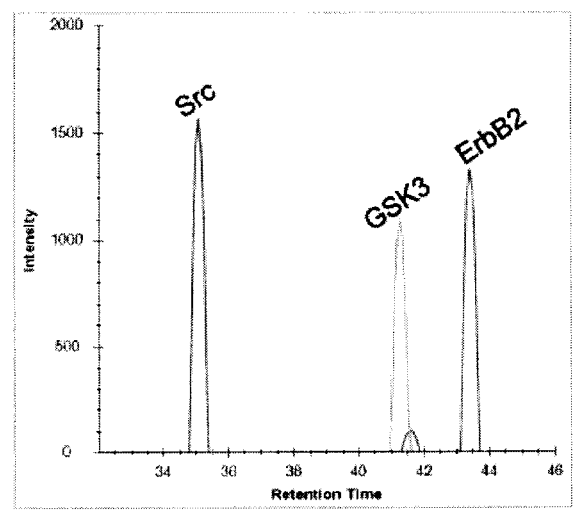

SAP-PRM analysis can be highly sensitive. The TK activity profiles in FIGS. 14A-D were each obtained by SAP-PRM analysis of 30 µg of tryptic protein digest from a breast cancer biopsy. But SAP-PRM analysis of 6 µg of tryptic protein digest (FIG. 15B) from one of the biopsies identified the major peaks (e.g., LMTK2, GSK3, TXK) in the original profile (FIG. 15A). Furthermore, SAP-PRM analysis of just 2 µg of tryptic protein digest from SK-BR-3 cells reproducibly identified three activated TKs (FIGS. 16A-B).

The TK activity profiles in FIGS. 14-16 were obtained by a SAP-PRM analysis as follows.

Tissues and Cells:

Tumour biopsies from three patients with triple-negative breast cancer, were rapidly frozen in liquid nitrogen and stored in liquid nitrogen. Fresh cultured SK-BR-3 cells were used.

Clarified Lysate from Each Biopsy and Cell Sample:

For the frozen biopsies, a suitably-sized sample was cut from the frozen biopsy in a mortar pre-cooled in liquid nitrogen. The biopsy sample was then ground in a micro-tissue grinder with 300 µL of 4° C. freshly-prepared lysis buffer (8 M urea, 2% protease inhibitor cocktail (v/v, Sigma P8340), 50 mM Tris-HCl (pH 7.6), 1 mM $Na_3VO_4$). SK-BR-3 cells were processed the same way as described in Example 9.

The tissue and cell lysates were transferred into fresh 1.7 mL micro-centrifuge tubes and mixed by rotating for 10 min at 4° C. The tubes were then sonicated in a water bath with ice, followed by centrifugation at 20,000 relative centrifugation force (rcf) for 15 min at 4° C. The supernatants (clarified lysates) were transferred to fresh 1.7 mL micro-centrifuge tubes.

Collecting Protein from Clarified Lysates:

A 5× volume of cold precipitation solution (acetone/ethanol/acetic acid at 50/50/0.1, v/v/v) was added to each clarified lysate and the tube immediately vortexed. The tubes were incubated for at least 2 hr at −20° C. and subsequently centrifuged at 20,000 rcf for 15 min at 4° C. to pellet the protein. The supernatants were removed, and 1 mL of cold 75% ethanol was added to each tube, followed by vortexing. The tubes were again centrifuged at 20,000 rcf for 15 min at 4° C. The supernatants were removed, and the protein pellets were air-dried for 1 min. To obtain protein solutions, 100 µL of 8 M urea or 6 M guanidine hydrochloride (GuHCl) was added to each tube, followed by rotation or sonication to redissolve the protein pellet.

Preparing Tryptic Protein Digests:

To each protein solution, DTT was added to 5 mM final concentration, and the tubes were rotated for 1 hr at room temperature. Next, fresh 1 M iodoacetic acid was added to each protein solution to a final concentration of 14 mM, and the tubes were rotated in the dark for 1 hr at room temperature. Then, to quench unreacted iodoacetic acid, more DTT was added to each protein solution to increase the final DTT concentration by a further 5 mM, and the tubes were rotated for 1 hr at room temperature. The protein concentration in each protein solution was then determined.

Each protein solution was diluted with a solution of 50 mM Tris (pH 7.6) and 5 mM $CaCl_2$ such that the final urea concentration was less than 2 M or the final GuHCl concentration was less than 1M. Next, trypsin was added to each diluted protein solution to achieve a 1:20 molar ratio of trypsin:protein, and the tubes were rotated/shaken for 16 hr at 37° C. Then, TFA was added to each trypsin/protein solution to a final concentration of 1% (v/v), and the tubes were centrifuged at 20,000 rcf for 15 min at 4° C. to pellet the trypsin. The supernatants were each loaded onto and flowed through a conditioned C18 desalting column. Then, each column was washed with 0.1% TFA, and peptides were eluted with 80% ACN to obtain a tryptic protein digest for each sample.

Superbinder Affinity Purification:

Superbinder protein (His$_6$/GST-tagged TrM Src SH2, SEQ ID NO:11) was immobilized on Sulfolink Sepharose beads (Thermo Fisher) at a concentration of 10 µg protein per µL of beads.

Each tryptic protein digest was dissolved in 500 µL of IAP buffer as in Example 9 in a 1.7 mL micro-centrifuge tube. For protein samples that were less than 500 µg prior to tryptic digestion, 200 µg of Superbinder protein (20 µL beads) was added. For protein samples that were more than 500 µg (up to a few milligrams) prior to tryptic digestion, 400 µg of Superbinder protein (40 µL beads) was added. The tubes were rotated for 4 hr at 4° C., and then centrifuged to spin the beads down. The supernatant was removed from each tube. The beads in each tube were washed 4 times in 500 µL of IAP buffer by pipetting the beads up and down a few times, followed by spinning the beads down and removing the supernatant. Next, the beads in each tube were resuspended in 5% TFA, incubated at room temperature for 10 min, and then spun down. The supernatants were each transferred to a fresh tube and then vacuum dried. The dried peptide samples were each dissolved in water and centrifuged at 20,000 rcf for 15 min at 4° C. to remove any particles. The supernatants were each transferred to a mass spectrometry sample vial.

Detection of Target pTyr-Including Peptides:

A Q-Exactive Hybrid Quadrupole-Orbitrap mass spectrometer equipped with an Easy-nLC1000 liquid chromatography system (Thermo Fisher Scientific) was used for the PRM analysis. Enriched peptides by SAP were separated by liquid chromatography with a liner gradient of solvents A (0.1% formic acid in water) to B (0.1% formic acid in acetonitrile). Peptides were firstly loaded into a nanoViper trap column (C18, 3 µm, 100 Å, 75 µm×20 mm, Thermo Fisher) and then separated in an EASY-Spray analytical column (C18, 2 µm, 100 Å, 75 µm×500 mm, Thermo Fisher) with a pre-built electrospray emitter. Peptides were eluted at a flow rate of 300 nL/min, using with a liner gradient of 3% to 35% B in 45 minutes, followed by 35% to 95% B in 8 minutes. Finally, the column was washed for 7 minutes with 95% B. Data were acquired in a scheduled parallel reaction monitoring (PRM) method in the Q-Exactive and targeted peptides were listed in the inclusion list with default charge +2 in the Xcalibur software. The MS2 scanning was set at a resolution of 17,500 (at m/z 200), AGC target 2×10$^5$, maximum injection time 250 ms, isolation window 2.5 m/z and normalized collision energy of 27.

Example 12—Profiling TK Activity in Liquid Tumour Specimens with Superbinder Affinity Purification Followed by Scheduled PRM (SAP-PRM)

Figure 17A:
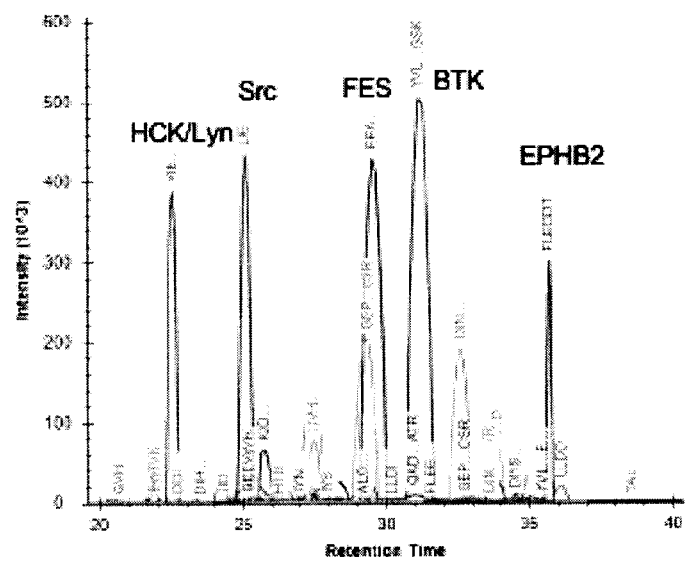
FIG. 17A is a line graph depicting a mass spectrum from a scheduled PRM analysis of a Superbinder affinity purification (SAP) of 90 μg of tryptic protein digest; the protein was isolated from a fast-frozen peripheral blood sample of an acute myeloid leukemia (AML) patient.
Figure 17B:
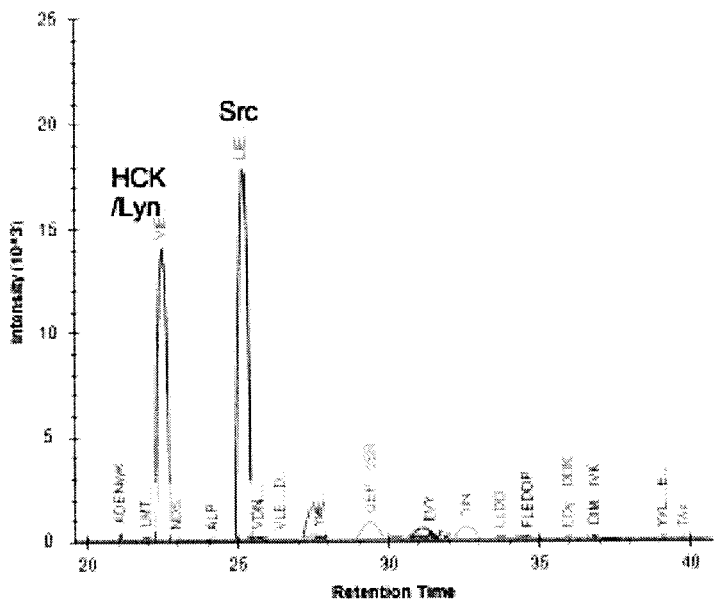
FIG. 17B is the mass spectrum from an SAP-PRM analysis of a blood sample (~30 μg of tryptic protein digest) from a normal individual, using the same procedure as used to obtain FIG. 17A.

Mononuclear cells from peripheral blood of an acute myeloid leukemia (AML) patient and a normal individual were provided by the Victoria Hospital (London, Ontario, Canada) for kinome profiling analysis using the SAP-PRM method. An analysis of 90 µg of protein digest from the AML sample showed identified HCK/Lyn, Src, FES, BTK and EPHB2 as highly activated (FIG. 17A). An analysis of the control sample (20 µg protein digest) from the healthy individual identified only HCK/Lyn and Src as the activated TKs (FIG. 17B).

Example 13—Profiling the Effect of Checkpoint Inhibitors with Superbinder Affinity Purification Followed by Scheduled PRM (SAP-PRM)

An application of the present disclosure is to determine the mechanism of action or pharmacodynamics of an immune regulatory drug such as PD-1 or PD-L1 inhibitors. Several of such inhibitors have been FDA approved for use in cancer patients. A limitation of immune checkpoint inhibitor-based therapies is that the mechanism of action for such therapies are not fully understood, which underlies the difficulty with which to predict patient response to a given immune checkpoint therapy.

Figure 18A:
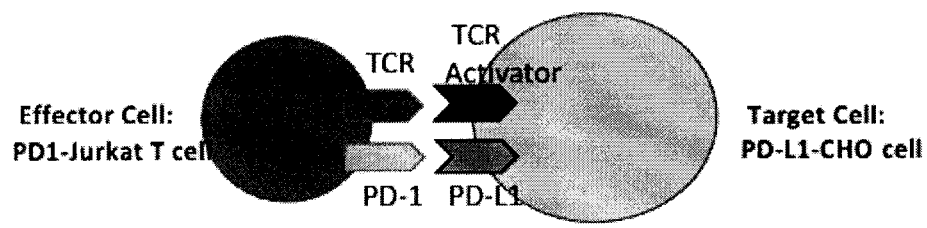
FIG. 18A is a graph depicting a cellular system developed by BPS Bioscience (CA, USA) for assaying PD-1/PD-1 interaction and characterizing the effect of PD-1 or PD-L1 inhibitors.
Figure 18B:
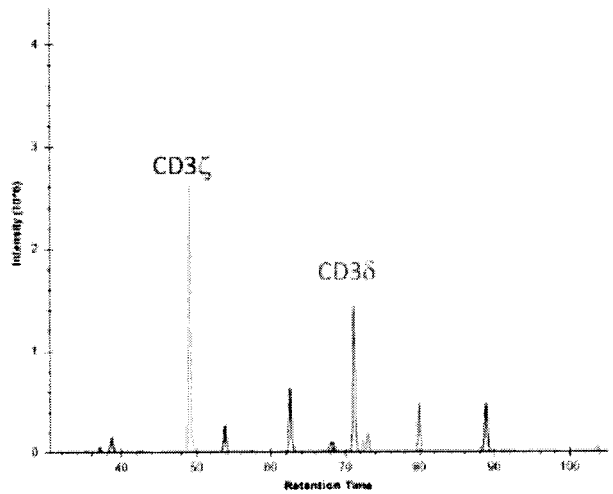
FIG. 18B is a line graph depicting a mass spectrum from a scheduled MRM analysis of an Superbinder affinity purification (SAP) of 50 μg of tryptic protein digest; the protein digest was from PD-1 expressing Jurkat T cells co-cultured with PD-L1 expressing CHO cells.
Figure 18C:
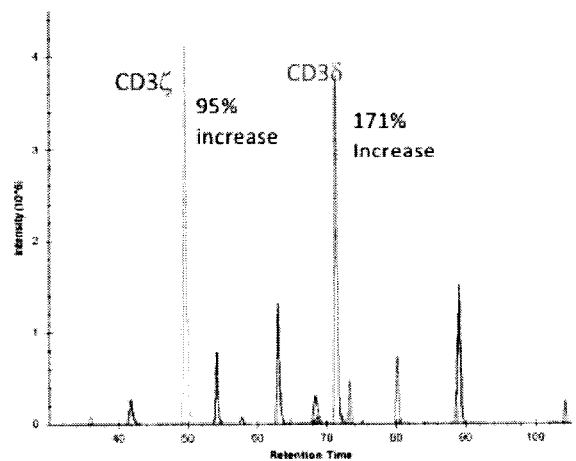
FIG. 18C is the mass spectrum of protein digest from the same cells as in FIG. 18B but treated overnight with an anti-PD-L1 antibody (BPS Bioscience)

Several companies, BPS Bioscience included, have developed in vitro cellular systems for the evaluation of PD-1 or PD-L1 inhibitors (i.e. antibodies that inhibit the interaction between PD-1 and PD-L1) (FIG. 18A). In this system, PD-1 expressing Jurkat cells can be co-cultured with PD-L1 expressing CHO cells in the absence or presence of an inhibitory antibody to determine the effect of the inhibitor on the activation of the Jurkat T cells. SAP-PRM analysis of the PD-1 expressing Jurkat T cells detected increased Tyr phosphorylation of the ITAM peptides in the TCR co-receptors CD3δ and CD3ζ in the presence of an anti-PD-L1 antibody (BPS Bioscience) (FIG. 18C) as compared to that in cells without the antibody (FIG. 18B).

This finding expands the application of immune profiling to other cells or tissue samples according to the presence disclosure. An analysis of immunoreceptors identifies 195 ITRM (including ITAM, ITIM and ITSM) sequences (Table 2) that can be detected by the SAP-PRM or SAP-MRM method. It can be expected that immune profiling based on systematic identification of ITRM phosphorylation using the SAP-PRM/MRM method will provide a global view of the immune system. Furthermore, quantitative changes in the ITRM phosphorylation between disease tissues and normal controls or between specimens obtained before and after a treatment will provide valuable information about disease mechanism and mechanism of action for an immune regulatory drug.

Figure 19A:
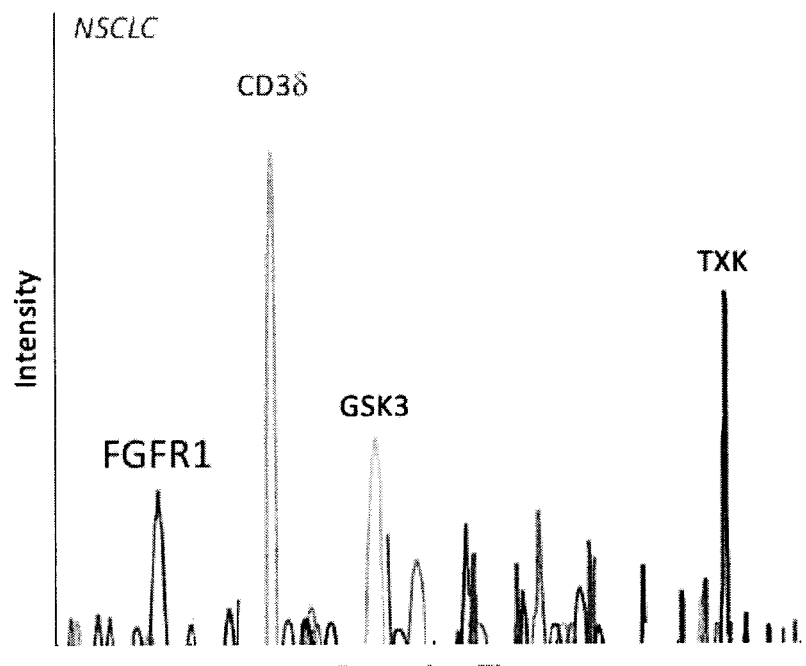
FIGS. 19A and 19B are line graphs each depicting a mass spectrum from a scheduled PRM analysis of an Superbinder affinity purification (SAP) of a formalin-fixed, paraffin-embedded (FFPE) tumor biopsy.
Figure 19B:
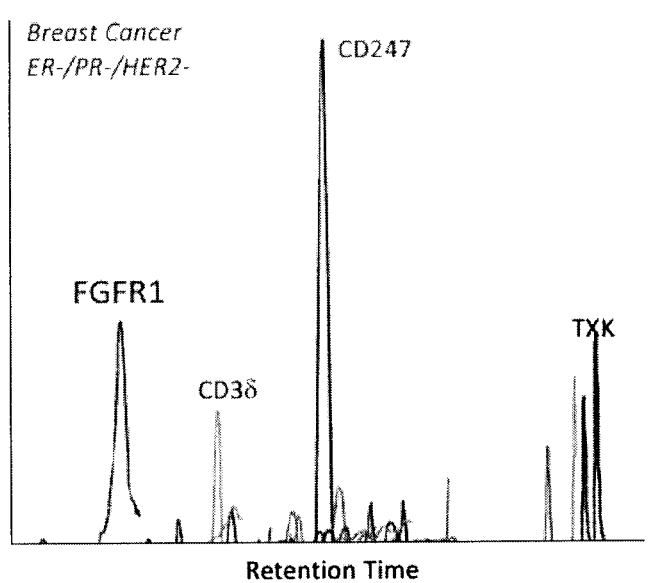

Example 14—Simultaneous Profiling TK Activity and Infiltrated T Cells in Formalin-Fixed, Paraffin-Embedded (FFPE) Tumor Specimens SAP-PRM analysis was able to profile activated TKs and infiltrated T cells in an FFPE non-small cell lung cancer biopsy (FIG. 19A) and an FFPE breast cancer biopsy (FIG. 19B)

This finding expands the application of TK and immune profiling according to the present disclosure. As one example, the ability to profile TK activity in FFPE biopsies may allow for retrospective study of how treatments (e.g., radiation, drugs) and treatment outcomes (e.g., remission, death) correlate with TK activities in a range of different cancers and other illnesses. Samples from biopsies are routinely fixed with formalin and embedded in paraffin for histological analysis. Such samples are often archived by health-care facilities and may be available for TK profiling. The ability to profile both TK and infiltrated T cells may allow for the design of combo therapies that target both the activated TKs and the immune checkpoints.

The TK activity profiles in FIGS. 19A and B were obtained by a SAP-PRM analysis as follows.

Collecting FFPE Samples:

The FFPE biopsy samples were each embedded in a 5 μm thick slab of paraffin mounted on a microscope slide. The slides were de-waxed by consecutively immersing them in three fresh jars of xylene followed by three fresh jars of ethanol. De-waxing exposed the biopsy samples, which were collected and transferred to separate 1.7 mL microcentrifuge tubes.

Clarified Lysates from FFPE Samples:

200 μL of freshly-prepared lysis buffer (6 M GuHCl, 50 mM Tris-HCl (pH 7.6), 50 mM DTT) was added to each tube. The tubes were placed in boiling water for 20 min, followed by heating at 80° C. for 2 hr. Next, the tubes were centrifuged at 20,000 rcf for 15 min at 4° C. to remove any undissolved debris, and then the supernatants (clarified lysates) were each transferred to a fresh 1.7 mL microcentrifuge tube.

The remaining steps in the SAP-PRM analysis of the FFPE samples were conducted as in Example 12, beginning at the stage Collecting protein from clarified lysates, with one exception. The exception was in the stage Preparing tryptic protein digests, where the initial step of adding DTT to 5 mM to the redissolved protein and rotating the tubes for 1 hour was skipped for the FFPE samples.

Example 15—Analysis of a Mixture of pTyr-Including Peptides Derived from TK Activation Loops Equal molar amounts (10 nmole) of the wild-type (wt) human Src SH2 domain and the DM and TrM human Src SH2 Superbinders (SEQ ID NO: 14 and 5, respectively) expressed with $His_6$ and GST tags were used to capture pTyr-including peptides from a mixture of 54 different pTyr-including peptides (10 pmole each) derived from 54 TK activation loops. The isolated peptides were identified by PRM and quantified based on the corresponding MS peak area. 1.8% of the eluted peptides were injected into a Q-Exactive (Thermo Fisher) preceded with a nano-LC system.

The TrM human Src SH2 Superbinder captured all 54 pTyr-including peptides in the mixture, which were simultaneously detected by PRM (Table 9). In contrast, the DM human Src SH2 Superbinder detected 32 of the 54 pTyr-including peptides, whereas the wt SH2 domain detected only 22 of the 54 pTyr-including peptides (Table 9). Except for one pTyr-including peptide, the TrM human Src SH2 Superbinder captured more, and in most cases far more, pTyr-including peptides than the wt human Src SH2 domain (Table 9). In general, the DM human Src SH2 Superbinder captured more pTyr-including peptides than the wt human Src SH2 domain (Table 9).

Figure 20:
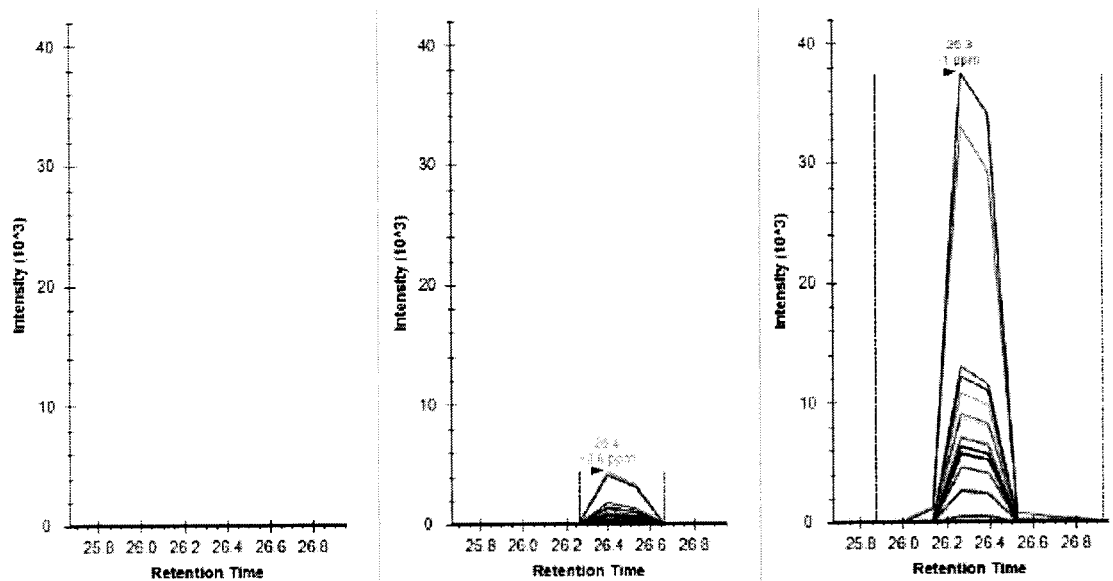
FIG. 20 is a line graph depicting the mass spectra of daughter ions detected for the pTyr-including peptide from the activation loop of the tyrosine kinase EPHA8. The spectra were recorded on a Q-Exactive Mass Spectrometer running in scheduled PRM mode. A mixture of 54 different pTyr-including peptides (10 pmole each) derived from TK activation loops (Table 9) was subjected to wild-type SH2 domain or Superbinder affinity purification (SAP) followed by scheduled PRM analysis. Equal molar amounts (10 nmole) of the wild-type (wt) human Src SH2 domain and the DM and TrM human Src SH2 Superbinders (SEQ ID NO: 14 and 5, respectively) were used to capture pTyr-including peptides from the peptide mixture. Left, PRM spectrum from wt SH2 domain purification which showed no signal for the EPHA8 pTyr793 peptide; Middle, PRM spectrum obtained from the DM human Src Superbinder affinity purification; Right, PRM spectrum obtained from the TrM human Src Superbinder affinity purification. The different lines represent different daughter ions produced by the EPHA8 pTyr793 peptide.

For the EPHA8 (pTyr793) peptide, one of the pTyr-including peptides profiled in the mixture of 54 pTyr-including peptides, FIG. 20 shows the mass spectra of daughter ions detected for EPHA8 (pTyr793) by both the DM and TrM human Src SH2 Superbinders, in contrast to none detected when using the wt human Src SH2 domain. This is one example that demonstrates the utility of using either the DM or TrM human Src SH2 Superbinders affinity purification (SAP) followed by scheduled PRM analysis in profiling protein tyrosine phosphorylation, which is expected based on the enhanced binding affinity of the Superbinders relative to the parent SH2 domains.

TABLE 9

Double mutant (DM) and triple mutant (TrM) human Src SH2 Superbinders capture more pTyr-including peptides than the parent human Src SH2 domain (wt).

| Kinase name (Tyr phosphosite) | Sequence of pTyr-including peptide | Fragment Ion | PRM signal peak area | | |
|---|---|---|---|---|---|
| | | | wt | DM | TrM |
| FGFR3 (pTyr647/648) | DVHNLDpYpYK | b3 | 103,678 | 64,641 | 258,435 |
| ROR2 (pTyr645/646) | EVYAADpYpYK | y5 | 85,894 | 60,460 | 334,295 |
| JAK1 (pTyr1034/1035) | EpYpYTVK | y2 | 58,254 | 46,193 | 109,611 |
| FGFR2 (pTyr656/657) | DINNIDpYpYK | y4 | 51,625 | 39,469 | 87,143 |
| DDR1 (pTyr796/797) | NLYAGDpYpYR | b2 | 47,729 | 43,173 | 337,871 |
| MUSK (pTyr755/756) | NIYSADpYpYK | y2 | 47,647 | 0 | 178,086 |
| ERBB3 (pTyr866) | QLLpYSEAK | y2 | 41,881 | 151,587 | 164,128 |
| NTRK2 (pTyr706/707) | DVYSTDpYpYR | y4 | 39,632 | 22,794 | 114,762 |
| ROR1 (pTyr645/646) | EIYSADpYpYR | y6 | 32,356 | 27,661 | 177,244 |
| LMTK3 (pTyr296/297) | EDpYpYLTPER | y3 | 29,887 | 78,610 | 375,974 |
| FGFR4 (pTyr642/643) | GVHHIDpYpYK | b3 | 29,764 | 29,983 | 36,105 |
| FGFR1 (pTyr653/654) | DIHHIDpYpYK | b6 | 28,495 | 28,967 | 51,243 |
| MET (pTyr1234/1235) | EpYpYSVHNK | y2 | 26,824 | 70,811 | 111,218 |
| JAK3 (pTyr980/981) | DpYpYVVR | y2 | 23,291 | 10,521 | 19,712 |
| NTRK1 (pTyr680/681) | DIYSTDpYpYR | b2 | 21,736 | 30,204 | 103,368 |
| DDR2 (pTyr740/741) | NLYSGDpYpYR | y6 | 15,251 | 16,232 | 184,684 |

TABLE 9-continued

Double mutant (DM) and triple mutant (TrM) human Src SH2 Superbinders capture more pTyr-including peptides than the parent human Src SH2 domain (wt).

| Kinase name (Tyr phosphosite) | Sequence of pTyr-including peptide | Fragment Ion | PRM signal peak area | | |
|---|---|---|---|---|---|
| | | | wt | DM | TrM |
| TYK2 (pTyr1054/1055) | AVPEGHEpYpYR | y6 | 11,551 | 9,679 | 53,473 |
| EPHB2 (pTyr780) | FLEDDTSDPTpYTSALGGK | Y3 | 10,833 | 98,045 | 215,302 |
| RON (pTyr1238/1239) | EpYpYSVQQHR | y4 | 5,434 | 17,370 | 44,290 |
| BTK (pTyr551) | YVLDDEpYTSSVGSK | b2 | 4,214 | 18,246 | 1,311,693 |
| EPHA6 (pTyr830) | VLEDDPEAApYTTTGGK | b2 | 2,742 | 51,066 | 287,653 |
| TXK (pTyr420) | YVLDDEpYVSSFGAK | b2 | 1,519 | 46,128 | 271,650 |
| EPHA8 (pTyr793) | VLEDDPDAApYTTTGGK | y11 | 0 | 57,102 | 585,234 |
| JAK2 (pTyr221) | IQDpYHILTR | Y3 | 0 | 39,232 | 85,513 |
| EPHB3 (pTyr792) | FLEDDPSDPTpYTSSLGGK | y10 | 0 | 14,654 | 260,454 |
| EPHA1 (pTyr781) | LLDDFDGTpYETQGGK | y9 | 0 | 12,335 | 188,365 |
| INSRR (pTyr1145/1146) | DVYETDpYpYR | y5 | 0 | 7,794 | 20,796 |
| EPHA2 (pTyr772) | VLEDDPEATpYTTSGGK | y11 | 0 | 4,858 | 347,030 |
| PTK7 (pTyr960/961) | DVYNSEpYpYHFR | b2 | 0 | 4,843 | 8,863 |
| TEC (pTyr519) | YVLDDQpYTSSSGAK | b2 | 0 | 4,818 | 781,110 |
| ERBB2 (pTyr877) | LLDIDETEpYHADGGK | b3 | 0 | 4,642 | 42,655 |
| LMTK2 (pTyr295) | EDpYIETDDK | b2 | 0 | 1,124 | 20,896 |
| RET (pTyr905) | DVYEEDSpYVK | b2 | 0 | 0 | 882,529 |
| SRMS (pTyr380) | DDIpYSPSSSSK | y8 | 0 | 0 | 478,598 |
| TIE1 (pTyr1007) | GEEVpYVK | b2 | 0 | 0 | 409,242 |
| ITK (pTyr512) | FVLDDQpYTSSTGTK | y11 | 0 | 0 | 403,125 |
| PGFRB (pTyr857) | DSNpYISK | y2 | 0 | 0 | 398,271 |
| EPHA3 (pTyr779) | VLEDDPEAApYTTR | y8 | 0 | 0 | 394,218 |
| HCK (pTyr411) | VIEDNEpYTAR | b2 | 0 | 0 | 383,521 |
| FRK (pTyr387) | VDNEDIpYESR | y6 | 0 | 0 | 290,546 |
| KIT (pTyr823) | NDSNpYVVK | b2 | 0 | 0 | 234,665 |
| TIE2 (pTyr992) | GQEVpYVK | b2 | 0 | 0 | 209,701 |
| EPHB1 (pTyr778) | YLQDDTSDPTpYTSSLGGK | y10 | 0 | 0 | 205,974 |
| VGFR2 (pTyr1059) | DPDpYVR | Y3 | 0 | 0 | 196,659 |
| VGFR1 (pTyr1053) | NPDpYVR | y3 | 0 | 0 | 158,244 |
| BLK (pTyr389) | IIDSEpYTAQEGAK | b2 | 0 | 0 | 156,244 |
| BMX (pTyr566) | YVLDDQpYVSSVGTK | b2 | 0 | 0 | 151,470 |
| EPHB4 (pTyr774) | FLEENSSDPTpYTSSLGGK | y10 | 0 | 0 | 134,156 |
| SRC (pTyr419) | LIEDNEpYTAR | b2 | 0 | 0 | 99,515 |
| GSK3 (pTyr279/216) | GEPNVSpYICSR | y6 | 0 | 0 | 48,337 |
| FER (pTyr714) | QEDGGVpYSSSGLK | y7 | 0 | 0 | 27,417 |

TABLE 9-continued

Double mutant (DM) and triple mutant (TrM) human Src SH2 Superbinders capture more pTyr-including peptides than the parent human Src SH2 domain (wt).

| Kinase name (Tyr phosphosite) | Sequence of pTyr-including Fragment peptide | Ion | PRM signal peak area | | |
|---|---|---|---|---|---|
| | | | wt | DM | TrM |
| MERTK (pTyr753/754) | IYSGDpYpYR | b2 | 0 | 0 | 26,483 |
| FES (pTyr713) | EEADGVpYAASGGLR | y8 | 0 | 0 | 25,101 |

Shown are the amounts of pTyr-including peptides captured, based on the corresponding peak area of PRM signal, by each of the parent human Src SH2 domain and the DM and TrM human Src SH2 Superbinders.

Example 16—the QuadM-TrM Tandem Superbinder Captures More pTyr-Including Peptides than the TrM Human Src Superbinder A QuadM-TrM tandem Superbinder (SEQ ID NO: 15) was produced in *E. Coli* by expressing a recombinant DNA that contained the gene encoding the QuadM human Src Superbinder (SEQ ID NO: 12) in tandem with the gene encoding the TrM human Src Superbinder (SEQ ID NO: 5). Equal molar amounts (200 pmole) of the QuadM-TrM tandem Superbinder and the TrM human Src SH2 Superbinder were used to capture pTyr-including peptides from a mixture of 40 different pTyr-including peptides (200 fmole each) derived from ITRMs. The isolated peptides were identified by scheduled PRM and quantified based on the corresponding MS peak area.

Table 10 shows that improved capture of pTyr-including peptides was achieved by combining the two different SH2 Superbinders into a single Superbinder with tandem domains. In addition, of the top 10 pTyr-including peptides preferably captured by the QuadM-TrM tandem Superbinder, 8 lacked a hydrophobic residue at the pTyr+3 position. A hydrophobic pTyr+3 residue is preferred by the Src SH2 TrM but not by the QuardM. The QuardM Superbinder is similar in specificity to the Grb2 SH2 domain which prefers an Asn residue at the pTyr+2 position but has no apparent preference for the pTyr+3 position. The combination of the two Superbinders in tandem makes it possible to capture peptides that are preferably bound by both Superbinders. As a result of combining the two Superbinders into a single protein, the QuadM-TrM tandem Superbinder was capable of binding to more pTyr-including peptides with a hydrophilic residue at pTyr+3 than when the TrM human Src Superbinder.

TABLE 10

The QuadM-TrM tandem Superbinder captures more pTyr-including peptides than the TrM human Src Superbinder.

| Protein name_Tyr phosphosite | Sequence of pTyr-including peptide | Amino Acid Position | | (QT-TrM)/ mean |
|---|---|---|---|---|
| | | 0 | +3 | |
| TRAF3IP3_pY179 | GQQIYpYHK | pY | | 1.5 |
| CD247_pY72 | SADAPAYQQGQNQLpYNELNLGR | pY | L | 1.5 |
| CD28_pY218 | DFAApYR | pY | | 1.3 |
| ARHGEF6_pY644 | KPSEEEpYVIR | pY | R | 1.2 |
| PLCG2_pY1245 | EFSVNENQLQLpYQEK | pY | K | 1.2 |
| ITK_pY512 | FVLDDQpYTSSTGTK | pY | S | 1.0 |
| TRAF3IP3_pY178/179 | GQQIpYpYHK | pY | K | 0.9 |
| C9orf78_pY277 | ATDDpYHYEK | pY | E | 0.6 |
| RBMX_pY335 | SDLpYSSGR | pY | G | 0.6 |
| CD3E_pY188 | ERPPPVPNPDpYEPIR | pY | I | 0.5 |
| EXOC4_pY51 | LEEApYEK | pY | | 0.5 |
| PJA2_pY28 | AVWPKPAGGpYQTITGR | pY | I | 0.4 |
| CD247_pY142 | GHDGLpYQGLSTATK | pY | L | 0.4 |
| LCP1_pY300 | AYpYHLLEQVAPK | pY | L | 0.4 |
| RFTN1_pY20 | RPGNIpYSTLK | pY | L | 0.3 |
| ASNS_pY216 | DVPLHALpYDNVEK | pY | V | 0.3 |

TABLE 10-continued

The QuadM-TrM tandem Superbinder captures more pTyr-including peptides than the TrM human Src Superbinder.

| Protein name_Tyr phosphosite | Sequence of pTyr-including peptide | Amino Acid Position 0 | Amino Acid Position +3 | (QT-TrM)/ mean |
|---|---|---|---|---|
| ZAP70_pY292 | IDTLNSDGpYTPEPAR | pY | E | 0.3 |
| HCLS1_pY175 | AALGpYDYK | pY | K | 0.3 |
| ARID1A_pY229 | SAYPPPAPApYALSSPR | pY | S | 0.3 |
| ARFGAP2_pY445 | EVDAEpYEAR | pY | R | 0.3 |
| CD3D_pY160 | DDAQpYSHLGGNWAR | pY | L | 0.3 |
| CLPTM1L_pY527 | VNEFGESpYEEK | pY | K | 0.3 |
| CD28_pY206/209 | HpYQPpYAPPR | pY | pY/P | 0.3 |
| ARHGAP15_pY219 | SSSTELLSHpYDSDIK | pY | D | 0.3 |
| LAT_pY220 | EpYVNVSQELHPGAAK | pY | V | 0.2 |
| CD3G_pY160 | QTLLPNDQLpYQPLK | pY | L | 0.2 |
| ZAP70_pY164 | MPWpYHSSLTR | PY | S | 0.2 |
| TLR7_pY1041 | NALATDNHVApYSQVFK | PY | V | 0.1 |
| CD84_pY316 | EEPVNTVpYSEVQFADK | PY | V | 0.1 |
| LIMD2_pY102 | GNpYDEGFGR | PY | G | 0.0 |
| CD247_pY111 | NPQEGLpYNELQK | PY | L | 0.0 |
| DBN1_pY34 | ALpYTYEDGSDDLK | PY | E | 0.0 |
| CD3G_pY171 | EDDQpYSHLQGNQLR | PY | L | 0.0 |
| CD3E_pY199 | DLpYSGLNQR | PY | L | 0.0 |
| PTPN7_pY149 | AQSQEDGDpYINANYIR | PY | A | 0.0 |
| SPEN_pY1399 | ASALpYESSR | PY | S | -0.1 |
| CD84_pY296 | IpYDEILQSK | PY | I | -0.1 |
| LAT_pY110 | DSDGANSVASpYENEGASG1R | PY | E | -0.2 |
| THUMPD1_pY22 | AQpYVLAK | PY | A | -0.2 |
| SIT1_pY148 | pYSEVVLDSEPK | PY | V | -0.2 |

Shown are the relative preferences of each pTyr-including peptide for the QuadM-TrM tandem Superbinder versus the TrM human Src SH2 Superbinder, as defined by the value of "(QT-TrM)/Mean", where "QT" represents the amount of pTyr-including peptide captured by the QuadM-TrM tandem Superbinder, "TrM" represents the amount of pTyr-including peptide captured by the TrM human Src SH2 Superbinder, and "Mean" represents the mean amount of pTyr-including peptide captured by both the QuadM-TrM tandem Superbinder and the TrM human Src SH2 Superbinder. Yellow and blue shaded boxes indicate hydrophobic and hydrophilic residues, respectively, at the pTyr+3 position in the sequence of the pTyr-including peptide.

CONCLUDING REMARKS

All documents referred to herein are fully incorporated by reference as if each individual publication or patent application were specifically and individually indicated to be incorporated by reference.

Changes and modifications not expressly discussed herein may be apparent and may be made by those skilled in the art based on the present disclosure.

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein unless the context clearly dictates otherwise.

It will be further understood that the term "comprise", including any variation thereof, is intended to be open-ended and means "include, but not limited to," unless otherwise specifically indicated to the contrary, that is, to include particular recited elements or components without excluding any other element or component.

When a list of items is given herein with an "or" before the last item, any one of the listed items or any suitable combination of two or more of the listed items may be selected and used.

As used in this specification and the appended claims, all ranges or lists as given are intended to convey any intermediate value or range or any sublist contained therein.

The following standard one-letter and three-letter abbreviations for the amino acid residues may be used throughout the specification: A, Ala—alanine; R, Arg—arginine; N, Asn—asparagine; D, Asp—aspartic acid; C, Cys—cysteine; Q, Gln—glutamine; E, Glu—glutamic acid; G, Gly—glycine; H, His—histidine; I, Ile—isoleucine; L, Leu—leucine; K, Lys—lysine; M, Met—methionine; F, Phe—phenylalanine; P, Pro—proline; S, Ser—serine; T, Thr—threonine; W, Trp—tryptophan; Y, Tyr—tyrosine; and V, Val—valine.

The term "ligand" means a molecule that binds another molecule or target.

It will thus be appreciated that the methods of the present disclosure in different embodiments provides a method of profiling a kinase activity by identifying and quantifying pTyr-including peptides that may be present in the kinase, for example in the activation loop, or at other Tyr phosphorylation sites in the kinase.

The pTyr-including peptides removed from the sample after binding to a SH2 Superbinder can be identified by mass spectrometry and quantitated by mass spectrometry, such as multiple reaction monitoring, selective reaction monitoring or parallel reaction monitoring mass spectrometry.

In different embodiments, the method may be advantageously employed for diagnosis or prognosis of any human disease, such as a cancer, in which a tyrosine kinase activity is dysregulated, by profiling tyrosine kinase activity in a human cell, tissue or biopsy. Specifically contemplated herein is diagnosis or prognosis of breast cancer, lung cancer, prostate cancer and leukemia.

Also contemplated is a method of profiling tyrosine kinase activity to identify a tyrosine kinase that promotes a drug resistance of a human cancer, or growth of a human cancer, or metastasis of a human cancer. As would be understood, identification and quantification of pTyr-including peptides from a tyrosine kinase allows for such identification, for example by comparing to the tyrosine kinase activity profile from a reference non-cancer sample or from finding that a tyrosine kinase is activated in a substantial proportion of the profiles from samples of a given cancer type.

It will also be appreciated that in different embodiments, a tyrosine kinase or other phosphorylated tyrosine containing proteins may be identified as a target for pharmacologic intervention, for example by identifying a tyrosine kinase or other phosphorylated tyrosine containing protein whose phosphorylation is changed (for example in magnitude or frequency) during or following a treatment that may include inhibition of a tyrosine kinase, chemotherapy, inhibition of PD-1, and inhibition of CTLA-4.

Of course, the above described embodiments of the invention are intended to be illustrative only and in no way limiting. The described embodiments of the invention are susceptible to many modifications of form, arrangement of parts, details and order of operation. The invention, rather, is intended to encompass all such modification within its scope, as defined by the claims.

SEQUENCES

SEQ ID NO: 1, Homo sapiens, Full-length Src protein
MetGlySerAsnLysSerLysProLysAspAlaSerGlnArgArgSerLeuGluProA
laGluAsnValHisGlyAlaGlyGlyAlaPheProAlaSerGlnThrProSerLysProAlaSerAlaAsp
GlyHisArgGlyProSerAlaAlaPheAlaProAlaAlaAlaGluProLysLeuPheGlyGlyPheAsnSerS
erAspThrValThrSerProGlnArgAlaGlyProLeuAlaGlyGlyValThrThrPheValAlaLeuTyrAsp
TyrGluSerArgThrGluThrAspLeuSerPheLysLysGlyGluArgLeuGlnIleValAsnAsnThrGluGl
yAspTrpTrpLeuAlaHisSerLeuSerThrGlyGlnThrGlyTyrIleProSerAsnTyrValAlaProSerAs
pSerIleGlnAlaGluGluTrpTyrPheGlyLysIleThrArgArgGluSerGluArgLeuLeuLeuAsnAlaGl
uAsnProArgGlyThrPheLeuValArgGluSerGluThrThrLysGlyAlaTyrCysLeuSerValSerAsp
PheAspAsnAlaLysGlyLeuAsnValLysHisTyrLysIleArgLysLeuAspSerGlyGlyPheTyrIleTh
rSerArgThrGlnPheAsnSerLeuGlnGlnLeuValAlaTyrTyrSerLysHisAlaAspGlyLeuCysHis
ArgLeuThrThrValCysProThrSerLysProGlnThrGlnGlyLeuAlaLysAspAlaTrpGluIleProArg
GluSerLeuArgLeuGluValLysLeuGlyGlnGlyCysPheGlyGluValTrpMetGlyThrTrpAsnGlyT
hrThrArgValAlaIleLysThrLeuLysProGlyThrMetSerProGluAlaPheLeuGlnGluAlaGlnValM
etLysLysLeuArgHisGluLysLeuValGlnLeuTyrAlaValValSerGluGluProIleTyrIleValThrGlu
TyrMetSerLysGlySerLeuLeuAspPheLeuLysGlyGluThrGlyLysTyrLeuArgLeuProGlnLeu
ValAspMetAlaAlaGlnIleAlaSerGlyMetAlaTyrValGluArgMetAsnTyrValHisArgAspLeuArg
AlaAlaAsnIleLeuValGlyGluAsnLeuValCysLysValAlaAspPheGlyLeuAlaArgLeuIleGluAs
pAsnGluTyrThrAlaArgGlnGlyAlaLysPheProIleLysTrpThrAlaProGluAlaAlaLeuTyrGlyAr
gPheThrIleLysSerAspValTrpSerPheGlyIleLeuLeuThrGluLeuThrThrLysGlyArgValProTy
rProGlyMetValAsnArgGluValLeuAspGlnValGlyArgGlyTyrArgMetProCysProProGluCys
ProGluSerLeuHisAspLeuMetCysGlnCysTrpArgLysGluProGluGluArgProThrPheGluTyr
LeuGlnAlaPheLeuGluAspTyrPheThrSerThrGluProGlnTyrGlnProGlyGluAsnLeu SEQ ID NO: 2, Homo sapiens, Full-length Grb2 protein
MetGluAlaIleAlaLysTyrAspPheLysAlaThrAlaAspAspGluLeuSerPheLysAr
gGlyAspIleLeuLysValLeuAsnGluGluCysAspGlnAsnTrpTyrLysAlaGluLeuAsnGlyLysAs
pGlyPheIleProLysAsnTyrIleGluMetLysProHisProTrpPhePheGlyLysIleProArgAlaLysAla
GluGluMetLeuSerLysGlnArgHisAspGlyAlaPheLeuIleArgGluSerGluSerAlaProGlyAspP
heSerLeuSerValLysPheGlyAsnAspValGlnHisPheLysValLeuArgAspGlyAlaGlyLysTyrP
heLeuTrpValValLysPheAsnSerLeuAsnGluLeuValAspTyrHisArgSerThrSerValSerArgAs
nGlnGlnIlePheLeuArgAspIleGluGlnValProGlnGlnProThrTyrValGlnAlaLeuPheAspPheA
spProGlnGluAspGlyGluLeuGlyPheArgArgGlyAspPheIleHisValMetAspAsnSerAspProA
snTrpTrpLysGlyAlaCysHisGlyGlnThrGlyMetPheProArgAsnTyrValThrProValAsnArgAs
nVal

| SEQUENCES |
| --- |

SEQ ID NO: 3, *Homo sapiens*, Full-length Fyn protein
MetGlyCysValGlnCysLysAspLysGluAlaThrLysLeuThrGluGluArgAspGlyS
erLeuAsnGlnSerSerGlyTyrArgTyrGlyThrAspProThrProGlnHisTyrProSerPheGlyValThr
SerIleProAsnTyrAsnAsnPheHisAlaAlaGlyGlyGlnGlyLeuThrValPheGlyGlyValAsnSerSe
rSerHisThrGlyThrLeuArgThrArgGlyGlyThrGlyValThrLeuPheValAlaLeuTyrAspTyrGluAl
aArgThrGluAspAspLeuSerPheHisLysGlyGluLysPheGlnIleLeuAsnSerSerGluGlyAspTr
pTrpGluAlaArgSerLeuThrThrGlyGluThrGlyTyrIleProSerAsnTyrValAlaProValAspSerIle
GlnAlaGluGluTrpTyrPheGlyLysLeuGlyArgLysAspAlaGluArgGlnLeuLeuSerPheGlyAsn
ProArgGlyThrPheLeuIleArgGluSerGluThrThrLysGlyAlaTyrSerLeuSerIleArgAspTrpAsp
AspMetLysGlyAspHisValLysHisTyrLysIleArgLysLeuAspAsnGlyGlyTyrTyrIleThrThrArg
AlaGlnPheGluThrLeuGlnGlnLeuValGlnHisTyrSerGluArgAlaAlaGlyLeuCysCysArgLeuV
alValProCysHisLysGlyMetProArgLeuThrAspLeuSerValLysThrLysAspValTrpGluIlePro
ArgGluSerLeuGlnLeuIleLysArgLeuGlyAsnGlyGlnPheGlyGluValTrpMetGlyThrTrpAsnGl
yAsnThrLysValAlaIleLysThrLeuLysProGlyThrMetSerProGluSerPheLeuGluGluAlaGlnIl
eMetLysLysLeuLysHisAspLysLeuValGlnLeuTyrAlaValValSerGluGluProIleTyrIleValThr
GluTyrMetAsnLysGlySerLeuLeuAspPheLeuLysAspGlyGluGlyArgAlaLeuLysLeuProAs
nLeuValAspMetAlaAlaGlnValAlaAlaGlyMetAlaTyrIleGluArgMetAsnTyrIleHisArgAspLeu
ArgSerAlaAsnIleLeuValGlyAsnGlyLeuIleCysLysIleAlaAspPheGlyLeuAlaArgLeuIleGluA
spAsnGluTyrThrAlaArgGlnGlyAlaLysPheProIleLysTrpThrAlaProGluAlaAlaLeuTyrGlyAr
gPheThrIleLysSerAspValTrpSerPheGlyIleLeuLeuThrGluLeuValThrLysGlyArgValProTy
rProGlyMetAsnAsnArgGluValLeuGluGlnValGluArgGlyTyrArgMetProCysProGlnAspCy
sProIleSerLeuHisGluLeuMetIleHisCysTrpLysLysAspProGluGluArgProThrPheGluTyrL
euGlnSerPheLeuGluAspTyrPheThrAlaThrGluProGlnTyrGlnProGlyGluAsnLeu SEQ ID NO: 4, Artificial Sequence, Wild-type human Src SH2 domain
AspSerIleGlnAlaGluGluTrpTyrPheGlyLysIleThrArgArgGluSerGluArgLeuL
euLeuAsnAlaGluAsnProArgGlyThrPheLeuValArgGluSerGluThrThrLysGlyAlaTyrCysLe
uSerValSerAspPheAspAsnAlaLysGlyLeuAsnValLysHisTyrLysIleArgLysLeuAspSerGly
GlyPheTyrIleThrSerArgThrGlnPheAsnSerLeuGlnGlnLeuValAlaTyrTyrSerLysHisAlaAs
pGlyLeuCysHisArgLeuThrThrValCysProThrSerLys SEQ ID NO: 5, Artificial Sequence, TrM human Src SH2 domain
AspSerIleGlnAlaGluGluTrpTyrPheGlyLysIleThrArgArgGluSerGluArgLeuL
euLeuAsnAlaGluAsnProArgGlyThrPheLeuValArgGluSerGluThrThrLysGlyAlaTyrCysLe
uSerValSerAspPheAspAsnAlaLysGlyLeuAsnValLysHisTyrLysIleArgLysLeuAspSerGly
GlyPheTyrIleThrSerArgThrGlnPheAsnSerLeuGlnGlnLeuValAlaTyrTyrSerLysHisAlaAs
pGlyLeuCysHisArgLeuThrThrValCysProThrSerLys SEQ ID NO: 6, Artificial Sequence, Wild-type human Grb2 SH2 domain
MetLysProHisProTrpPhePheGlyLysIleProArgAlaLysAlaGluGluMetLeuSe
rLysGlnArgHisAspGlyAlaPheLeuIleArgGluSerGluSerAlaProGlyAspPheSerLeuSerValL
ysPheGlyAsnAspValGlnHisPheLysValLeuArgAspGlyAlaGlyLysTyrPheLeuTrpValValLy
sPheAsnSerLeuAsnGluLeuValAspTyrHisArgSerThrSerValSerArgAsnGlnGlnIlePheLeu
ArgAspIleGluGlnValProGlnGlnPro SEQ ID NO: 7, Artificial Sequence, TrM human Grb2 SH2 domain
MetLysProHisProTrpPhePheGlyLysIleProArgAlaLysAlaGluGluMetLeuSe
rLysGlnArgHisAspGlyAlaPheLeuIleArgGluSerGluValProGlyAspPheAlaLeuSerValL
ysPheGlyAsnAspValGlnHisPheLeuValLeuArgAspGlyAlaGlyLysTyrPheLeuTrpValValLy
sPheAsnSerLeuAsnGluLeuValAspTyrHisArgSerThrSerValSerArgAsnGlnGlnIlePheLeu
ArgAspIleGluGlnValProGlnGlnProLeuIleAsnGluPhe SEQ ID NO: 8, Artificial Sequence, Wild-type human Fyn SH2 domain
AlaProValAspSerIleGlnAlaGluGluTrpTyrPheGlyLysLeuGlyArgLysAspAla
GluArgGlnLeuLeuSerPheGlyAsnProArgGlyThrPheLeuIleArgGluSerGluThrThrLysGlyAl
aTyrSerLeuSerIleArgAspTrpAspAspMetLysGlyAspHisValLysHisTyrLysIleArgLysLeuA
spAsnGlyGlyTyrTyrIleThrThrArgAlaGlnPheGluThrLeuGlnGlnLeuValGlnHisTyrSerGluA
rgAlaAlaGlyLeuCysCysArgLeuValValProCysHisLysGly SEQ ID NO: 9, Artificial Sequence, TrM human Fyn SH2 domain
AlaProValAspSerIleGlnAlaGluGluTrpTyrPheGlyLysLeuGlyArgLysAspAla
GluArgGlnLeuLeuSerPheGlyAsnProArgGlyThrPheLeuIleArgGluSerGluThrValLysGlyAl
aTyrAlaLeuSerIleArgAspTrpAspAspMetLysGlyAspHisValLysHisTyrLeuIleArgLysLeuA
spAsnGlyGlyTyrTyrIleThrThrArgAlaGlnPheGluThrLeuGlnGlnLeuValGlnHisTyrSerGluA
rgAlaAlaGlyLeuCysCysArgLeuValValProCysHisLysGly SEQ ID NO: 10, Artificial Sequence, Wild-type human Src SH2 domain
with hexahistidine and GST tags
MetLysHisHisHisHisHisHisAsnThrSerSerAsnSerMetSerProIleLeuGlyTyr
TrpLysIleLysGlyLeuValGlnProThrArgLeuLeuLeuGluTyrLeuGluGluLysTyrGluGluHisLe
uTyrGluArgAspGluGlyAspLysTrpArgAsnLysLysPheGluLeuGlyLeuGluPheProAsnLeuP
roTyrTyrIleAspGlyAspValLysLeuThrGlnSerMetAlaIleIleArgTyrIleAlaAspLysHisAsnMet
LeuGlyGlyCysProLysGluArgAlaGluIleSerMetLeuGluGlyAlaValLeuAspIleArgTyrGlyVal
SerArgIleAlaTyrSerLysAspPheGluThrLeuLysValAspPheLeuSerLysLeuProGluMetLeuL
ysMetPheGluAspArgLeuCysHisLysThrTyrLeuAsnGlyAspHisValThrHisProAspPheMetL
euTyrAspAlaLeuAspValValLeuTyrMetAspProMetCysLeuAspAlaPheProLysLeuValCys

| SEQUENCES |
|---|
| PheLysLysArgIleGluAlaIleProGlnIleAspLysTyrLeuLysSerSerLysTyrIleAlaTrpProLeuGl<br>nGlyTrpGlnAlaThrPheGlyGlyGlyAspHisProProThrSerGlySerGlyGlyGlyGlyGlyTrpMetS<br>erGluAsnLeuTyrPheGlnGlyAlaMetAspSerIleGlnAlaGluGluTrpTyrPheGlyLysIleThrArgA<br>rgGluSerGluArgLeuLeuLeuAsnAlaGluAsnProArgGlyThrPheLeuValArgGluSerGluThrT<br>hrLysGlyAlaTyrCysLeuSerValSerAspPheAspAsnAlaLysGlyLeuAsnValLysHisTyrLysIle<br>ArgLysLeuAspSerGlyGlyPheTyrIleThrSerArgThrGlnPheAsnSerLeuGlnGlnLeuValAlaT<br>yrTyrSerLysHisAlaAspGlyLeuCysHisArgLeuThrThrValCysProThrSerLys<br><br>SEQ ID NO: 11, Artificial Sequence, TrM human Src SH2 domain with<br>hexahistidine and GST tags<br>MetLysHisHisHisHisHisHisAsnThrSerSerAsnSerMetSerProIleLeuGlyTyr<br>TrpLysIleLysGlyLeuValGlnProThrArgLeuLeuLeuGluTyrLeuGluGluLysTyrGluGluHisLe<br>uTyrGluArgAspGluGlyAspLysTrpArgAsnLysLysPheGluLeuGlyLeuGluPheProAsnLeuP<br>roTyrTyrIleAspGlyAspValLysLeuThrGlnSerMetAlaIleIleArgTyrIleAlaAspLysHisAsnMet<br>LeuGlyGlyCysProLysGluArgAlaGluIleSerMetLeuGluGlyAlaValLeuAspIleArgTyrGlyVal<br>SerArgIleAlaTyrSerLysAspPheGluThrLeuLysValAspPheLeuSerLysLeuProGluMetLeuL<br>ysMetPheGluAspArgLeuCysHisLysThrTyrLeuAsnGlyAspHisValThrHisProAspPheMetL<br>euTyrAspAlaLeuAspValValLeuTyrMetAspProMetCysLeuAspAlaPheProLysLeuValCys<br>PheLysLysArgIleGluAlaIleProGlnIleAspLysTyrLeuLysSerSerLysTyrIleAlaTrpProLeuGl<br>nGlyTrpGlnAlaThrPheGlyGlyGlyAspHisProProThrSerGlySerGlyGlyGlyGlyGlyTrpMetS<br>erGluAsnLeuTyrPheGlnGlyAlaMetAspSerIleGlnAlaGluGluTrpTyrPheGlyLysIleThrArgA<br>rgGluSerGluArgLeuLeuLeuAsnAlaGluAsnProArgGlyThrPheLeuValArgGluSerGluThrV<br>alLysGlyAlaTyrAlaLeuSerValSerAspPheAspAsnAlaLysGlyLeuAsnValLysHisTyrLeuIle<br>ArgLysLeuAspSerGlyGlyPheTyrIleThrSerArgThrGlnPheAsnSerLeuGlnGlnLeuValAlaT<br>yrTyrSerLysHisAlaAspGlyLeuCysHisArgLeuThrThrValCysProThrSerLys<br><br>SEQ ID NO: 12, Artificial Sequence, QuadM human Src 5H2 domain<br>AspSerIleGlnAlaGluGluTrpTyrPheGlyLysIleThrArgArgGluSerGluArgLeuL<br>euLeuAsnAlaGluAsnProArgGlyThrPheLeuValArgGluSerGluThrValLysGlyAlaTyrAlaLe<br>uSerValSerAspPheAspAsnAlaLysGlyLeuAsnValLysHisTyrLeuIleArgLysLeuAspSerGly<br>GlyPheTyrIleTrpSerArgThrGlnPheAsnSerLeuGlnGlnLeuValAlaTyrTyrSerLysHisAlaAs<br>pGlyLeuCysHisArgLeuThrThrValCysProThrSerLys<br><br>SEQ ID NO: 13, Artificial Sequence, QuadM human Src SH2 domain<br>with hexahistidine tag<br>MetLysHisHisHisHisHisHisProMetSerAspTyrAspIleProThrThrGluAsnLeu<br>TyrPheGlnGlyAlaMetAspSerIleGlnAlaGluGluTrpTyrPheGlyLysIleThrArgArgGluSerGlu<br>ArgLeuLeuLeuAsnAlaGluAsnProArgGlyThrPheLeuValArgGluSerGluThrValLysGlyAlaT<br>yrAlaLeuSerValSerAspPheAspAsnAlaLysGlyLeuAsnValLysHisTyrLeuIleArgLysLeuAs<br>pSerGlyGlyPheTyrIleTrpSerArgThrGlnPheAsnSerLeuGlnGlnLeuValAlaTyrTyrSerLysH<br>isAlaAspGlyLeuCysHisArgLeuThrThrValCysProThrSerLys<br><br>SEQ ID NO: 14, Artificial Sequence, double-mutant human Src SH2<br>domain<br>AspSerIleGlnAlaGluGluTrpTyrPheGlyLysIleThrArgArgGluSerGluArgLeuL<br>euLeuAsnAlaGluAsnProArgGlyThrPheLeuValArgGluSerGluThrValLysGlyAlaTyrAlaLe<br>uSerValSerAspPheAspAsnAlaLysGlyLeuAsnValLysHisTyrLysIleArgLysLeuAspSerGly<br>GlyPheTyrIleThrSerArgThrGlnPheAsnSerLeuGlnGlnLeuValAlaTyrTyrSerLysHisAlaAs<br>pGlyLeuCysHisArgLeuThrThrValCysProThrSerLys<br><br>SEQ ID NO: 15, Artificial Sequence, QuadM-TrM human Src SH2<br>tandem domain<br>AspSerIleGlnAlaGluGluTrpTyrPheGlyLysIleThrArgArgGluSerGluArgLeu<br>LeuLeuAsnAlaGluAsnProArgGlyThrPheLeuValArgGluSerGluThrValLysGlyAlaTyrAlaL<br>euSerValSerAspPheAspAsnAlaLysGlyLeuAsnValArgHisTyrLeuIleArgLysLeuAspSerGl<br>yGlyPheTyrIleTrpSerArgThrGlnPheAsnSerLeuGlnGlnLeuValAlaTyrTyrSerLysHisAlaA<br>spGlyLeuSerHisArgLeuThrThrValSerProThrSerLysGlyGlySerGlyGlySerMetAspSerIle<br>GlnAlaGluGluTrpTyrPheGlyLysIleThrArgArgGluSerGluArgLeuLeuLeuAsnAlaGluAsnPr<br>oArgGlyThrPheLeuValArgGluSerGluThrValLysGlyAlaTyrAlaLeuSerValSerAspPheAsp<br>AsnAlaLysGlyLeuAsnValArg HisTyrLeuIleArgLysLeuAspSerGlyGlyPheTyrIleThrSerArg<br>ThrGlnPheAsnSerLeuGlnGlnLeuValAlaTyrTyrSerLysHisAlaAspGlyLeuSerHisArgLeuT<br>hrThrValSerProThrSerLys |

What is claimed is:

1. A method of profiling protein tyrosine phosphorylation of a test sample, the method comprising:
    separately contacting the test sample and a control sample with an SH2 Superbinder in order to bind pTyr-including peptides contained in each of the test sample and the control sample with the SH2 Superbinder;
    separately isolating the bound pTyr-including peptides from each of the test sample and the control sample;
    identifying the isolated pTyr-including peptides by mass spectrometry, said mass spectrometry comprising multiple reaction monitoring, selective reaction monitoring, parallel reaction monitoring, or tandem mass spectrometry (MS/MS) techniques; and
    comparing the profile obtained for the test sample with the profile obtained for a control sample,
    wherein the SH2 Superbinder is a variant SH2 domain of a parent SH2 domain and comprises the sequence of SEQ ID NO: 5, 7, 9, 11, 12, 13, 14 or 15, the SH2 Superbinder comprising one or more amino acid substitutions in the pTyr-binding pocket as compared to the parent SH2 domain from which the SH2 Superbinder varies, the one or more amino acid substitutions resulting in the SH2 superbinder having at least 10-fold greater affinity for a pTyr residue as compared to the parent SH2 domain, and
    wherein the control sample is a sample from the same source as the test sample but obtained at a different time point than the test sample, is a sample from the same source as the test sample but having different exposure to a drug as compared to the test sample, is from a source known to be free from a disease, or is from a source known to be have a disease or to be involved in a disease.

2. The method according to claim 1, further comprising quantifying the isolated pTyr-including peptides by mass spectrometry, said mass spectrometry comprising multiple reaction monitoring, selective reaction monitoring, parallel reaction monitoring, or tandem mass spectrometry (MS/MS) techniques.

3. The method of claim 1, wherein the SH2 Superbinder is a variant of a mammalian SH2 domain.

4. The method of claim 1, wherein the SH2 Superbinder is a variant of a Src, Grb2 or Fyn SH2 domain.

5. The method of claim 1, wherein the SH2 Superbinder is a triple mutant SH2 variant or a quadruple mutant SH2 domain.

6. The method of claim 1, wherein the SH2 Superbinder is contained within a fusion protein that comprises one or more additional SH2 Superbinders.

7. The method of claim 1, wherein the SH2 Superbinder is immobilized on a solid support.

8. The method of claim 1, wherein the sample is obtained from a subject.

9. The method of claim 8, wherein the sample is serum, plasma, urine, blood, tissue or a tissue extract.

10. The method of claim 8, wherein the subject is to be diagnosed with cancer, or is known to have cancer.

11. The method of claim 10, wherein the cancer is breast cancer, lung cancer, prostate cancer or leukemia.

12. The method of claim 1, wherein the sample has been exposed to a tyrosine kinase inhibitor, a chemotherapy agent, a PD-1 inhibitor, or a CTLA-4 inhibitor.

13. The method of claim 1, wherein the isolated pTyr-including peptides are pTyr-including peptides of substrates of a specific protein tyrosine kinase or a specific protein tyrosine phosphatase.

14. The method of claim 1, wherein the isolated pTyr-including peptides include a pTyr-including peptide from an activation loop of a protein kinase or from outside the activation loop of the protein kinase.

15. The method of claim 14, wherein the protein tyrosine kinase is a tyrosine kinase, a serine/threonine kinase, a dual-specificity kinase, a MAP kinase, or a lipid kinase.

16. The method of claim 1, wherein the isolated pTyr-including peptides include a pTyr-including peptide from an immunoreceptor tyrosine-based regulatory motif (ITRM) of an immunoreceptor.

17. The method of claim 1, wherein the identifying comprises identifying a pTyr-including peptide from a regulatory region of a protein tyrosine phosphatase.

* * * * *